(12) United States Patent
Koji et al.

(10) Patent No.: US 7,001,997 B2
(45) Date of Patent: Feb. 21, 2006

(54) PROTEINS, THEIR PRODUCTION AND USE

(75) Inventors: Yoshimura Koji, Tsukuba (JP); Hikichi Yuichi, Tsukuba (JP); Nishimura Atsushi, Tsubuka (JP)

(73) Assignee: Takeda Chemical Industries, Ltd., Osaka (JP)

( * ) Notice: Subject to any disclaimer, the term of this patent is extended or adjusted under 35 U.S.C. 154(b) by 458 days.

(21) Appl. No.: 10/251,482

(22) Filed: Sep. 19, 2002

(65) Prior Publication Data

US 2003/0099631 A1 May 29, 2003

Related U.S. Application Data

(62) Division of application No. 09/171,545, filed as application No. PCT/JP97/01433 on Apr. 24, 1997, now Pat. No. 6,566,116.

(30) Foreign Application Priority Data

Apr. 25, 1996 (JP) ............................................. 8-104902

(51) Int. Cl.
*C12N 15/57* (2006.01)
*C12N 15/70* (2006.01)
*C12N 15/79* (2006.01)

(52) U.S. Cl. .................. 536/23.2; 435/69.1; 435/252.3; 435/320.1

(58) Field of Classification Search ................ 536/23.2; 435/69.1, 252.3, 252.33, 254.2, 320.1
See application file for complete search history.

(56) References Cited

U.S. PATENT DOCUMENTS 6,399,371 B1 * 6/2002 Falduto et al. .............. 435/325
6,566,116 B1 * 5/2003 Koji et al. ................... 435/226

FOREIGN PATENT DOCUMENTS

WO WO 97/19178 A2 * 5/1997
WO WO 97/40157 A1 * 10/1997

OTHER PUBLICATIONS

Cossins, J., et al., "Identification of MMP-18, a putative novel human matrix metalloprotease", Biophysical and Biochemical Research Communications, vol. 228, No. 2, pp. 494–498, 1996.*

Pendas, A.M., et al., GenEmbl database Accession No. X92521, "H. sapiens mRNA for MMP-19 protein", electronic publication date Dec. 18, 1996.*

* cited by examiner

*Primary Examiner*—Ponnathabura Achutamurthy
*Assistant Examiner*—William W. Moore
(74) *Attorney, Agent, or Firm*—David G. Conlin; Christine C. O'Day; Edwards & Angell, LLP

(57) ABSTRACT

This invention relates to a novel metalloprotease having a proteolytic activity, its partial peptide or a salt either of them, a DNA coding for the protein, a recombinant vector comprising the DNA, a transformant carrying the recombinant vector, a process for producing the protein, a pharmaceutical composition comprising the DNA, an antibody against the protein, a method for screening for a compound which activates or inhibits a proteolytic activity of the protein, a kit for screening for the compound, and a compound which activates or inhibits a proteolytic activity of the protein which is identified by the screening method or the kit. The DNA coding for the protein of the present invention can be used as a therapeutic and prophylactic composition for a variety of diseases including diabetic nephropathy, glomerulonephritis, pulmonary fibrosis, hepatolienal fibrosis, hepatocirrhosis, osteopetrosis and herniated disk. Furthermore, the protein of the present invention is useful as a screening reagent for any compounds which activate or inhibit the function of the protein of the present invention. In addition, the antibody against the protein of the present invention specifically recognizes the protein of the present invention and can be used in the quantitative determination of the protein of the present invention in a test fluid.

11 Claims, 16 Drawing Sheets

| | | | | | | | | |
|---|---|---|---|---|---|---|---|---|
|Met|Asn|Gys|Gln|Gln|Leu|Trp|Leu|Gly|Phe|Leu|Pro|Met|Thr|Val|Ser|Gly|Arg|Val|20|
|Leu|Gly|Leu|Ala|Glu|Val|Ala|Pro|Val|Asp|Tyr|Gln|Tyr|Gly|Tyr|Leu|Gln|Lys|40|
|Pro|Leu|Glu|Gly|Ser|Asn|Leu|Pro|Phe|Lys|Pro|Gln|Thr|Glu|Ala|Leu|Arg|Ala|Phe|60|
|Gln|Glu|Ala|Ser|Glu|Leu|Pro|Val|Ser|Gly|Asp|Gln|Leu|Asp|Ala|Thr|Arg|Met|80|
|Arg|Gln|Pro|Arg|Cys|Gly|Leu|Glu|Asp|Pro|Phe|Asn|Gln|Ile|Lys|Thr|Leu|Leu|100|
|Leu|Gly|Arg|Trp|Arg|Lys|Lys|His|Leu|Thr|Phe|Arg|Ile|Leu|Asn|Leu|Pro|Ser|Thr|Leu|120|
|Pro|Pro|His|Thr|Ala|Arg|Ala|Leu|Arg|Gln|Ala|Phe|Gln|Ala|Asp|Trp|Ser|Asn|Val|Ala|140|
|Pro|Leu|Thr|Phe|Gln|Glu|Val|Gln|Ala|Gly|Val|Gln|Ala|Ala|Ile|Arg|Leu|Ser|Phe|His|Gly|160|
|Arg|Gln|Ser|Ser|Tyr|Cys|Ser|Asn|Thr|Phe|Asp|Gly|Pro|Gly|Arg|Val|Leu|Ala|His|Ala|180|
|Asp|Ile|Pro|Glu|Leu|Gly|Ser|Val|His|Phe|Asp|Asp|Asp|Glu|Trp|Thr|Glu|Gly|Thr|200|
|Tyr|Arg|Gly|Val|Asn|Leu|Arg|Ile|Ile|Ala|His|Glu|Val|Gly|His|Ala|Leu|Gly|Leu|220|
|Gly|His|Ser|Arg|Tyr|Ser|Gln|Ala|Leu|Met|Ala|Pro|Val|Tyr|Glu|Tyr|Lys|Arg|Pro|His|240|
|Phe|Lys|Leu|His|Pro|Asp|Asp|Ile|Gln|Gly|Ile|Gln|Ala|Leu|Tyr|Gly|Lys|Ser|Pro|Thr|260|
|Val|Ile|Arg|Asp|Gly|Glu|Gly|Glu|Thr|Leu|Pro|Thr|Val|Pro|Pro|Val|Pro|Gly|Pro|280|
|Glu|Pro|Ser|Pro|Met|Pro|Asp|Pro|Cys|Ser|Ser|Gly|Ile|Leu|Asp|Ala|Met|Met|Ser|Gly|Pro|300|
|Arg|Gly|Lys|Thr|Tyr|Ala|Phe|Lys|Gly|Asp|Tyr|Val|Trp|Thr|Val|Ser|Asp|Ser|Gly|Ala|Ala|320|
|Gly|Pro|Leu|Phe|Arg|Val|Ser|Ala|Leu|Trp|Ile|Gly|Leu|Pro|Gly|Asn|Leu|Asp|Ala|Ala|Tyr|340|
|Val|Tyr|Ser|Pro|Arg|Arg|Thr|Gln|Trp|Ile|His|Phe|Phe|Pro|Lys|Gly|Val|Glu|Val|Trp|Arg|Tyr|360|
|Ile|Asn|Phe|Lys|Met|Ser|Pro|Gly|Phe|Pro|Lys|Leu|Val|Phe|Leu|Pro|Asn|Leu|380|
|Asp|Ala|Ala|Leu|Tyr|Asp|Gln|Leu|Asn|Gln|Lys|Val|Phe|Ser|Tyr|Pro|Lys|Gly|Tyr|400|
|Trp|Gln|Trp|Asp|Glu|Leu|Ala|Arg|Thr|Asp|Pro|Ser|Ser|Met|Pro|Gln|Ile|Lys|Gly|420|
|Leu|Phe|Thr|Gly|Val|Pro|Asn|Gln|Ser|Ala|Ala|Met|Ser|Trp|Gln|Asn|Asp|Gly|Arg|Val|440|
|Tyr|Phe|Phe|Lys|Gly|Lys|Val|Tyr|Trp|Arg|Leu|Asn|Gln|Gln|Leu|Arg|Val|Glu|Lys|Gly|460|
|Tyr|Pro|Arg|Asn|Ile|Ser|His|Asn|Trp|Met|His|Cys|Arg|Pro|Arg|Thr|Ile|Asp|Thr|Thr|480|
|Pro|Ser|Gly|Gly|Asn|Thr|Thr|Pro|Ser|Gly|Thr|Gly|Ile|Thr|Leu|Asp|Thr|Thr|Leu|Ser|500|
|Ala|Thr|Glu|Thr|Thr|Phe|Glu|Tyr|508|

```
Tyr Leu Leu Gly Arg Trp Arg Lys His Leu Thr Phe Arg Ile Leu Asn Leu Pro            20
Ser Thr Leu Pro Pro His Thr Ala Arg Ala Leu Arg Gln Asp Ala Phe Trp Ser            40
Asn Val Ala Pro Leu Thr Phe Gln Glu Val Gln Ala Ala Asp Ile Arg Leu Ser            60
Phe His Gly Arg Gln Ile Ser Ser Tyr Cys Ser Asn Thr Phe Asp Gly Arg Val Leu        80
Ala His Ala Asp Arg Pro Glu Pro Glu Leu Gly Ser Val His Ile Phe Ala Asp Ala Thr   100
Glu Gly Thr Tyr Arg Gly Val Asn Leu Arg Gln Ala Ile Ala Ala Ala His Val Gly Ala   120
Leu Gly Leu Gly His Ser Arg Tyr Ser Arg Gln Tyr Ala Leu Met Ala Pro Val Glu Tyr   140
Arg Pro His Phe Lys Pro Leu Asp Ala Gly Glu Val Gly Ile Leu Tyr Leu Tyr Gly Lys   160
Lys Ser Pro Val Ile Arg Asp Ser Gly Glu Glu Thr Val Ala Leu Pro Val Pro Pro       180
Val Pro Thr Glu Pro Ser Pro Met Asp Cys Ser Ser Glu Leu Asp Thr Ala Met Met       200
Leu Gly Pro Arg Gly Lys Tyr Ala Phe Lys Gly Asp Tyr Val Thr Val Ser Asp Leu       220
Ser Gly Pro Gly Leu Phe Ser Arg Val Ala Leu Trp Glu Leu Pro Gly Ala Asn Leu       240
Asp Ala Ala Val Tyr Ser Pro Arg Thr Gln Trp Ile His Phe Lys Leu Gly Asp Arg Val Glu 260
Trp Arg Tyr Ile Asn Phe Ala Leu Thr Gly Met Ser Pro Gly Leu Asn Lys Phe Leu Lys Gly 280
Pro Asn Leu Asp Trp Gln Ala Ala Arg Thr Asp Ser Ser Phe Ser Tyr Pro Tyr Leu Pro   300
Ser Gly Tyr Phe Pro Gln Leu Phe Gly Val Pro Ala Met Ala Ala Gln Ala Met Met Gln Asp 320
Ile Lys Gly Leu Tyr Pro Lys Gly Thr Phe Lys Gly Val Pro Ser Tyr Pro Lys Gly Leu Arg 340
Gly Arg Val Tyr Phe Arg Asn Lys Val Tyr Arg Ala Leu Asn Gln Gln Leu Met Arg Ala Val 360
Glu Lys Gly Tyr Pro Ser Gly Ile Ser His His Met Cys Arg Pro Arg Thr Ile 380
Asp Thr Thr Pro Ser Gly Gly Asn Thr Pro Thr Ser Gly Ile Thr Gly Thr Leu Asp        400
Thr Leu Ser Ala Thr Glu Thr Phe Pro Glu Tyr                                          411
```

FIG. 3

```
Gln Lys Thr Leu Lys Tyr Leu Leu Gly Arg Trp Arg Lys Lys His Leu Thr Phe Arg          20
Ile Leu Asn Leu Pro Ser Thr Leu Pro Pro His Ala Arg Ala Ala Leu Arg Gln Ala          40
Phe Gln Asp Trp Ser Asn Val Ala Pro Leu Thr Phe Gln Glu Val Gln Ala Gly Ala          60
Asp Ile Arg Leu Ser Phe His Gly Ala Pro Arg Ile Ser Asn Thr Phe Asp Ala Gly          80
Pro Gly Arg Val Leu Ala His Ala Asp Ile Pro Glu Leu Ser Cys Ser Val His Asp Glu     100
Asp Glu Phe Trp Thr Glu Gly Leu Thr Gly Tyr Arg Asn Leu Arg Gly Val Ala Ala His     120
Glu Val Gly His Ala Leu Gly Leu Gly His Ser Ser Arg Tyr Ser Gln Ala Leu Met Ala Pro 140
Val Tyr Glu Gly Tyr Arg Pro Phe Lys Leu His Pro Asp Asp Val Ala Gly Ile Gln Leu     160
Ala Leu Tyr Gly Lys Ser Pro Val Ile Arg Asp Glu Glu Glu Gly Thr Glu Leu             180
Pro Thr Val Pro Pro Thr Pro Gly Pro Ser Pro Met Pro Asp Pro Cys Ser Ser Glu         200
Leu Asp Ala Met Leu Gly Arg Gly Lys Thr Tyr Ala Phe Lys Gly Asp Tyr Val             220
Trp Thr Val Ser Gly Pro Gly Pro Leu Phe Ala Ser Ala Leu Trp Glu Gly Gly             240
Leu Pro Gly Asn Asp Val Tyr Ile Asn Phe Ala Ala Val Thr Gln Ile Trp Pro His Phe     260
Lys Gly Asp Lys Val Glu Ser Gly Tyr Pro Arg Thr Ser Met Ser Pro Gly Phe Pro Lys Lys 280
Leu Asn Arg Val Pro Ala Leu Asp Trp Gln Leu Ala Leu Tyr Trp Pro Leu Asn Gln Lys Val 300
Phe Leu Phe Lys Gly Ser Tyr Gly Leu Phe Thr Gln Gln Trp Asp Thr Asp Phe Ser         320
Ser Tyr Pro Lys Pro Ile Leu Lys Gly Tyr Val Phe Thr Gly Val Pro Ser Ala Ala         340
Met Ser Trp Gln Asp Gly Arg Val Tyr Gly Arg Lys Lys Val Trp Arg Leu Asn             360
Gln Gln Leu Arg Val Glu Lys Gly Tyr Pro Arg His Ile Ser Asn Trp Met His Cys Asn     380
Arg Pro Arg Thr Ile Asp Asp Thr Thr Pro Ser Gly Asn Thr Thr Pro Ser Gly Thr Gly     400
Ile Thr Leu Asp Thr Leu Ser Ala Thr Thr Glu Gly Phe                                 416
```

```
                    10         20         30         40         50
           AAGAGCCCCTCTGCCTAGCACTGCTCCCCCAAGGCTCCCAGAAATCTCAG 60         70         80         90        100
           GTCAGAGGCACGGACAGCCTCTGGAGCTCTCGTCTGGTGGGACCATGAAC
                                                           M   N 110        120        130        140        150
           TGCCAGCAGCTGTGGCTGGGCTTCCTACTCCCCATGACAGTCTCAGGCCG
             C   Q   Q   L   W   L   G   F   L   L   P   M   T   V   S   G   R 160        170        180        190        200
           GGTCCTGGGGCTTGCAGAGGTGGCGCCCGTGGACTACCTGTCACAATATG
               V   L   G   L   A   E   V   A   P   V   D   Y   L   S   Q   Y G 210        220        230        240        250
           GGTACCTACAGAAGCCTCTAGAAGGATCTAATAACTTCAAGCCAGAAGAT
               Y   L   Q   K   P   L   E   G   S   N   N   F   K   P   E   D 260        270        280        290        300
           ATCACCGAGGCTCTGAGAGCTTTTCAGGAAGCATCTGAACTTCCAGTCTC
             I   T   E   A   L   R   A   F   Q   E   A   S   E   L   P   V   S 310        320        330        340        350
           AGGTCAGCTGGATGATGCCACAAGGGCCCGCATGAGGCAGCCTCGTTGTG
               G   Q   L   D   D   A   T   R   A   R   M   R   Q   P   R   C   G 360        370        380        390        400
           GCCTAGAGGATCCCTTCAACCAGAAGACCCTTAAATACCTGTTGCTGGGC
               L   E   D   P   F   N   Q   K   T   L   K   Y   L   L   L   G 410        420        430        440        450
           CGCTGGAGAAAGAAGCACCTGACTTTCCGCATCTTGAACCTGCCCTCCAC
               R   W   R   K   K   H   L   T   F   R   I   L   N   L   P   S   T
```

FIG. 4A

```
       460        470        480        490        500
CCTTCCACCCCACACAGCCCGGGCAGCCCTGCGTCAAGCCTTCCAGGACT
  L  P  P  H  T  A  R  A  A  L  R  Q  A  F  Q  D  W 510        520        530        540        550
GGAGCAATGTGGCTCCCTTGACCTTCCAAGAGGTGCAGGCTGGTGCGGCT
   S  N  V  A  P  L  T  F  Q  E  V  Q  A  G  A  A 560        570        580        590        600
GACATCCGCCTCTCCTTCCATGGCCGCCAAAGCTCGTACTGTTCCAATAC
  D  I  R  L  S  F  H  G  R  Q  S  S  Y  C  S  N  T 610        620        630        640        650
TTTTGATGGGCCTGGGAGAGTTCTGGCCCATGCCGACATCCCAGAGCTGG
   F  D  G  P  G  R  V  L  A  H  A  D  I  P  E  L  G 660        670        680        690        700
GCAGTGTGCACTTCGACGAAGACGAGTTCTGGACTGAGGGGACCTACCGT
   S  V  H  F  D  E  D  E  F  W  T  E  G  T  Y  R 710        720        730        740        750
GGGGTGAACCTGCGCATCATTGCAGCCCATGAAGTGGGCCATGCTCTGGG
  G  V  N  L  R  I  I  A  A  H  E  V  G  H  A  L  G 760        770        780        790        800
GCTTGGGCACTCCCGATATTCCCAGGCCCTCATGGCCCCAGTCTACGAGG
   L  G  H  S  R  Y  S  Q  A  L  M  A  P  V  Y  E  G 810        820        830        840        850
GCTACCGGCCCCACTTTAAGCTGCACCCAGATGATGTGGCAGGGATCCAG
   Y  R  P  H  F  K  L  H  P  D  D  V  A  G  I  Q
```

FIG. 4B

```
       860        870        880        890        900
GCTCTCTATGGCAAGAAGAGTCCAGTGATAAGGGATGAGGAAGAAGAAGA
  A  L  Y  G  K  K  S  P  V  I  R  D  E  E  E  E 910        920        930        940        950
GACAGAGCTGCCCACTGTGCCCCCAGTGCCCACAGAACCCAGTCCCATGC
   T  E  L  P  T  V  P  P  V  P  T  E  P  S  P  M  P 960        970        980        990       1000
CAGACCCTTGCAGTAGTGAACTGGATGCCATGATGCTGGGGCCCCGTGGG
   D  P  C  S  S  E  L  D  A  M  M  L  G  P  R  G 1010       1020       1030       1040       1050
AAGACCTATGCTTTCAAGGGGGACTATGTGTGGACTGTATCAGATTCAGG
  K  T  Y  A  F  K  G  D  Y  V  W  T  V  S  D  S  G 1060       1070       1080       1090       1000
ACCGGGCCCCTTGTTCCGAGTGTCTGCCCTTTGGGAGGGGCTCCCCGGAA
   P  G  P  L  F  R  V  S  A  L  W  E  G  L  P  G  N 1110       1120       1130       1140       1150
ACCTGGATGCTGCTGTCTACTCGCCTCGAACACAATGGATTCACTTCTTT
   L  D  A  A  V  Y  S  P  R  T  Q  W  I  H  F  F 1160       1170       1180       1190       1200
AAGGGAGACAAGGTGTGGCGCTACATTAATTTCAAGATGTCTCCTGGCTT
   K  G  D  K  V  W  R  Y  I  N  F  K  M  S  P  G  F 1210       1220       1230       1240       1250
CCCCAAGAAGCTGAATAGGGTAGAACCTAACCTGGATGCAGCTCTCTATT
   P  K  K  L  N  R  V  E  P  N  L  D  A  A  L  Y  W
```

FIG. 4C

```
       1260      1270      1280      1290      1300
GGCCTCTCAACCAAAAGGTGTTCCTCTTTAAGGGCTCCGGGTACTGGCAG
  P  L  N  Q  K  V  F  L  F  K  G  S  G  Y  W  Q 1310      1320      1330      1340      1350
TGGGACGAGCTAGCCCGAACTGACTTCAGCAGCTACCCCAAACCAATCAA
  W  D  E  L  A  R  T  D  F  S  S  Y  P  K  P  I  K 1360      1370      1380      1390      1400
GGGTTTGTTTACGGGAGTGCCAAACCAGCCCTCGGCTGCTATGAGTTGGC
  G  L  F  T  G  V  P  N  Q  P  S  A  A  M  S  W  Q 1410      1420      1430      1440      1450
AAGATGGCCGAGTCTACTTCTTCAAGGGCAAAGTCTACTGGCGCCTCAAC
  D  G  R  V  Y  F  F  K  G  K  V  Y  W  R  L  N 1460      1470      1480      1490      1500
CAGCAGCTTCGAGTAGAGAAAGGCTATCCCAGAAATATTTCCCACAACTG
  Q  Q  L  R  V  E  K  G  Y  P  R  N  I  S  H  N  W 1510      1520      1530      1540      1550
GATGCACTGTCGTCCCCGGACTATAGACACTACCCCATCAGGTGGGAATA
  M  H  C  R  P  R  T  I  D  T  T  P  S  G  N  T 1560      1570      1580      1590      1600
CCACTCCCTCAGGTACGGGCATAACCTTGGATACCACTCTCTCAGCCACA
  T  P  S  G  T  G  I  T  L  D  T  T  L  S  A  T 1610      1620      1630      1640      1650
GAAACCACGTTTGAATACTGACTGCTCACCCACAGACACAATCTTGGACA
  E  T  T  F  E  Y  *
       1660      1670      1680      1690      1700
TTAACCCCTGAGGCTCCACCACCCACCCTTTCATTTCCCCCCCAGAAGCC
```

FIG. 4D

```
       1710      1720      1730      1740      1750
TAAGGCCTAATAGCTGAATGAAATACCTGTCTGCTCAGTAGAACCTTGCA 1760      1770      1780      1790      1800
GGTGCTGTAGCAGGCGCAAGACCGTAGATTTCAGGCTTTTAACACTTCCA 1810      1820      1830      1840      1850
ACTCCAGCCACCACTTTCCTGTGCATTTTCACTCCTGAGAAGTGCTCCCC 1860      1870      1880      1890      1900
TAACTCAGATCCCCTAACTTAGATTTGGCCCCAACTCCATTTCCTGTCT 1910      1920      1930      1940      1950
GTCTTAGACAGCCCTTCCAACTGTGTCATCTCTTCTCTGGAGGTCAATGG 1960      1970      1980      1990      2000
TGGAGGGAGATGCCTGGGTCCTGTTCTTCCTACATAAAATGCAAGAAAAC 2010      2020      2030      2040      2050
AGCATGGCCAGTAAACTGAGCAAGGGCCTTGGAATCCTTGAGAATCACAT 2060      2070      2080      2090      2100
TTATGTGCTTATGATTACGGGCAAGCTAATTAACCTTGTTGAATCTCAGA 2110      2120      2130      2140      2150
TTCCCCATTTGCAACATTAGGTTAAGACCAGTACTGCAGGATTGTTGCAC 2160      2170      2180      2190      2200
TAAATGAAATACTGTATGTGAAGTGCCTGGCACAGTGTCTGGTACATTTG 2210      2220      2230      2240      2250
TGTTTAATAAAGCTAACTCCATGTTCATAAGAGAGGACTGAAAAAAAAA 2260      2270
AAAAAAAAAAAAA
```

FIG. 4E

```
                10        20        30        40        50
       GTCCCCTGCCTAGCCCTGTTCCTCCAAGTTCCCAGAAGTCTCAGGTCAGA 60        70        80        90       100
       GGGCTCAGGCAGCTTCTGGAACTCTTGTCTGCTGGGACCATGGACTGGCA
                                                   MetAspTrpGln 110       120       130       140       150
       GCAGCTGTGGCTGGCCTTCTTACTTCCTGTGACAGTCTCAGGCCGGGCTC
        GlnLeuTrpLeuAlaPheLeuLeuProValThrValSerGlyArgAlaLeu 160       170       180       190       200
       TGGGGCCTGCAGAGAAGGAGGCGGTGGTGGATTACCTGTTGCAGTATGGG
         GlyProAlaGluLysGluAlaValValAspTyrLeuLeuGlnTyrGly 210       220       230       240       250
       TATCTACAGAAACCTCTGGAAGGAGCTGATGACTTCAGGCTAGAAGATAT
        TryLeuGlnLysProLeuGluGlyAlaAspAspPheArgLeuGluAspIle 260       270       280       290       300
       CACAGAGGCTCTAAGAACTTTCCAGGAAGCATCTGAACTGCCTGTTTCCG
         ThrGluAlaLeuArgThrPheGlnGluAlaSerGluLeuProValSerGly 310       320       330       340       350
       GTCAGATGGATGATGCCACAAGGGCCCGTATGAAGCAGCCCCGTTGTGGC
         GlnMetAspAspAlaThrArgAlaArgMetLysGlnProArgCysGly 360       370       380       390       400
       CTGGAGGATCCTTTCAACCAGAAGACTCTGAAATACCTGCTTCTGGGCCA
        LeuGluAspProPheAsnGlnLysThrLeuLysTyrLeuLeuLeuGlyHis 410       420       430       440       450
       CTGGAGAAAGAAGCACTTGACATTCCGCATCTTGAACGTGCCCTCCACCC
         TrpArgLysLysHisLeuThrPheArgLeuLeuAsnValProSerThrLeu
```

FIG. 6A

```
         460         470        480        490        500
TCTCACCCTCCAGAGTCCGAGCAGCCCTGCATCAAGCCTTTAAGTATTGG
   SerProSerArgValArgAlaAlaLeuHisGlnAlaPheLysTyrTrp 510        520        530        540        550
AGCAATGTAGCCCCCCTGACCTTCCGGGAGGTGAAAGCTGGTTGGGCTGA
SerAsnValAlaProLeuThrPheArgGluValLysAlaGlyTrpAlaAsp 560        570         580       590        600
TATCCGCCTCTCGTTCCATGGCCGCCAAAGCCCATACTGCTCCAACAGCT
IleArgLeuSerPheHisGlyArgGlnSerProTyrCysSerAsnSerPhe 610        620        630        640        650
TTGATGGGCCTGGGAAGGTCCTGGCCCATGCTGACGTCCCAGAGCTTGGC
   AspGlyProGlyLysValLeuAlaHisAlaAspValProGluLeuGly 660        670        680        690        700
AGTGTACACTTCGATAACGATGAATTCTGGACCGAGGGCACCTACCAGGG
   SerValHisPheAspAsnAspGluPheTrpThrGluGlyThrTyrGlnGly 710        720        730        740        750
AGTGAACCTACGCATCATTGCGGCCCATGAGGTGGGCCACGCCCTGGGAC
   ValAsnLeuArgIleIleAlaAlaHisGluValGlyHisAlaLeuGlyLeu 760        770        780        790        800
TTGGGCATTCCCGATATACCCAGGCACTCATGGCGCCTGTTTACGCTGGC
   GlyHisSerArgTyrThrGlnAlaLeuMetAlaProValTyrAlaGly 810        820        830        840        850
TACCAGCCCTACTTCAGGCTGCATCCGGATGATGTGGCAGGGATCCAGGC
   TryGlnProTyrPheArgLeuHisProAspAspValAlaGlyIleGlnAla
```

FIG. 6B

```
       860        870        880        890        900
GCTCTATGGCAAGAGGAGGCCGGAGCCAGAAGATGAGGAGGAAGAGGTGG
  LeuTyrGlyLysArgArgProGluProGluAspGluGluGluValGlu 910        920        930        940        950
AGATGCACACTGTGTCAACAGTGACCACAAAACCCAGTCCCATGCCAAAC
  MetHisThrValSerThrValThrThrLysProSerProMetProAsn 960        970        980        990       1000
CCCTGCAGCAGTGAAGTGGATGCCATGATGCTAGGGCCTCGGGGGAAGAC
  ProCysSerSerGluValAspAlaMetMetLeuGlyProArgGlyLysThr 1010       1020       1030       1040       1050
CTATGCTTTCAAGGGTGACTATGTGTGGACTGTAACAGATTCAGGGCCAG
  TyrAlaPheLysGlyAspTyrValTrpThrValThrAspSerGlyProGly 1060       1070       1080       1090       1100
GGCCCTTGTTCCGAGTGTCTGCCCTTTGGGAGGGGCTTCCTGGAAACCTG
  ProLeuPheArgValSerAlaLeuTrpGluGlyLeuProGlyAsnLeu 1110       1120       1130       1140       1150
GATGCTGCTGTCTACTCTCCCCGGACACAGCGGACTCATTTCTTCAAGGG
  AspAlaAlaValTyrSerProArgThrGlnArgThrHisPhePheLysGly 1160       1170       1180       1190       1200
AAACAAGGTGTGGCGGTATGTGGATTTCAAGTTGTCTCCTGGCTTTCCCA
  AsnLysValTrpArgTyrValAspPheLysLeuSerProGlyPheProMet 1210       1220       1230       1240       1250
TGAAACTCAACAGAGTGGAACCCAACCTAGATGCAGCTCTCTATTGGCCT
  LysLeuAsnArgValGluProAsnLeuAspAlaAlaLeuTyrTrpPro
```

FIG. 6C

```
       1260        1270        1280        1290        1300
GTTAATCAGAAGGTGTTCCTTTTTAAGGGCTCAGGATACTGGCAATGGGA
ValAsnGlnLysValPheLeuPheLysGlySerGlyTyrTrpGlnTrpAsp 1310        1320        1330        1340        1350
TGAACTGACCAGAACTGACCTCAGTCGCTACCCCAAACCAATCAAGGAAC
  GluLeuThrArgThrAspLeuSerArgTyrProLysProIleLysGluLeu 1360        1370        1380        1390        1400
TTTTCACTGGAGTGCCAGACCAACCCTCAGCAGCTATGAGCTGGCAAGAT
   PheThrGlyValProAspGlnProSerAlaAlaMetSerTrpGlnAsp 1410        1420        1430        1440        1450
GGCCAAGTCTACTTCTTCAAGGGCAAAGAGTACTGGCGCCTTAACCAGCA
GlyGlnValTyrPhePheLysGlyLysGluTyrTrpArgLeuAsnGlnGln 1460        1470        1480        1490        1500
ACTTCGAGTGGCAAAGGGCTATCCCAGAAATACGACACACTGGATGCACT
  LeuArgValAlaLysGlyTyrProArgAsnThrThrHisTrpMetHisCys 1510        1520        1530        1540        1550
GTAGTCCTCGGACTCCAGACACTAACTCATTAACTGGGGATGTGACCACT
    SerProArgThrProAspThrAsnSerLeuThrGlyAspValThrThr 1560        1570        1580        1590        1600
CCTGCAACCGTGGAATCAGTCTTGGATGTTCCCTCTGCCACAGACGCTGC
ProAlaThrValGluSerValLeuAspValProSerAlaThrAspAlaAla 1610        1620        1630        1640        1650
CTCCCTCTCATCCTCAGCTAATGTCACCTTGCTAGGGGCCTGAGAACTAG
   SerLeuSerSerSerAlaAsnValThrLeuLeuGlyAla***

1660        1670        1680        1690        1700
TCAGTGTCTGCTCCTTAGGGTTGTGCAGATGGGCACTTGACCTAGTGCCC
```

FIG. 6D

```
         1710       1720       1730       1740       1750
     CTAGATACTCCAATTCTGGATGCCACATTCCAGTGTTCCTAGAAAGTGAC 1760       1770       1780       1790       1800
     TGCTTAATTCTGAGTCATTCCCCAGTCCCCATTTCTTCTTGTCATATGGC 1810       1820       1830       1840       1850
     TGTTTCAAGTGTGACATCTATTTTCTGGTGGAGGGAAATTGTTGATCAGG 1860       1870       1880       1890       1900
     ACCCCCCCCCCCCCCAGGGTCTCTCTACATAGCACTGGCTATGGTTATCG 1910       1920       1930       1940       1950
     GCTATCCTGAAACTGTGTAGTTATGTAGACTAGGCTAACTTGAACTCACA 1960       1970       1980       1990       2000
     GAAACCAACCTGCCTCTGCCTCTGTCCTGAGTGCTGGGATTAAAACGTG 2010       2020       2030       2040       2050
     TGCTACCAAAAAAAAAAAAAAAAAAAAAAAAAAAAAAAAAAAAAAAAAAA
```

FIG. 6E

PROTEINS, THEIR PRODUCTION AND USE

This application is a divisional of U.S. Ser. No. 09/171,545 filed Jul. 26, 1999 which claims the benefit of PCT/JP97/01433 filed Apr. 24, 1997, now U.S. Pat. No. 6,566,116 which in turn claims priority to Japanese application, number 8-104902, filed in Japan on Apr. 25, 1996.

TECHNICAL FIELD

The present invention relates to a novel matrix metalloprotease and a DNA coding for the metalloprotease.

BACKGROUND ART

The extracellular matrix, which is a cell-supporting tissue composed mainly of collagens and proteoglycans, is profoundly involved in such events as cell development, inflammation, and tissue repair. The enzymes known to be associated with the degradation of extracellular matrix are (1) cathepsin D, etc. which belongs to the aspartic proteaseas, (2) cathepsin B, H, L, etc. which belong to the cysteine proteases, (3) plasmin, kallikrein, neutrophil elastase, tryptase, chymase, cathepsin G, etc. which belong to the serine proteases, and (4) metalloproteases are known. Also called matrix metalloproteases, these metalloproteases are known to be playing central roles in the degradation of extracellular matrix.

So far, in humans, 13 kinds of matrix metalloproteases such as collagenases, gelatinases stromelysins, and membrane-type matrix metalloproteases have been cloned and their nucleotide sequences and amino acid sequences have been reported (T. Takino et al., Journal of Biological Chemistry, 270, 23013, 1995; J. M. P. Freije et al., Journal of Biological Chemistry, 269, 16766, 1994; H. Wills et al., European Journal of Biochemistry, 231, 602, 1995). All of these enzymes are zinc-dependent metalloproteases, in which the amino acid sequence of the zinc-binding domain: His-Glu-X-Gly-His-Ser-Leu-Gly-Leu-X-His-Ser is well conserved, and their activities are inhibited by o-phenanthroline. Each of these enzymes is secreted in the latent form which is inactive with a propeptide at the N-terminus of the active enzyme. A conserved domain consisting in the amino acid sequence of Met-Arg-Lys-Pro-Arg-Cys-Gly-Val-Pro-Asp is located near the C-terminal region of the propeptide. This domain is called "cysteine switch", and it controls a protease activity by coordinating the zinc atom at active center with cysteine in the domain. While the latent enzymes are activated upon cleavage of the propeptide, three kinds of inhibitor proteins, named TIMP, have been reported and known to performing strict control of activity. It is also known that, in vitro, the latent enzymes are activated by treatment with trypsin or aminophenylmercuric acetate.

Matrix metalloproteases are not only involved in the degradation of the extracellular matrix such as collagens, gelatins which are denatured collagens, proteoglycans, fibronectins, laminins, elastins, etc. but also are in charge of activation of other matrix metalloproteases and inactivation of protease inhibitors such as α1-protease inhibitor. Furthermore, it is known that these metalloproteases are associated with solubilization of membrane proteins and cell surface proteins such as TNF, Fas ligand, IL-6 receptor, TNF-receptor, etc. and, as a result, modulate the death, differentiation, proliferation inhibition, proliferation and gene expression of cells.

It is known that physiologically matrix metallo protease activities are elevated in ovulation, development and differentiation, osteogenesis, atretic uterus, vascularization, and other events. In morbid states, those metalloprotease activities are elevated in rheumatoid arthritis, osteoarthritis, cancer (metastasis and invasion), peridontitis, corneal ulcer, gastric ulcer, myocardiopathy, aneurysm, otosclerosis, epidermolysis bullosa, premature labor, and atherosclerosis, among other conditions. Conversely, it is known that the enzyme activities are suppressed in fibroid lung, hepatolienal fibrosis, hepatocirrhosis, osteopetrosis, etc. Recently the fourth membrane-type matrix metalloprotease has been cloned (X. S. Puente et al., Cancer Research, 56, 944, 1996), suggesting the likelihood that there exist still other novel matrix metalloproteases.

Any novel matrix metalloproteases of human origin make it possible to develop new drugs which inhibit or stimulate the activity of the metalloprotease and are useful for the prevention and treatment of various matrix metalloprotease-associated morbidities, such as rheumatoid arthritis, and osteoarthritis. Therefore, in the technological area to which the present invention pertains, there has been a standing need for isolating novel human matrix metalloproteases and developing a method for high production of the proteins.

The inventors of the present invention have made extensive research for solving the above problems and succeeded in cloning cDNAs each having a novel nucleotide sequence from human liver-derived and rat liver-derived cDNA libraries. They have found that the proteins encoded by these cDNAs are matrix metalloproteases. The present inventors have made further investigations based on these findings, and accomplished the present invention.

DISCLOSURE OF INVENTION

The present invention provides:

(1) A protein comprising an amino acid sequence represented by SEQ ID NO:1 or a substantially equivalent thereto, or a salt thereof, (2) The protein according to claim 1, which comprises an amino acid sequence represented by SEQ ID NO:2, (3) The protein according to (1), which is a metalloprotease, (4) A partial peptide of the protein according to (1), or a salt thereof, which shows the activity of the protein according to (1), (5) An isolated DNA which contains a DNA comprising a nucleotide sequence coding for a protein according to (1), (6) The DNA according to (5), which comprises a nucleotide sequence represented by SEQ ID NO:4, (7) The DNA according to (5), which comprises a nucleotide sequence represented by SEQ ID NO:8, (8) A recombinant vector comprising the DNA according to (5), (9) A transformant carrying the recombinant vector according to (8),

(10) A process for producing a protein or a salt thereof according to (1), which comprises culturing a transformant according to (9) under conditions suitable to express the protein,

(11) A pharmaceutical composition which comprises the protein according to (1) or the partial peptide according to (4),

(12) The pharmaceutical composition according to (11) which is a therapeutic or prophylactic composition for diabetic nephropathy, glomerulonephritis, pulmonary fibrosis, hepatolienal fibrosis, hepatocirrhosis, osteopetrosis or herniated disk,

(13) A pharmaceutical composition which comprises the DNA according to (5),

(14) The pharmaceutical composition according to (13) which is a therapeutic or prophylactic composition for diabetic nephropathy, glomerulonephritis, pulmonary fibrosis, hepatolienal fibrosis, hepatocirrhosis, osteopetrosis or herniated disk,

(15) An antibody against the protein according to (1) or the partial peptide according to (4),

(16) A method for screening for a compound which activates or inhibits a proteolytic activity of the protein according to (1) or the partial peptide according to (4), which comprises measuring and comparing a proteolytic activity of the protein according to (1) or the partial peptide according to (4), in case of (i) a substrate is contacted with the protein according to (1) or the partial peptide according to (4) and (ii) a substrate and a test compound are contacted with the protein according to (1) or the partial peptide according to (4),

(17) A kit for screening for a compound which activates or inhibits a proteolytic activity of the protein according to (1) or the partial peptide according to (4), which comprises the protein according to (1) or the partial peptide according to (4),

(18) A compound which activates or inhibits a proteolytic activity of the protein according to (1) or the partial peptide according to (4), which is identified by the screening method according to (16) or the kit according to (17),

(19) A pharmaceutical composition which comprises the compound which inhibits a proteolytic activity of the protein according to (1) or the partial peptide according to (4), which is identified by the screening method according to (16) or the kit according to (17),

(20) A method for treating or preventing diabetic nephropathy, glomerulonephritis, pulmonary fibrosis, hepatolienal fibrosis, hepatocirrhosis, osteopetrosis or herniated disk in a mammal, which comprises administering an effective amount of the protein according to (1) or the partial peptide according to (4),

(21) Use of the protein according to (1) or the partial peptide according to (4) for production of a therapeutic or prophylactic composition for diabetic nephropathy, glomerulonephritis, pulmonary fibrosis, hepatolienal fibrosis, hepatocirrhosis, osteopetrosis or herniated disk,

(22) A method for treating or preventing diabetic nephropathy, glomerulonephritis, pulmonary fibrosis, hepatolienal fibrosis, hepatocirrhosis, osteopetrosis or herniated disk in a mammal, which comprises administering an effective amount of the DNA according to (5) to the mammal, and

(23) Use of the DNA according to (5) for production of a therapeutic or prophylactic composition for diabetic nephropathy, glomerulonephritis, pulmonary fibrosis, hepatolienal fibrosis, hepatocirrhosis, osteopetrosis or herniated disk.

Moreover, the present invention provides:

(24) The partial peptide according to (4), which comprises an amino acid sequence represented by any one of SEQ ID NO:3 to SEQ ID NO:6 or a substantial equivalent thereto,

(25) An isolated DNA which hybridizes under highstringent condition to a DNA comprising a nucleotide sequence represented by SEQ ID NO:7 or SEQ ID NO:8,

(26) A recombinant vector comprising the DNA according to (25),

(27) A transformant carrying the recombinant vector according to (26),

(28) A process for producing a protein which is encoded by the DNA according to (25) or a salt thereof comprising culturing a transformant according to (27) under conditions suitable to express the protein,

(29) A protein produced by the process according to (28),

(30) The pharmaceutical composition according to (19) which is a therapeutic or prophylactic composition for wound, rheumatoid arthritis, osteoarthritis, cancer (metasrasis and invasion), periontitis, corneal ulcer, gastric ulcer, myocardiopathy, aneurysm, otosclerosis, epidermolysis bullosa, premature delivery, atherosclerosis, septemia, multiple (disseminated) sclerosis, cachexia, hypercalcemia, leulemia, lymphoma, diabetes, systemic lupus erythematosus, asthma, allergic rhinitis, atopic dermatitis, trauma, burn, acute pancreatitis, ischemia-reperfusion syndrome, myocardial infarction, congrestive heart failure, organ transplantation or graft-vs.-host disease (GVHD),

(31) A pharmaceutical composition which comprises the compound which activates a proteolytic activity of the protein according to (1) or the partial peptide according to (4), or a salt thereof, which is identified by the screening method according to (16) or the kit according to (17),

(32) The pharmaceutical composition according to (31) which is a therapeutic or prophylactic composition for diabetic nephropathy, glomerulonephritis, pulmonary fibrosis, hepatolienal fibrosis, hepatocirrhosis, osteopetrosis or herniated disk,

(33) A method of quantitative determination of the protein according to (1) or the partial peptide according to (4) in a test liquid sample, which comprises (a) competitively reacting the test liquid sample and a labeled protein according to (1) or partial peptide according to (4) with the antibody according to (15), and (b) measuring the ratio of the labeled protein according to (1) or partial peptide according to (4) which binds to the antibody, and

(34) A method of quantitative determination of the protein according to (1) or the partial peptide according to (4) in a test liquid sample, which comprises (a) reacting the test liquid sample with the antibody according to (15) immobilized on an insoluble carrier and a labeled antibody according to (15) simultaneously or continuously, and (b) measuring the activity of the labeling agent on the insoluble carrier.

The protein comprising the amino acid sequence represented by SEQ ID NO:1 (FIG. 1) or a substantial equivalent thereto of the present invention (hereinafter referred to as the protein of the present invention) may be (1) a protein derived from cells of human and other warm-blooded animals (e.g. guinea pig, rat, mouse, chicken, rabbit, swine, sheep, bovine, monkey, etc.) such as liver cell, splenocytes, nerve cell, glia cell, B cell, bone marrow cell, mesangial cell, Langerhans' cell, epidermic cell, epithelial cell, endothelial cell, fibroblast, fibrocyte, myocyte, fat cell, immune cell (e.g. macrophage, T cell, B cell, natural killer cell, mast cell, neutrophil, basophil, eosinophil, monocyte), megakaryocyte, synovial cell, chondrocyte, bone cell, osteoblast, osteoclast, mammary gland cell, hepatocyte, interstitial cell, etc., the corresponding precursor cells, stem cells, cancer cells, etc., or any tissues where such cells are present, such as brain or any of its regions (e.g. olfactory bulb, amygdaloid nucleus, basal ganglia, hippocampus, thalamus, hypothalamus, cerebral cortex, medulla oblongata, cerebellum, etc.), spinal cord, hypophysis, stomach, pancreas, kidney, liver, gonad, thyroid, gallbladder, bone marrow, adrenal gland, skin, muscle, lung, gastrointestinal tract (e.g. large intestine and small intestine), blood vessel, heart, thymus, spleen, submandibular gland, peripheral blood, prostate, testis, ovary, placenta, uterus, bone, joint, skeletal muscle, etc., (2) a protein derived from cultured human cell lines (e.g. MEL, M1, CTLL-2, HT-2, WEHI-3, HL-60, JOSK-1, K562, ML-1, MOLT-3, MOLT-4, MOLT-10, CCRF-CEM, TALL-1, Jurkat, CCRT-HSB-2, KE-37, SKW-3, HUT-78, HUT-102, H9, U937, THP-1, HEL, JK-1, CMK, KO-812, MEG-01, etc.), or (3) a synthetic protein.

Examples of the substantially equivalent amino acid sequence to the amino acid sequence represented by SEQ ID NO:1 are an amino acid sequence of not less than about 50%, preferably not less than about 60%, more preferably not less than about 70%, further more preferably not less than about 80%, for still better result, not less than about 90%, best example, not less than about 95% identity to the amino acid sequence represented by SEQ ID NO:1 and so on. More preferable examples are an amino acid sequence of not less than about 50%, preferably not less than about 60%, more preferably not less than about 70%, further more preferably not less than about 80%, for still better result, not less than about 90%, best example, not less than about 95% identity to the amino acid sequence represented by SEQ ID NO:1, which comprises at least an amino acid sequence represented by SEQ ID NO:3 (FIG. 2) or SEQ ID NO:4 (FIG. 3), and so on.

Examples of the substantially equivalent amino acid sequence to the amino acid sequence represented by SEQ ID NO:1 are an amino acid sequence represented by SEQ ID NO:2, and so on.

Examples of the protein comprising a substantially equivalent to the amino acid sequence represented by SEQ ID NO:1 are a protein which comprises a substantially equivalent amino acid sequence to the amino acid sequence represented by SEQ ID NO:1 and has a substantially equivalent activity to the protein comprising the amino acid sequence represented by SEQ ID NO:1, and so on.

More preferable examples of the protein are a protein comprising an amino acid sequence represented by SEQ ID NO:2, and so on.

Examples of the substantially equivalent activity are a proteolytic activity (e.g. activity of proteases such as proteinases, peptidases, etc.) and so on. The term "substantially equivalent" means that the nature of these activities are physiologically chemically or phramacologically equivalent. Therefore, it is preferred that the strength of activities such as a proteolytic activity is equivalent (e.g. about 0.01 to 100 times, preferably about 0.5 to 20 times, more preferably about 0.5 to 2 times), and it is allowable that even differences among grades such as the strength of these activities and molecular weight of the protein are present.

Activities such as a proteolytic activity may be measured by per se known methods. For example, the proteolytic activity may be measured by the method for screening as mentioned below.

The proteins of the present invention include muteins such as proteins comprising (1) an amino acid sequence wherein 1 or more amino acid residues (for example 1 to 30, preferably 1 to 10, more preferably a few (1 to 5) amino acid residues) are deleted from the amino acid sequence represented by SEQ ID NO:1, (2) an amino acid sequence wherein 1 or more amino acid residues (for example 1 to 30, preferable 1 to 10, more preferable a few (1 to 5) amino acid residues) are added to the amino acid sequence represented by SEQ ID NO:1, (3) an amino acid sequence wherein 1 or more than acid residues (for example 1 to 30, preferably 1 to 10, more preferably a few (1 to 5) amino acid residues) in the amino acid sequence represented by SEQ ID NO:1 are substituted with 1 or more amino acid residues (for example 1 to 30, preferably 1 to 10, more preferably a few (1 to 5) amino acid residues), or (4) combinations thereof.

When the amino acid sequence of the proteins are deleted or substituted as mentioned above, examples of the positions of deletion or substitution are, for example, (1) other than 98th to 508th amino acid sequence of the amino acid sequence represented by SEQ ID NO:1 (other than an amino acid sequence represented by SEQ ID NO:3), more preferably, other than 93rd to 508th amino acid sequence of the amino acid sequence represented by SEQ ID NO:1 (an amino acid sequence represented by SEQ ID NO:4), or (2) other than 99th to 517th amino acid sequence of the amino acid sequence represented by SEQ ID NO:2 (other than an amino acid sequence represented by SEQ ID NO:5), more preferably, other than 94th to 517th amino acid sequence of the amino acid sequence represented by SEQ ID NO:2 (other than an amino acid sequence represented by SEQ ID NO:6). Other preferable examples of the positions of deletion or substitution are other than a common sequence of the amino acid sequence represented by SEQ ID NO:1 and the amino acid sequence represented by SEQ ID NO:2, and more preferable examples are, for example, other than 212nd to 225th amino acid sequence of the amino acid sequence represented by SEQ ID NO:1 (that is, other than 213rd to 226th amino acid sequence of the amino acid sequence represented by SEQ ID NO:2).

Throughout this specification, proteins are represented in accordance with the conventions for description of peptides, that is the N-terminus (amino terminus) at left and the C-terminus (carboxyl terminus) at right. The protein of the present invention including the protein containing the amino acid sequence of SEQ ID NO:1 is usually in the carboxyl (—COOH) or carboxylate (—COO⁻) form at the C-terminus but may be in the amide (—CONH$_2$) or ester (—COOR) form.

R in the ester residue includes a $C_{1-6}$ alkyl group (e.g. methyl, ethyl, n-propyl, isopropyl, n-butyl, etc., a $C_{3-8}$ cycloalkyl group (e.g. cyclopentyl, cyclohexyl, etc.), a $C_{6-12}$ aryl group (e.g. phenyl, α-naphthyl, etc.), a $C_{7-14}$ aralkyl group such as a phenyl-$C_{1-2}$ alkyl group (e.g. benzyl, phenethyl, etc.) and α-naphthyl-$C_{1-2}$ alkyl, (e.g. α-naphthylmethyl, etc.), as well as pivaloyloxymethyl which is universally used for the production of esters for oral administration.

When the protein of the present invention has a carboxyl (or carboxylate) function in any position other than the C-terminus, the corresponding carboxamide or ester form is also included in the scope of the invention. The ester mentioned just above may be any of the esters mentioned for the C-terminal carboxyl function.

Furthermore, the protein of the present invention includes (1) the protein in which the N-terminal Met has been protected with a protective group (e.g. $C_{1-6}$ acyl such as formyl or $C_{1-5}$ alkyl-carbonyl such as acetyl, etc.), (2) the protein in which the N-terminal side of Glu has been cleaved in vivo to form pyroglutamic acid, (3) the protein in which the side chain of any relevant constituent amino acid (e.g. OH, COOH, NH$_2$, SH) has been protected by any protective group (e.g. $C_{1-6}$ acyl group such as formyl or $C_{1-5}$ alkyl-carbonyl group such as acetyl, etc.), and (4) the complex protein such as glycoproteins available upon attachment of sugar chains.

Preferable Examples of the proteins of the present invention are human metalloproteases such as a human liver-derived metalloprotease comprising an amino acid sequence represented by SEQ ID NO:1 (FIG. 1), rat metalloproteases such as a rat liver-derived metalloprotease comprising an amino acid sequence represented by SEQ ID NO:2 (FIG. 6).

Examples of the partial peptide of the present invention are any partial peptides of the protein of the present invention as mentioned above which have a proteolytic activity. For example, the partial peptides include peptides comprising at least not less than about 20, preferably not less than about 50, more preferably not less than about 70, for still better result, not less than about 100, best result, not less than 200 amino acid residues of the amino acid sequence of the proteins of the present invention.

Preferable examples of the partial peptide of the present invention are (1) a peptide which comprises an amino acid sequence represented by SEQ ID NO:3 or SEQ ID NO:4, or a substantially equivalent thereto and has a substantially equivalent activity to the protein comprising the amino acid sequence represented by SEQ ID NO:1, (2) a peptide which comprises an amino acid sequence represented by SEQ ID NO:5 or SEQ ID NO:6, or a substantially equivalent thereto and has a substantially equivalent activity to the protein comprising the amino acid sequence represented by SEQ ID NO:2.

Examples of the substantially equivalent amino acid sequence to the amino acid sequence represented by SEQ ID NO:3 or SEQ ID NO:4 are an amino acid sequence of not less than about 50%, preferably not less than about 60%, more preferably not less than about 70%, further more preferably not less than about 80%, for still better result, not less than about 90%, best example, not less than about 95% identity to the amino acid sequence represented by SEQ ID NO:3 or SEQ ID NO:4.

Examples of the substantially equivalent amino acid sequence to the amino acid sequence represented by SEQ ID NO:5 or SEQ ID NO:6 are an amino acid sequence of not less than about 50%, preferably not less than about 60%, more preferably not less than about 70%, further more preferably not less than about 80%, for still better result, not less than about 90%, best example, not less than about 95% identity to the amino acid sequence represented by SEQ ID NO:5 or SEQ ID NO:6.

The amino acid sequence represented by SEQ ID NO:3 shows an amino acid sequence from $^{98}$Tyr to $^{508}$Tyr of the amino acid sequence represented by SEQ ID NO:1, and the amino acid sequence represented by SEQ ID NO:4 shows an amino acid sequence from $^{93}$Gln to $^{508}$Tyr of the amino acid sequence represented by SEQ ID NO:1. The both amino acid sequences show amino acid sequences of catalytic domain of the protein of the present invention, and show amino acid sequence of the mature protein of the protein of the present invention comprising the amino acid sequence represented by SEQ ID NO:1.

The amino acid sequence represented by SEQ ID NO:5 shows an amino acid sequence from $^{99}$Tyr to $^{517}$Tyr of the amino acid sequence represented by SEQ ID NO:12, and the amino acid sequence represented by SEQ ID NO:6 shows an amino acid sequence from $^{94}$Gln to $^{517}$Tyr of the amino acid sequence represented by SEQ ID NO:12. The both amino acid sequences show amino acid sequences of catalytic domain of the protein of the present invention, and show amino acid sequence of the mature protein of the protein of the present invention comprising the amino acid sequence represented by SEQ ID NO:2.

The protein of the present invention is expressed as the protein comprising the amino acid sequence represented by SEQ ID NO:1, and is cleaved in vivo at the position of 1st to 97th or 1st to 92nd of the amino acid sequence represented by SEQ ID NO:1. And the peptide comprising 98th to 508th amino acid sequence (SEQ ID NO:3, FIG. 2) or 93rd to 508th amino acid sequence (SEQ ID NO:4, FIG. 3) of the amino acid sequence represented by SEQ ID NO:1, etc. show a proteolytic activity, etc. as a mature protein or active protein.

The protein of the present invention is expressed as the protein comprising the amino acid sequence represented by SEQ ID NO:2, and is cleaved in vivo at the position of 1st to 98th or 1st to 93rd of the amino acid sequence represented by SEQ ID NO:2. And the peptide comprising 98th to 508th amino acid sequence (SEQ ID NO:5) or 94th to 517th amino acid sequence (SEQ ID NO:6) of the amino acid sequence represented by SEQ ID NO:2, etc. show a proteolytic activity, etc. as a mature protein or active protein.

The term "substantially equivalent activity" has the same meaning as defined above. The "substantially equivalent activity" can be measured by the same method as mentioned above.

The partial peptide of the present invention may include peptides such as peptide comprising (1) an amino acid sequence wherein 1 or more amino acid residues (for example 1 to 30, preferably 1 to 10, more preferably a few (1 to 5) amino acid residues) are deleted from the amino acid sequence represented by SEQ ID NO:3 or SEQ ID NO:4, (2) an amino acid sequence wherein 1 or more amino acid residues (for example 1 to 30, preferable 1 to 10, more preferable a few (1 to 5) amino acid residues) are added to the amino acid sequence represented by SEQ ID NO:3 or SEQ ID NO:4, (3) an amino acid sequence wherein 1 or more amino acid residues (for example 1 to 30, preferably 1 to 10, more preferably a few (1 to 5) amino acid residues) in the amino acid sequence represented by SEQ ID NO:3 or SEQ ID NO:4 are substituted with 1 or more amino acid residues (for example 1 to 30, preferably 1 to 10, more preferably a few (1 to 5) amino acid residues), or (4) combinations thereof.

Other partial peptide of the present invention may include peptides such as peptide comprising (1) an amino acid sequence wherein 1 or more amino acid residues (for example 1 to 30, preferably 1 to 10, more preferably a few (1 to 5) amino acid residues) are deleted from the amino acid sequence represented by SEQ ID NO:5 or SEQ ID NO:6, (2) an amino acid sequence wherein 1 or more amino acid residues (for example 1 to 30, preferable 1 to 10, more preferable a few (1 to 5) amino acid residues) are added to the amino acid sequence represented by SEQ ID NO:5 or SEQ ID NO:6, (3) an amino acid sequence wherein 1 or more amino acid residues (for example 1 to 30, preferably 1 to 10, more preferably a few (1 to 5) amino acid residues) in the amino acid sequence represented by SEQ ID NO:5 or SEQ ID NO:6 are substituted with 1 or more amino acid residues (for example 1 to 30, preferably 1 to 10, more preferably a few (1 to 5) amino acid residues), or (4) combinations thereof.

The peptide of the present invention is usually in the carboxyl (—COOH) or carboxylate (—COO⁻) form at the C-terminus, but may instead be in the amide (—CONH$_2$) or ester (—COOR) form as same as the protein of the present invention as mentioned above.

Furthermore, the partial peptide of the present invention includes (1) the peptide in which the N-terminal Met has been protected with a protective group, (2) the peptide in which the N-terminal side of Glu has been cleaved in vivo to form pyroglutamic acid, (3) the peptide in which the side chain or any relevant constituent amino acid has been protected by any protective group, and (4) the complex peptide such as glycoproteins available upon attachment of sugar chains as same as the protein of the present invention as mentioned above.

The specific examples of the partial peptide of the present invention are a peptide comprising an amino acid sequence represented by SEQ ID NO:3 (FIG. 2) or SEQ ID NO:4 (FIG. 3), a peptide comprising an amino acid sequence represented by SEQ ID NO:5 or SEQ ID NO:6, and so on.

The salt of the protein or the partial peptide of the present invention includes salts with physiologically acceptable bases, e.g. alkali metals or acids such as organic or inorganic acids, and is preferably a physiologically acceptable acid addition salt. Examples of such salts are salts thereof with inorganic acids (e.g. hydrochloric acid, phosphoric acid, hydrobromic acid or sulfuric acid, etc.) and salts thereof with organic acids (e.g. acetic acid, formic acid, propionic acid, fumaric acid, maleic acid, succinic acid, tartaric acid, citric acid, malic acid, oxalic acid, benzoic acid, methanesulfonic acid or benzenesulfonic acid, etc.)

The protein or a salt thereof of the present invention can be produced from the tissues or cells of human or other warm-blooded animals by per se known purification technology or, as described hereinafter, by culturing a transformant carrying a DNA encoding the protein. It can also be produced in accordance with the procedures for peptide synthesis which are described hereinafter.

When the protein of the present invention is produced from the tissues or cells of human or other warm-blooded animals, the tissues or cells of human or other warm-blood animals are homogenized and the protein of the present invention is extracted by an acid, etc. The protein can be purified and isolated from the extracted solution by a combination of chromatography such as reverse phase chromatography, ion exchange chromatography and so on.

For the synthesis of the protein of the present invention, a partial peptide thereof or their salts, or their amides form, any of commercial resins available for protein synthesis can be employed. Among such resins are chloromethyl resin, hydroxymethyl resin, benzhydrylamino resin, aminomethyl resin, 4-benzyloxybenzyl alcohol resin, 4-methylbenzhydrylamino resin, PAM resin, 4-hydroxymethyl-methylphenylacetamidomethyl resin, polyacrylamide resin, 4-(2',4'-dimethoxyphenyl-hydroxymethyl)phenoxy resin, and 4-(2',4'-dimethoxyphenyl-Fmoc-aminoethyl)phenoxy resin. Using such a resin, amino acids which may be beforehand protected at side-chain functional groups in a suitable manner can be serially condensed with the a-amino group in the order corresponding to the amino acid sequence of the objective protein by various condensation techniques which are per se known. After completion of the final condensation reaction, the protein is separated from the resin and the protective groups are removed. Then, in highly diluted solution, the intramolecular disulfide-forming reaction is carried out to provide the objective proteins or amides thereof.

Referring to the above condensation of protected amino acids, various activating agents known to be useful for protein synthesis can be utilized, and carbodiimide reagents are especially preferred. The carbodiimide reagents include are DCC, N,N'-diisopropylcarbodiimide, and N-ethyl-N'-(3-dimethylaminoprolyl)carbodiimide and so on. For activation by these reagents, the protected amino acid and a racemization inhibitor (e.g. HOBt, HOOBt, etc.) can be directly added to the resin, or the protected amino acid can be activated beforehand in the form of symmetric acid anhydride, HOBt ester or HOOBt ester and, then, added to the resin.

The solvent used for the above-mentioned activation of protected amino acids or the conjugation thereof to the resin can be optionally selected from among the solvents known to be useful for protein condensation reactions. Examples of the solvent are acid amides (e.g. N,N-dimethylformamide, N,N-dimethylacetamide, N-methylpyrrolidone, etc.), halogenated hydrocarbons (e.g. methylene chloride, chloroform, etc.), alcohols (e.g. trifluoroethanol, sulfoxides (e.g. dimethyl sulfoxide, etc.), ethers is (e.g. pyridine, dioxane, tetrahydrofuran, etc.), nitrites (e.g. acetonitrile, propionitrile, etc.), esters (e.g. methyl acetate, ethyl acetate, etc.), and suitable mixtures of these solvents. The reaction temperature can be selected from the range known to be useful for protein-forming reactions, usually the range of about −20° C. to about 50° C. The activated amino acid derivative is generally used in a 1.5 to 4-fold excess. When the condensation is found insufficient by ninhydrin assay, the reaction can be repeated to make the sufficient condensation thorough. When sufficient condensation can not be achieved by repeated reaction, an unreacted amino acid can be acetylated by using acetic anhydride or acetylimidazole so as not to effect a subsequent reaction.

The protective groups for protecting the amino group of the starting compound include Z, Boc, t-pentyloxycarbonyl, isobornyloxycarbonyl, 4-methoxy-benzyloxycarbonyl, Cl-Z, Br-Z, adamantyloxycarbonyl, trifluoroacetyl, phthaloyl, formyl, 2-nitrophenylsulfenyl, diphenylphosphinothioyl, Fmoc, and so on.

The carboxyl group can be protected in the form of, for example, an alkyl ester (e.g. straight-chain, branched, or cyclic alkyl esters such as methyl, ethyl, propyl, butyl, t-butyl, cyclopentyl, cyclohexyl, cycloheptyl, cyclooctyl, 2-adamantyl, and so on), an aralkyl ester (e.g. benzyl, 4-nitrobenzyl, 4-methoxybenzyl, 4-chlorobenzyl, benzhydryl, and so on), phenacyl ester, benzyloxycarbonylhydrazide, t-butoxycarbonylhydrazide or tritylhydrazide.

The hydroxyl group of serine can be protected in the form of an ester or an ether. The group suitable for esterification includes carboxylic acid-derived acyl groups such as a lower ($C_{1-6}$) alkanoyl group (e.g. acetyl, etc.), an aroyl group (e.g. benzoyl, etc.), a benzyloxycarbonyl, an ethoxycarbonyl group and so on. The group suitable for etherification includes a benzyl group, a tetrahydropyranyl group, a t-butyl group and so on.

The protective group used for protecting the phenolic hydroxyl group of tyrosine includes Bzl, $Cl_2$-Bzl, 2-nitrobenzyl, Br-Z, t-butyl and so on.

The protective group for the imidazole group of histidine includes Tos, 4-methoxy-2,3,6-trimethylbenzenesulfonyl, DNP, benzyloxymethyl, Bum, Boc, Trt, Fmoc and so on.

The starting compound with activated carboxyl groups includes the corresponding acid anhydride, azide, and active ester (e.g. esters with alcohols such as pentachlorophenol, 2,4,5-trichlorophenol, 2,4-dinitrophenol, cyanomethyl alcohol, p-nitrophenol, HONB, N-hydroxysuccinimide, N-hydroxyphthalimide, HOBt, etc.). The starting compound with activated amino groups includes the corresponding phosphorylamide.

The method for removal of such protective groups includes catalytic reduction in a hydrogen stream in the presence of a catalyst (e.g. Pd black or Pd-on-carbon), acid treatment with anhydrous hydrogen fluoride, methanesulfonic acid, trifluoromethanesulfonic acid, trifluoroacetic acid or a mixture thereof, treatment with a base such as diisopropylethylamine, triethylamine, piperidine, piperazine or the like, and reduction with sodium metal in liquid ammonia. The above deprotection by treatment with acid is generally conducted at a temperature of about −20° C. to 40°

C. This acid treatment can be carried out advantageously in the presence of a cation acceptor such as anisole, phenol, thioanisole, m-cresol, p-cresol, dimethyl sulfide, 1,4-butanedithiol, 1,2-ethanedithiol, or the like. The 2,4-dinitrophenyl group used for protecting the imidazole group of histidine can be removed by treatment with thiophenol, and the formyl group used for protecting the indole group of tryptophan can be removed not only by said acid treatment in the presence of 1,2-ethanedithiol, 1,4-butanedithiol or the like as described hereinbefore, but also by alkali treatment with diluted sodium hydroxide solution, diluted liquid ammonia, or the like.

The method for protecting any functional group that should not take part in the contemplated reaction, the protective group to be used for such protection, the method for eliminating the protective group, and the method for activating the functional group to be involved in the contemplated reaction can all be optionally selected from among the known methods and groups.

An alternative method for providing the protein in amide form typically comprises protecting the α-carboxyl group of the C-terminal amino acid in the form of an amide, extending the peptide (protein) chain to a desired length towards the N-terminus, deprotecting the N-terminal α-amino acid of the resulting peptide chain selectively to provide an N-terminal-deprotected fragment, preparing a peptide (protein) fragment with its C-terminal carboxyl group selectively deprotected, and condensing the two fragments in a solvent such as the mixed solvent as mentioned above. The condensation reaction can be carried out in the same manner as described hereinbefore. After purification of the protected protein thus obtained by condensation, all the protective groups are eliminated by the procedures described hereinbefore to provide the contemplated protein in crude form. This crude protein is purified by suitable known purification techniques and lyophilized to provide the desired protein amide.

A method for providing the protein in an ester form comprises condensing the α-carboxyl group of the C-terminal amino acid with a suitable alcohol to prepare the corresponding ester and subjecting this ester to the same procedure as described for purification of the protein amide to provide the objective protein ester.

The partial peptide of the protein of the present invention or a salt thereof can be produced by per se known procedures for peptide synthesis or by cleaving the protein with a suitable peptidase. The process for peptide synthesis may be a solid-phase synthesis and/or a liquid-phase synthesis. Namely, the objective peptide can be produced by condensing a partial peptide or amino acid capable of constituting the protein with the residual part thereof and, when the product has a protective group, the protective group is removed whereupon a desire peptide can be manufactured. The known technology for condensation and deprotection includes the procedures described in the following literature (1)–(5).

(1) M. Bodanszky and M. A. Ondetti, Peptide Synthesis, Interscience Publishers, New York, 1966
(2) Schroeder and Luebke, The Peptide, Academic Press, New York, 1965
(3) Nobuo Izumiya et al., Fundamentals and Experiments in Peptide Synthesis, Maruzen, 1975
(4) Haruaki Yajima and Shumpei Sakakibara, Biochemical Experiment Series 1, Protein Chemistry IV, 205, 1977
(5) Haruaki Yajima (ed.), Development of Drugs-Continued, 14, Peptide Synthesis, Hirokawa Shoten After the reaction, the partial peptide of the present invention can be purified and isolated by a combination of conventional purification techniques such as solvent extraction, distillation, column chromatography, liquid chromatography, and recrystallization. When the partial peptide isolated as above is in a free form, it can be converted to a suitable salt by known methods or method analogous thereto. On the other hand, when it is isolated as a salt, it can be converted to a free form or to any other salt thereof by known methods or method analogous thereto.

The DNA coding for the protein of the present invention may be any DNA comprising a nucleotide sequence encoding the protein of the present invention as mentioned above. It may also be any one of genomic DNA, genomic DNA library, cDNA derived from the tissues or cells as mentioned above, cDNA library derived from the tissues or cells as mentioned above, and synthetic DNA.

The vector for constructing a library may include bacteriophage, plasmid, cosmid, and phagemid. Furthermore, using a total RNA fraction or an mRNA fraction prepared from the tissues or cells, a direct amplification can be carried out by Reverse Transcriptase Polymerase Chain (hereinafter, referred to as RT-PCR method) technique.

Examples of DNA coding for the protein of the present invention are (1) a DNA comprising a nucleotide sequence represented by SEQ ID NO:7, or a DNA which comprises a nucleotide sequence hybridizing to the nucleotide sequence represented by SEQ ID NO:7 under a highstringent condition and codes for a protein having a substantially equivalent activity to the protein comprising the amino acid sequence represented by ID No:1, (2) a DNA comprising a nucleotide sequence represented by SEQ ID NO:8, or a DNA which comprises a nucleotide sequence hybridizing to the nucleotide sequence represented by SEQ ID NO:8 under a highstringent condition and codes for a protein having a substantially equivalent activity to the protein comprising the amino acid sequence represented by ID No:2, and so on.

Examples of the nucleotide sequence hybridizing to the nucleotide sequence represented by SEQ ID NO:7 are a nucleotide sequence of not less than about 70%, preferably not less than about 80%, more preferably not less than about 90%, for still better result, not less than about 95% identity to the nucleotide sequence represented by SEQ ID NO:7.

Examples of the nucleotide sequence hybridizing to the nucleotide sequence represented by SEQ ID NO:8 are a nucleotide sequence of not less than about 70%, preferably not less than about 80%, more preferably not less than about 90%, for still better result, not less than about 95% identity to the nucleotide sequence represented by SEQ ID NO:8.

The hybridization can be carried out by per se known methods such as the method described in Molecular Cloning, 2nd (J. Sambrook et al., Cold Spring Harbor Lab. Press, 1989) and so on. When a commercially available library is used, the hybridization can be carried out in accordance with the instructions given in the accompanying manual, and particularly, be carried out under a highstringent condition.

Under the highstringent condition, $Na^+$ concentration is at about 19 to 40 mM, preferably about 19 to 20 mM and a temperature is at about 50 to 70° C., preferably about 60 to 65° C. Particularly, the condition at about 19 mM of $Na^+$ and about 65° C. is preferred.

Preferable examples of the DNA coding for the protein comprising an amino acid sequence represented by SEQ ID NO:1 are a DNA comprising the nucleotide sequence represented by SEQ ID NO:7 (95th to 1618th nucleotide sequence of the nucleotide sequence of FIG. 4), and preferable example of the DNA coding for the protein comprising an amino acid sequence represented by SEQ ID NO:2 are a DNA comprising the nucleotide sequence represented by SEQ ID NO:8 (90th to 1640th nucleotide sequence of the nucleotide sequence of FIG. 6).

The DNA coding for the partial peptide of the present invention may be any DNA comprising a nucleotide sequence encoding the partial peptide of the present invention as mentioned above. It may also be any one of genomic DNA, genomic DNA library, cDNA derived from the tissues or cells as mentioned above, cDNA library derived from the tissues or cells as mentioned above, and synthetic DNA.

Examples of DNA coding for the partial peptide of the present invention are (1) a DNA comprising a partial nucleotide sequence of DNA which comprises a nucleotide sequence represented by SEQ ID NO:7, or a DNA comprising a partial nucleotide sequence of DNA which comprises a nucleotide sequence hybridizing under a highstringent condition to the nucleotide sequence represented by SEQ ID NO:7 and codes for a protein having a substantially equivalent activity to the protein comprising the amino acid sequence represented by SEQ ID NO:1, (2) a DNA comprising a partial nucleotide sequence of DNA which comprises a nucleotide sequence represented by SEQ ID NO:8, or a DNA comprising a partial nucleotide sequence of DNA which comprises a nucleotide sequence hybridizing under a highstringent condition to the nucleotide sequence represented by SEQ ID NO:8 and codes for a protein having a substantially equivalent activity to the protein comprising the amino acid sequence represented by SEQ ID NO:2, and so on.

Preferable examples of DNA coding for the partial peptide of the present invention are (1) a DNA comprising a nucleotide sequence represented by SEQ ID NO:9, or a DNA which comprises a nucleotide sequence hybridizing under a highstringent condition to the nucleotide sequence represented by SEQ ID NO:9 and codes for a partial peptide having a substantially equivalent activity to the protein of the present invention, (2) a DNA comprising a nucleotide sequence represented by SEQ ID NO:10, or a DNA which comprises a nucleotide sequence hybridizing under a highstringent condition to the nucleotide sequence represented by SEQ ID NO:10 and codes for a partial peptide having a substantially equivalent activity to the protein of the present invention, (3) a DNA comprising a nucleotide sequence represented by SEQ ID NO:11, or a DNA which comprises a nucleotide sequence hybridizing under a highstringent condition to the nucleotide sequence represented by SEQ ID NO:11 and codes for a partial peptide having a substantially equivalent activity to the protein of the present invention, (4) a DNA comprising a nucleotide sequence represented by SEQ ID NO:12, or a DNA which comprises a nucleotide sequence hybridizing under a highstringent condition to the nucleotide sequence represented by SEQ ID NO:12 and codes for a partial peptide having a substantially equivalent activity to the protein of the present invention, and so on.

Examples of the nucleotide sequence hybridizing to the nucleotide sequence represented by SEQ ID NO:9 or SEQ ID NO:10 are a nucleotide sequence of not less than about 70%, preferably not less than about 80%, more preferably not less than about 90%, for still better result, not less than about 95% identity to the nucleotide sequence represented by SEQ ID NO:9 or SEQ ID NO:10, and so on.

Examples of the nucleotide sequence hybridizing to the nucleotide sequence represented by SEQ ID NO:11 or SEQ ID NO:12 are a nucleotide sequence of not less than about 70%, preferably not less than about 80%, more preferably not less than about 90%, for still better result, not less than about 95% identity to the nucleotide sequence represented by SEQ ID NO:11 or SEQ ID NO:12, and so on.

The method for hybridization and the highstringent condition have same meanings as mentioned above.

Preferable examples of the DNA coding for the partial peptide represented by SEQ ID NO:3 are a DNA comprising the nucleotide sequence represented by SEQ ID NO:9 (386th to 1618th nucleotide sequence of the nucleotide sequence of FIG. 4) and so on. Preferable examples of the DNA coding for the protein represented by SEQ ID NO:4 are a DNA comprising the nucleotide sequence represented by SEQ ID NO:10 (371th to 1618th nucleotide sequence of the nucleotide sequence of FIG. 4) and so on.

Preferable examples of the DNA coding for the partial peptide comprising an amino acid sequence represented by SEQ ID NO:5 are a DNA comprising the nucleotide sequence represented by SEQ ID NO:11 (295th to 1640th nucleotide sequence of the nucleotide sequence of FIG. 6) and so on. Preferable examples of the DNA coding for the protein comprising an amino acid sequence represented by SEQ ID NO:6 are a DNA comprising the nucleotide sequence represented by SEQ ID NO:12 (280th to 1640th nucleotide sequence of the nucleotide sequence of FIG. 6) and so on.

The DNA encoding the entire protein or the partial peptide of the present invention can be cloned either by PCR amplification using synthetic DNA primers having a partial nucleotide sequence of the DNA coding for the protein or by hybridization using the DNA inserted in a suitable vector and labeled DNA fragment or synthetic DNA coding for a part or full region of the protein or the partial peptide of the present invention. The hybridization can be carried out by the method described in Molecular Cloning, 2nd (J. Sambrook et al., Cold Spring Harbor Lab. Press, 1989). When a commercially available DNA library is used, the instructions given in the accompanying manual can be followed.

The substitution of the nucleotide sequence of the DNA can be carried out by the per se known method such as Gapped duplex method, Kunkel method and so on by using the known kits such as Mutan™-G (Takara corporation), Mutan™-K (Takara corporation) and so on.

The cloned DNA coding for the protein of the present invention can be used directly or after digestion with a restriction enzyme or after addition of a linker depending on purposes. This DNA may have ATG as the translation initiation codon at the 5' end and TAA, TGA, or TAG as the termination codon at the 3' end. The translation initiation and termination codons can be added by means of suitable DNA adapters.

An expression vector for the protein of the present invention can be produced by, for example, (a) cutting out an objective DNA fragment from the DNA for the protein of the present invention and (b) ligating the objective DNA fragment with the downstream side of a promoter in a suitable expression vector.

The vector may include plasmids derived from *Escherichia coli*, e.g., pBR322, pBR325, pUC12, pUC13, etc.; plasmids derived from *Bacillus subtilis,* e.g., pUB110, pTP5, pC194, etc.; plasmids derived from yeasts e.g., pSH19, pSH15, etc.; bacteriophages such as λ-phage: animal virus such as retrovirus, vaccinia virus, etc.; insect virus; and other vecters such as pA1-11, pXT1, pRc/CMV, pRc/RSV, pcDNAI/Neo and so on.

According to the present invention, any promoter can be used as long as it is appropriate for the host cell which is used for expressing a gene. When the host is an animal cell, the promoter include SRα promoter, SV40 promoter, LTR promoter, CMV (cytomegalovirus) promoter, HSV-TK promoter, etc., and CMV promoter and SRα promoter are preferably used. When the host for the transformation is *Escherichia coli*, the promoter are preferably trp promoter, lac promoter, recA promoter, $\lambda P_L$ promoter, lpp promoter, T7 promoter, etc. When the host for the transformation is *Bacillus*, the promoter are preferably SPO1 promoter, SPO2 promoter, penP promoter, etc. When the host is a yeast, the promoter are preferably PHO5 promoter, PGK promoter, GAP promoter, ADH promoter, AOX1 promoter, etc. When the host is an insect cell, the promoter include polyhedrin promoter, P10 promoter, etc.

The expression vectors may, if necessary, further comprise enhancers, splicing signals, polyadenylation signals, selective markers, SV40 duplicate origin (hereinafter referred to as SV40 ori). Examples of selective markers are dihydrofolic acid reductase (hereinafter referred to as dhfr gene (methotrexate (MTX) registant)), neomycin-resistant gene (hereinafter referred to as Neo, G418 resistant) and so on. Particularly, when the dhfr gene is used as a selective marker against gene-deficient chinese hamster cell lines, cells transfected by the objective gene can be selected in a thymidine-free medium.

Furthermore, an appropriate signal sequence for a host can be added to the N-terminal side of the protein. When the host is *Escherichia coli*, the utilizable signal sequences may include PhoA signal sequence, OmpA signal sequence, etc. When the host is *Bacillus*, they may include α-amylase signal sequence, subtilisin signal sequence, etc. When the host is a yeast, they may include MFα signal sequence, SUC2 signal sequence, etc. When the host is an animal cell, they may include insulin signal sequence, α-interferon signal sequence, antibody molecule signal sequence, etc.

A transformant or transfectant is produced by using the vector thus constructed, which carries the DNA coding for the protein of the present invention.

The host may be, for example, *Escherichia* species, *Bacillus* species, yeast cells, insect cells, insects, animal cells, etc.

Examples of *Escherichia* species include *Escherichia coli* K12·DH1 (Proceedings of the National Academy of Sciences of the United State of America, Vol. 60, 160 (1968)), JM103 (Nucleic Acids Research, Vol. 9, 309 (1981)), JA221 (Journal of Molecular Biology, Vol. 120, 517 (1978)), HB101 (Journal of molecular Biology, Vol, 41, 459 (1969)), C600 [Genetics, Vol. 39, 440 (1954)), etc.

Examples of *Bacillus* species are, for example, *Bacillus subtilis* MI114 (Gene, Vol. 24, 255 (1983)), 207–21 (Journal of Biochemistry, Vol. 95, 87 (1984)), etc.

Examples of yeast cells are, for example, *Saccharomyces cerevisiae* AH22, AH22R⁻, NA87-11A, DKD-5D or 20B-12, *Schizosachcaromyces pombe* NCYC1913 or *Pichia pastoris*, etc.

Examples of insect cells are, for example, *Spodoptera frugiperda* cell (Sf cell), MG1 cell derived from center intestine of *Trichoplusia ni*, High Five™ cell derived from eggs of *Trichoplusia ni*, *Mamestra brassicae*-derived cell, *Estigmena acrea*-derived cell and so on when virus is AcNPV; and *Bombyx mori* N cell (BmN cell) and so on when virus is BmNPV. Examples of the Sf cell are, for example, Sf9 cell (ATCC CRL 1711), Sf21 cell [both, Vaughn J. L. et al., In Vivo, 13, 213–217(1977)] and so on.

Examples of insects include a larva of silkworm (*Bombyx mori* larva) (Maeda et al., Nature, 315, 592(1985)).

Examples of animal cells are, for example, monkey-derived COS-7 cell line, Vero cell line, Chinese hamster ovary cell line (hereinafter referred to as CHO cell), dhfr gene-deficient Chinese hamster cell line (hereinafter referred to as CHO(dhfr⁻) cell), mouse L cell, mouse AtT-20, mouse myeloma cell, rat GH3, human FL, 293 cell, C127 cell, BALB3T3 cell, Sp-2/O cell, etc. Among them, CHO cell, CHO(dhfr⁻) cell, 293 cell, etc. are preferred.

Depending on host cells used, transformation is done using standard techniques appropriate to such cells.

Transformation of *Escherichia* species can be carried out in accordance with methods as disclosed in, for example, Proceedings of the National Academy of Sciences of the United State of America, Vol. 69, 2110 (1972), and Gene, Vol. 17, 107 (1982), etc. Transformation of *Bacillus* species can be carried out in accordance with methods as disclosed in, for example, Molecular & General Genetics, Vol. 168, 111 (1979), etc.

Transformation of yeast cells can be carried out in accordance with methods as disclosed in, for example, Methods in Enzymology, 194, 182–187(1991), etc. Transformation of insect cells or insects can be carried out in accordance with methods as disclosed in, for example, Bio/Technology, 6, 47–55, (1988).

Transformation of animal cells can be carried out by methods as disclosed in, for example, Cell Engineering, separate vol. 8, New Cell Engineering Experiment Protocol, 263–267(1995) (Shujun Company), Virology, Vol. 52, 456 (1973), etc.

In introducing the expression vector into cells, known methods such as a calcium phosphate method (Graham, F. L. and van der Eb, A. J.: Virology, 52, 456–467(1973)), an electroporation (Neumann, E. et al., EMBO Journal, 1,841–845(1982)), etc. may be used.

The transformants or transfectants wherein the expression vector carrying the DNA coding for the protein can be obtained according to the aforementioned techniques.

Examples of methods for expressing the protein of the present invention stably using animal cells are a method for selecting the cells wherein the above-mentioned expression vector is incorporated in the chromosome by means of clone selection. Briefly, the transformant is first selected using the above-mentioned selective marker as an index for selection. Then the animal cell produced as such using the selective marker is repeatedly subjected to a clone selection to give an aminal cell strain which stably exhibits a high ability of expressing the protein of the present invention. When a dhfr gene is used as a selective marker, the resisting cells are selected by a culture with a sequential increase in the MTX concentration to amplify the DNA coding for the protein of the present invention with dhfr gene in the cells whereby an animal cell strain exhibiting far higher expression can be obtained.

The protein of the present invention or a salt thereof can be also manufactured by culturing the transformant under a condition where the DNA coding for the protein of the present invention can be expressed to express and accumulate the protein of the present invention.

Culture of the transformants (transfectants) of *Escherichia* or *Bacillus* species can be carried out preferably in a liquid culture medium. The culture medium may contains carbon sources, nitrogen sources, minerals, etc. which are necessary for growing the transformants. The carbon sources may include glucose, dextrin, soluble starch, sucrose, etc. The nitrogen sources may include organic or inorganic substances such as ammonium salts, nitrates, corn steep liquor, peptone, casein, meat extracts, bean-cakes, potato extracts, etc. Examples of the minerals may include calcium chloride, sodium dihydrogen phosphate, magnesium chloride, etc. It is further allowable to add yeast extracts, vitamines, growth-promoting factors, etc. It is suitable that the pH of culture medium is at about 5 to 8.

The culture medium for *Escherichia* species is, for example, preferably M9 medium which contains glucose and casamino acid (Miller, Journal of Experiments in Molecular Genetics, 431–433, Cold Spring Harbor Laboratory, New York, (1972). If necessary, drugs such as 3β-indolyl acrylic acid can be added to the medium to improve efficiency of the promoter. In the case of *Escherichia* organisms as a host, the culture is carried out usually at about 15 to 43° C. for about 3 to 24 hours. As required, aeration and stirring may be applied. In the case of *Bacillus* organisms as a host, the culture is carried out usually at about 30 to 40° C. for about 6 to 24 hours. As required, aeration and stirring may also be applied.

In the case of yeast transformants, the culture medium used may include, for example, Burkholder minimum medium (Bostian, K. L. et al., Proceedings of the National Academy of Sciences of the United State of America, Vol. 77, 4505 (1980)), SD medium containing 0.5% casamino acid (Bitter, G. A. et al., Proceedings of the National Academy of Sciences of the United State of America, Vol. 81, 5330 (1984)), etc. It is preferable that the pH of the culture medium is adjusted to be from about 5 to 8. The culture is carried out usually at about 20 to 35° C. for about 24 to 72 hours. As required, aeration and stirring may be applied.

In the case of the transformants (or transfectants) of insect cells or insects, the culture medium used may include the Grace's insect medium supplemented with additives such as inactivated 10% bovine serum (Grace, T. C. C., Nature, 195, 788 (1962)). It is preferable that the pH of the culture medium is adjusted to be about 6.2 to 6.4. The culture is usually carried out at about 27° C. for about 3 to 5 days. As desired, aeration and stirring may be applied.

In the case of the transformants (or transfectants) of animal cells, the culture medium used may include MEM medium (Science, Vol. 122, 501 (1952)), DMEM medium (Virology, Vol. 8, 396 (1959)), RPMI 1640 medium (Journal of the American Medical Association, Vol. 199, 519 (1967)), 199 medium (Proceedings of the Society of the Biological Medicine, Vol. 73, 1 (1950)), etc. which are containing, for example, about 5 to 20% of fetal calf serum. It is preferable that the pH is from about 6 to 8. The culture is usually carried out at about 30 to 40° C. for about 15 to 72 hours. As required, medium exchange, aeration and stirring may be applied. Especially when CHO (dhfr⁻) cells and dhfr selective marker gene are used, it is preferred to use a DMEM medium containing a dialyzed fetal bovine serum which rarely contains thymidine.

Separation and purification of the protein from the above-mentioned cultures can be carried out according to methods described herein below.

To extract the protein from the cultured microorganisms, insects or cells, the microorganisms or cells are collected by known methods after the culture, suspended in a suitable buffer solution, disrupted by ultrasonic waves, lysozyme and/or freezing and thawing, etc. and, then, a crude protein extract is obtained by centrifugation or filtration. Other conventional extraction or isolation methods can be applied. The buffer solution may contain a protein-denaturing agent such as urea or guanidine hydrochloride or a surfactant such as Triton X-100™.

In the case where proteins are secreted into culture media, supernatants are separated from the microorganisms or cells after culture and collected by known methods. The culture supernatant containing the protein can be purified by suitable combinations of known methods for separation, isolation and purification. The known methods of separation, isolation and purification may include methods which utilizes solubility, such as salting out or sedimentation with solvents, methods which utilizes chiefly a difference in the molecular size or weight, such as dialysis, ultrafiltration, gel filtration and SDS-polyacrylamide gel electrophoresis, methods utilizing a difference in the electric charge, such as ion-exchange chromatography, methods utilizing specific affinity such as affinity chromatography, methods utilizing a difference in the hydrophobic property, such as reversed-phase high-performance liquid chromatography, and methods utilizing a difference in the isoelectric point such as isoelectric electrophoresis, etc.

In cases where the protein thus obtained is in a free form, the free-form protein can be converted to a salt thereof by known methods or method analogous thereto. In case, where the protein thus obtained is in a salt form vice versa, the protein salt can be converted to a free form or to any other salt thereof by known methods or method analogous thereto.

The protein produced by the transformant can be arbitrarily modified or a polypeptide can be partly removed therefrom, by a suitable protein-modifying enzyme before or after the purification. The protein-modifying enzyme may include trypsin, chymotrypsin, arginyl endopeptidase, protein kinase, glycosidase, etc. The activity of the protein of the present invention thus obtained can be measured by binding assay with a labeled ligand or by enzyme immunoassays (enzyme linked immunoassays) using specific antibodies.

The antibodies against the protein of the present invention, its partial peptide or a salt of either of them are any antibodies such as polyclonal antibodies and monoclonal antibodies which can recognize the protein of the present invention, its partial peptide or a salt of either of them.

The antibodies against the protein of the present invention, its partial peptide or a salt of either of them (hereinafter referred to as the protein of the present invention) may be manufactured by methods per se known to those of skill in the art or methods similar thereto, using the protein of the present invention as antigen. For example, polyclonal antibodies can be manufactured by the method as given below.

Preparation of Monoclonal Antibody:

(a) Preparation of Monoclonal Antibody-Producing Cells

The protein of the present invention is administered to warm-blooded animals either solely or together with carriers or diluents to the site favorable for antibody production. In order to potentiate the antibody productivity upon the administration, complete Freund's adjuvants or incomplete Freund's adjuvants may be administered. The administration is usually carried out once every 2 to 6 weeks and 2 to 10 times in total. Examples of the applicable warm-blooded animals are monkeys, rabbits, dogs, guinea pigs, mice, rats, sheep, goats and chickens. The use of mice and rats is preferred.

In establishing cells which produce monoclonal antibodies, an animal with the detectable antibody titer is selected from animals (e.g. mice) immunized with antigens, then spleen or lymph node is collected after 2 to 5 days from the final immunization and antibody-producing cells contained therein are fused with myeloma cells derived from homogeneous or heterogeneous animals to obtain monoclonal antibody-producing hybridomas. Measurement of the antibody titer in antisera may, for example, be carried out by reacting a labeled protein, which will be mentioned later, with the antiserum followed by measuring the binding activity of the labeling agent with the antibody. The cell fusion may be carried out, for example, by a method of Koehler and Milstein (Nature, 256, 495, 1975). Examples of the fusion accelerator are polyethylene glycol (PEG), Sendai virus, etc. and the use of PEG is preferred.

Examples of the myeloma cells are those derived from warm-blooded animals such as NS-l, P3U1, SP2/0, AP-1, etc. and the use of P3U1 is preferred. The preferred fusion ratio of the numbers of antibody-producing cells used (spleen cells) to the numbers of myeloma cells is within a range of about 1:1 to 20:1. When PEG (preferably, PEG 1000 to PEG 6000) is added in a concentration of about 10 to 80% followed by incubating at 20 to 40° C., preferably, at 30 to 37° C., for 1 to 10 minutes, an efficient cell fusion can be carried out.

Various methods may be applied for screening a hybridoma which produces a monoclonal antibody. For example, a supernatant of hybridoma culture is added to a solid phase (e.g. microplate) to which the protein antigen is adsorbed either directly or with a carrier, then anti-immunoglobulin antibody (anti-mouse immunoglobulin antibody is used when the cells used for the cell fusion are those of mouse) which is labeled with a radioactive substance, an enzyme or the like, or protein A is added thereto and then monoclonal antibodies bound on the solid phase are detected; or a supernatant of the hybridoma culture is added to the solid phase to which anti-immunoglobulin or protein A is adsorbed, then the protein labeled with a radioactive substance or an enzyme is added and monoclonal antibodies bound with the solid phase is detected.

Selection and cloning of the monoclonal antibody-producing hybridoma may be carried out by methods per se known to those of skill in the art or methods similar thereto. Usually, it is carried out in a medium for animal cells, containing HAT (hypoxanthine, aminopterin and thymidine). With respect to a medium for the selection, for the cloning and for the growth, any medium may be used so far as hybridoma is able to grow therein. Examples of the medium are an RPMI 1640 medium (Dainippon Pharmaceutical Co., Ltd., Japan) containing 1 to 20% (preferably 10 to 20%) of fetal calf serum (FCS), GIT medium (Wako Pure Chemical, Japan) containing 1 to 20% of fetal calf serum and a suitable serum-free medium for hybridoma (SFM-101; Nissui Seiyaku, Japan). The culture temperature is usually 20 to 40° C. and, preferably, about 37° C. The culture period is usually from five days to three weeks and, preferably, one to two weeks. The culture is usually carried out in 5% carbon dioxide gas. The antibody titer of the supernatant of the hybridoma culture may be measured by the same manner as in the above-mentioned measurement of the antibody titer in the antiserum.

(b) Purification of the Monoclonal Antibody

The separation and purification of the monoclonal antibody may be carried out by methods for separating/purifying immunoglobulin such as salting-out, precipitation with alcohol, isoelectric precipitation, electrophoresis, adsorption/deadsorption using ion exchangers such as DEAE, ultracentrifugation, gel filtration, specific purifying methods in which only an antibody is collected by treatment with an active adsorbent such as an antigen-binding solid phase, protein A or protein G and the bond is dissociated whereupon the antibody is obtained.

Preparation of a Polyclonal Antibody:

The polyclonal antibody of the present invention can be produced by per se known methods or methods analogous thereto. The method comprises preparing an immunogen (antigen protein) per se or a conjugate of an imunogen with a carrier protein, immunizing a warm-blooded animal in the same manner as described for the production of the monoclonal antibody, harvesting a fraction containing the antibody against the protein of the present invention from the immunized animal, and purifying the harvested antibody.

Referring to the immunogen-carrier protein conjugate for use in the immunization of a warm-blooded animal, the kind of carrier protein and the ratio of the carrier and hapten are not particularly restricted only if the production of the antibody against the hapten conjugated with the particular carrier protein and used for immunization proceeds efficiently. Thus, for example, bovine serum albumin, bovine thyroglobulin, hemocyanine, or the like is coupled in the weight ratio of about 0.1 to 20, preferably about 1 to about 5, to unity of the hapten.

A variety of condensing agents can be used for this coupling between the hapten and the carrier. Thus, for example, a glutaraldehyde, carbodiimide, maleimide, or a thiol or dithiopyridyl group-containing active ester reagent can be employed.

The condensation reaction product is administered to a warm-blooded animal at a site favorable for antibody production, either as it is alone or together with a carrier or diluent. Enhancing antibody production, complete Freund's adjuvant or incomplete Freund's adjuvant may be administered. Administration is carried out generally once in about 2 to 6 weeks for a total of about 3 to 10 times.

The polyclonal antibody can be harvested from the blood, ascites fluid, or other body fluid, preferably from the blood, of the host warm-blooded animal.

The polyclonal antibody titer in the antiserum can be determined in the same manner as the determination of monoclonal antibody described hereinbefore. The separation and purification of the polyclonal antibody can be carried out by the same method as that described for the separation and purification of monoclonal antibody.

The antisense DNA having a nucleotide sequence complementary or substantially complementary to the DNA coding for the protein or the partial peptide of the present invention (hereinafter referred to as the DNA of the present invention) can be any antisense DNA having a nucleotide sequence complementary or substantially complementary to that of the DNA of the present invention and capable of suppressing expression of the DNA.

The nucleotide sequence substantially complementary to the DNA of the present invention may, for example, be a nucleotide sequence having an identity of not less than about 70%, preferably not less than about 80%, more preferably not less than about 90%, and for still better results, not less than about 95% to the total nucleotide sequence or partial nucleotide sequence of the nucleotide sequence complementary to that the DNA of the present invention. Particularly preferred is an antisense DNA having an identity of not less than about 70%, preferably not less than about 80%, and more preferably not less than about 90%, and for still better results, not less than about 95% to the nucleotide sequence of the domain, of the complete nucleotide sequence complementary to that of the DNA of the invention, which encodes the N-terminal region of the protein of the present invention (e.g. the nucleotide sequence of the domain around the initiation codon). The antisense DNA can be synthesized using a known DNA synthesis hardware.

The protein of the present invention is a metalloprotease (preferably human-liver metalloprotease) such that the molecular weight of its proteinaceous domain is about 2 to $7 \times 10^4$ Da, preferably about 2 to $6 \times 10^4$ Da, and the molecular weight of its proteolytic domain is about 2 to $5 \times 10^4$ Da, the activity of which is elevated in, for example, ovulation, development and differentiation, osteogenesis, atretic uterus, and vascularization. Moreover, its activity is increased in, for example, rheumatoid arthritis, osteoarthritis, cancer (metastasis and invasion), liver disease such as hepatolienal fibrosis and cirrhosis, peridontitis, pulmonary fibrosis, corneal ulcer, gastric ulcer, myocardiopathy, aneurysm, otosclerosis, epidermolysis bullosa, premature delivery, and atherosclerosis. On the other, its activity is suppressed in, for example, diabetic nephropathy, glomerulonephritis, pulmonary fibrosis, hepatolienal fibrosis, hepatocirrhosis, osteopetrosis, herniated disk, etc.

Uses for the protein of the present invention or its partial peptide thereof, or a salt of either of them (hereinafter sometimes referred to briefly as the protein of the present invention), the DNA coding for the protein or its partial peptide of the invention (hereinafter sometimes referred to briefly as the DNA of the present invention), the antibody against the protein of the present invention (hereinafter sometimes referred to as the antibody of the present invention), and the antisense DNA are now described.

(1) Therapeutic or prophylactic composition for various diseases with which the protein of the present invention is associated In the event of an abnormality or defect in the DNAs of metalloproteases, or when the expression or the activity of metalloproteases is suppressed, various diseases such as diabetic nephropathy, glomerulonephritis, pulmonary fibrosis, hepatolienal fibrosis, hepatocirrhosis, osteopetrosis and herniated disk are induced.

Therefore, the protein or the DNA of the present invention can be used as a pharmaceutical composition such as a therapeutic or prophylactic composition for a variety of diseases which associates with an abnormal expression or activity of metalloprotease such as diabetic nephropathy, glomerulonephritis, pulmonary fibrosis, hepatolienal fibrosis, hepatocirrhosis, osteopetrosis, herniated disk, and so on.

For example, when there is a patient whose signal transductions in cells cannot function sufficiently or normally because of a decrease or a defect in the metalloproteases in vivo, the role of the metalloproteases for said patient can be expected sufficiently or normally by:

(a) administering the DNA coding for the protein of the present invention to the patient to express it;
(b) inserting the DNA coding for the protein of the present invention into cells to express it and transplanting the cells to said patient, or
(c) administering the protein to the patient.

When the DNA of the present invention is used as the above-mentioned pharmaceutical composition, said DNA may be used alone or after inserting it into a suitable vector such as retrovirus vector, adenovirus vector, adenovirus-associated virus vector, pox virus etc. followed by subjecting the product vector to a conventional means. The DNA can also be administered as "naked" DNA, with physiologically acceptable carriers such as adjuvants to assist in uptake, by "gene" gun or by a catheter such as a catheter with a hydrogel.

If one wishes to use the protein of the present invention, one would use it in a purified form, preferably in a purity of at least 90%, more preferably at least 95%, still more preferably at least 98% and most preferably at least 99%.

For example, the protein of the present invention can be used orally in the form of tablets which may be sugar coated as necessary, capsules, elixirs, microcapsules etc., or non-orally in the form of injectable preparations such as aseptic solutions and suspensions in water or other pharmaceutically acceptable liquids. These preparations can be produced by mixing the protein of the present invention with physiologically acceptable carriers, flavoring agents, excipients, vehicles, antiseptics, stabilizers, binders etc. in unit dosage forms required for generally accepted manners of pharmaceutical preparation. Active ingredient contents in these preparations are set so that an appropriate dose within the specified range is obtained.

Additives which can be mixed in tablets, capsules etc. include binders such as gelation, corn starch, tragacanth and gum arabic, excipients such as crystalline cellulose, swelling agents such as corn starch, gelatin and alginic acid, lubricants such as magnesium stearate, sweetening agents such as sucrose, lactose and saccharin, and flavoring agents such as peppermint, akamono oil and cherry. When the unit dosage form is the capsule, the above-mentioned materials may further incorporate liquid carriers such as oils and fats. Sterile compositions for injection can be formulated by ordinary methods of pharmaceutical preparation such as by dissolving or suspending active ingredients, naturally occurring vegetable oils such as sesame oil and coconut oil, etc. in vehicles such as water for injection to create pharmaceutical compositions.

Aqueous liquids for injection include physiological saline and isotonic solutions containing glucose and other auxiliary agents, e.g., D-sorbitol, D-mannitol and sodium chloride, and may be used in combination with appropriate dissolution aids such as alcohols, e.g., ethanol, polyalcohols, e.g., propylene glycol and polyethylene glycol, nonionic surfactants, e.g., polysorbate 80™ and HCO-50 etc. Oily liquids include sesame oil and soybean oil, and may be used in combination with dissolution aids such as benzyl benzoate and benzyl alcohol. Furthermore the above-mentioned materials may also be formulated with buffers, e.g., phosphate buffer and sodium acetate buffer; soothing agents, e.g., benzalkonium chloride, procaine hydrochloride; stabilizers, e.g., human serum albumin, polyethylene glycol; preservatives, e.g., benzyl alcohol, phenol; antioxidants etc. The thus-prepared pharmaceutical composition such as an injectable liquid is normally filled in an appropriate ampule.

The vector comprising the DNA of the present invention can be formulated as well as mentioned above, and usually can be used non-orally.

Because the thus-obtained preparation is safe and of low toxicity, it can be administered to humans or mammals (e.g., rat, mouse, guinia pig, rabbit, sheep, pig, bovine, horse, cat, dog, monkey, etc.).

The dose of the protein of the present invention may vary depending on subject disease, subject of administration, way of administration, and so on. When the protein of the present invention is used, for example, for treating diabetic nephropathy by oral administration, the dose of the protein of the present invention is normally about 0.1 to 100 mg, preferably 1.0 to 50 mg, and more preferably 1.0 to 20 mg per day for an adult (weighing 60 kg). When the protein of the present invention is used, for example, for treating herniated disk by non-oral administration, it is advantageous to administer the protein of the present invention to the diseased part in the form of injectable preparation at a daily dose of about 0.01 to 30 mg, preferably about 0.1 to 20 mg, and more preferably about 0.1 to 10 mg per administration by an intravenous injection for an adult (weighing 60 kg), depending on subject of administration, subject disease and so on. For other animal species, corresponding does as converted per 60 kg weight can be administered.

(2) Screening of compounds as candidates which are medicinally useful against diseases Any compounds or their salts which activate the function, for example a proteolytic activity, of the protein of the present invention can be used as a pharmaceutical composition such as a therapeutic or prophylactic composition for diseases such as diabetic nephropathy, glomerulonephritis, pulmonary fibrosis, hepatolienal fibrosis, hepatocirrhosis, osteopetrosis, and herniated disk. Therefore, the protein of the present invention is useful as a screening reagent for compounds or their salts, which activate the function of the protein of the present invention.

On the other hand, any compounds or their salts which inhibit the function of the protein of the present invention can be used as a pharmaceutical composition such as a therapeutic or prophylactic composition for wound, rheumatoid arthritis, osteoarthritis, cancer (metastasis and invasion), liver disease such as hepatolienal fibrosis and cirrhosis, peridontitis, pulmonary fibrosis, corneal ulcer, gastric ulcer, myocardiopathy, aneurysm, otosclerosis, epidermolysis bullosa, premature delivery, atherosclerosis, septemia, multiple (disseminated) sclerosis, cachexia, hypercalcemia, leukemia, lymphoma, diabetes, autoimmune diseases such as systemic lupus erythematosus, asthma, immune diseases such as allergic rhinitis and atopic dermatitis, generalized inflammatory reactions associated with trauma, burn or acute pancreatitis, ischemia-reperfusion syndrome, cardiovascular diseases such as myocardial infarction, congestive heart failure, etc., organ transplantation and graft-vs.-host disease (GVHD). Therefore, the protein of the present invention is useful as a screening reagent for those compounds or their salts which inhibit the function of the protein of the present invention.

The present invention, therefore, provides
(1) a method for screening for a compound which activates the function (e.g. a proteolytic activity) of the protein of the present invention or its partial peptide, or a salt of either of them (such compound will sometimes be referred to as activator), or a compound which inhibits the function of the protein of the present invention or its partial peptide thereof, or a salt of either of them (such compound will sometimes be referred to as inhibitor) characterized in that the protein of the present invention or its partial peptide, or a salt of either of them, is used as a screening reagent.

More particularly, the invention provides
(2) a method for screening for the activator or inhibitor, characterized by comparing the results in cases of (i) a substrate is contacted with the protein of the present invention and (ii) a substrate and a test compound are contacted with the protein of the present invention.

More specifically, the above screening method is characterized by measuring and comparing the proteolytic activity of the protein of the present invention in cases of (i) and (ii).

The substrate may include any substances which may function as substrates for the protein of the present invention. Examples of the substrate are casein, azocasein, FITC-casein, radio(e.g. $^{14}C$, $^{3}H$, etc.) labeled casein, collagen, azocollagen, FITC-collagen, radio($^{14}C$, $^{3}H$, etc.)-labeled collagen, and oligopeptides having a (7-methoxycoumarin-4-yl)acetyl group in the N-terminal domain and an $N^3$-(2,4-dinitrophenyl)-2,3-diaminopropionyl group at a position towards the C-terminus by a few residues from the position where the first mentioned group is attached.

Examples of the test compound that can be used includes but is not limited to peptides, proteins, non-peptide compounds, synthetic compounds, fermentation products, cell extracts, plant extracts, and animal tissue extracts. Such compounds may be novel substances or known substances.

For carrying the above screening method into practice, the protein of the present invention is first suspended in a suitable screening buffer to prepare a sample. The buffer may be any buffer that does not affect the binding of the protein of the present invention to the substrate, such as a phosphate buffer or Tris-HCl buffer in a pH range of about 4 to 10 (preferably pH about 6 to 8).

The proteolytic activity of the protein of the present invention can be determined by the known PER method (F. T. Lundy et al. Electrophoresis, 16, 43, 1995), and so on. Specifically, any test compounds that activate the proteolytic activity by not less than about 20%, preferably not less than 30%, more preferably not less than 50%, in experiment (ii) as compared with experiment (i) can be selected as an activator of the proteolytic activity of the protein of the present invention, while any test compounds that inhibit the proteolytic activity by not less than about 20%, preferably not less than 30%, more preferably not less than 50%, in experiment (ii) as compared with experiment (i) can be selected as an inhibitor of the proteolytic activity of the protein of the present invention.

The screening kit of the present invention comprises the protein of the present invention or peptide, or a salt of either of them. The following is a typical screening kit embodying the principle of the present invention.
Screening Reagents:
(1) Screening buffer
  Tris-HCl buffer, pH 8.0
  (sodium chloride and calcium chloride contained)
(2) Protein sample
  The protein of the invention or its partial peptide
(3) Substrate
  Casein 20 mg/ml
(4) Detection
  Coomassie Brilliant Blue (CBB) staining Assay Protocol:
  Add aminophenyl mercuric acetate (final concentration 1 mM) to the protein of the present invention and react at 37° C. for 30 minutes. Electrophorese the reaction mixture on SDS-polyacrylamide gels (non-reducing) in accordance with PER (F. T. Lundy et al., Electrophoresis, 16, 43, 1995). Then, saturate the polyacrylamide gels with the substrate and react in the reaction medium at 37° C. for 16 hours. After the reaction, stain the gels with CBB to detect a proteolytic activity.

The compound or a salt thereof which can be identified by the screening method of the present invention or by using the screening kit of the present invention is a compound selected from among a peptide, protein, nonpeptide compound, synthetic compound, fermentation product, cell extract, plant extract, or animal tissue extract, which activates or inhibits the function of the protein of the present invention.

The salt of the compound may be the same those as mentioned above as to the protein of the present invention.

The compound which activates the function (e.g. proteolytic activity) of the protein of the present invention is safe and of low toxicity, and can be used as therapeutic and prophylactic composition for various diseases such as diabetic nephropathy, glomerulonephritis, pulmonary fibrosis, hepatolienal fibrosis, hepatocirrhosis, osteopetrosis, herniated disk and so on.

On the other hand, the compound which inhibits the function (e.g. proteolytic activity) of the protein of the present invention is safe and of low toxicity, and can be used as therapeutic and prophylactic composition for various diseases such as wound, rheumatoid arthritis, osteoarthritis, cancer (metastasis and invasion), liver disease such as hepatolienal fibrosis and cirrhosis, peridontitis, pulmonary fibrosis, corneal ulcer, gastric ulcer, myocardiopathy, aneurysm, otosclerosis, epidermolysis bullosa, premature delivery, atherosclerosis, septemia, multiple (disseminated) sclerosis, cachexia, hypercalcemia, leukemia, lymphoma, diabetes, autoimmune diseases such as systemic lupus erythematosus, asthma, immune diseases such as allergic rhinitis and atopic dermatitis, generalized inflammatory reactions associated with trauma, burn or acute pancreatitis, ischemia-reperfusion syndrome, cardio-vascular diseases such as myocardial infarction, congestive heart failure, etc., organ transplantation, graft-vs.-host disease (GVHD) and so on.

The compound which is identified by the screening method or the screening kit can be used as the above-mentioned therapeutic or prophylactic composition in accordance with a conventional means. The compound can be used in the form of tablets, capsules, elixirs, microcapsules, aseptic solutions, suspensions and so on as well as the pharmaceutical composition comprising the protein of the present invention as mentioned above.

Because the thus-obtained preparation is safe and of low toxicity, it can be administered to humans or mammals (e.g., rats, rabbits, sheep, pigs, bovines, cats, dogs, monkeys, etc.).

The dose of the compound or a salt thereof may vary depending on subject disease, subject of administration, way of administration, and so on. When the compound inhibiting the function of the protein of the present invention is used, for example, for treating diabetic nephropathy by oral administration, the dose of the compound is normally about 0.1 to 100 mg, preferably about 1.0 to 50 mg, and more preferably about 1.0 to 20 mg per day for an adult (weighing 60 kg). When the compound inhibiting the function of the protein of the present invention is used, for example, for treating diabetic nephropathy by non-oral administration, it is advantageous to administer the compound in the form of injectable preparation at a daily dose of about 0.01 to 30 mg, preferably about 0.1 to 20 mg, and more preferably about 0.1 to 10 mg per administration by an intravenous injection for an adult (weighing 60 kg), depending on subject of administration, subject disease and so on. For other animal species, corresponding does as converted per 60 kg weight can be administered.

(3) Quantitative determination of the protein of the present invention

The antibody of the present invention is capable of specifically recognizing the protein of the present invention and, accordingly, it can be used for quantitative determination of the protein of the present invention in test liquid samples and particularly for quantitative determination by sandwich immunoassays.

Thus, the present invention provides, for example, the following methods:

(i) a quantitative determination of the protein of the present invention in a test liquid sample, which comprises
 (a) competitively reacting the test liquid sample and a labeled protein of the present invention with the antibody of the present invention, and
 (b) measuring the ratio of the labeled protein of the present invention binding with said antibody; and
(ii) a quantitative determination of the protein of the present invention in a test liquid sample, which comprises
 (a) reacting the test liquid sample with an antibody immobilized on an insoluble carrier and a labeled antibody simultaneously or continuously, and
 (b) measuring the activity of the labeling agent on the insoluble carrier, wherein one antibody is capable of recognizing the N-terminal region of the protein of the present invention while another antibody is capable of recognizing the C-terminal region of the protein of the present invention.

When the monoclonal antibody of the present invention recognizing a protein of the present invention (hereinafter, sometimes referred to as "monoclonal antibody of the present invention") is used, the quantity of the protein of the present invention can be measured and, moreover, the protein of the present invention can be detected by means of a tissue staining, etc. as well. For such an object, antibody molecules per se may be used, or $F(ab')_2$, Fab' or Fab fractions of the antibody molecule may also be used. There is no particular limitation for the measuring method using the antibody of the present invention and any measuring method may be used so far as it relates to a method in which the amount of antibody, antigen or antibody-antigen complex, depending on or corresponding to the amount of antigen, e.g. the amount of the protein of the present invention in the liquid sample to be measured, is detected by a chemical or a physical means and then calculated using a standard curve prepared by a standard solution containing the known amount of antigen. For exmaple, nephrometry, competitive method, immunometric method and sandwich method are suitably used and, in terms of sensitivity and specificity, the sandwich method which will be described herein later is particularly preferred.

Examples of the labeling agent used in the measuring method using the labeling substance are radioisotopes, enzymes, fluorescent substances, luminescent substances, colloids, magnetic substances, etc. Examples of the radioisotope are $[^{125}I]$, $[^{131}I]$, $[^{3}H]$ and $[^{14}C]$. Preferred examples of the enzyme are those which are stable and with much specific activity, such as β-galactosidase, β-glucosidase, alkaline phosphatase, peroxidase and malate dehydrogenase. Examples of the fluorescent substance are fluorescamine, fluorescein isothiocyanate, etc. Examples of the luminescent substance are luminol, luminol derivatives, luciferin, lucigenin, etc. Further, a biotin-avidin system may also be used for binding an antibody or antigen with a labeling agent.

In an insolubilization (immobilization) of antigens or antibodies, a physical adsorption may be used or a chemical binding which is usually used for insolubilization or immobilization of proteins or enzymes may be used as well. Examples of the carrier are insoluble polysaccharides such as agarose, dextran and cellulose; synthetic resins such as polystyrene, polyacrylamide and silicone; glass; etc.

In a sandwich method, the test liquid is made to react with an insolubilized monoclonal antibody of the present invention (the first reaction), then it is allowed to react with an another labeled monoclonal antibody of the present invention (the second reaction) and the activity of the labeling agent on the insoluble carrier is measued whereupon the amount of the protein of the present invention in the test liquid can be determined. The first reaction and the second reaction may be conducted reversely or simultaneously or they may be conducted with an interval. The type of the labeling agent and the method of insolubilization may be the same as those mentioned hereinbefore. In the immunoassay by means of a sandwich method, it is not always necessary that the antibody used for the labeled antibody and the antibody for the solid phase is one type or one species but, with an object of improving the measuring sensitivity, etc., a mixture of two or more antibodies may be used as well.

In the method of measuring the protein of the present invention by the sandwich method of the present invention, the preferred monoclonal antibodies of the present invention used for the first and the second reactions are antibodies wherein their sites binding to the protein of the present invention are different from each other. Thus, antibodies used in the first and the second reactions are those wherein, when an antibody used in the second reaction recognizes the C-terminal region of the protein of the present invention, then another antibody recognizing the site other than C-terminal regions, e.g. recognizing the N-terminal region, is preferably used in the first reaction.

The monoclonal antibody of the present invention may be used in a measuring system other than the sandwich method such as a competitive method, an immunometric method and a nephrometry. In the competitive method, an antigen in the test solution and a labeled antigen are allowed to react with an antibody in a competitive manner, then an unreacted labeled antigen (F) and a labeled antigen (B) binding with an antibody are separated (i.e. B/F separation) and the labeled amount of any of B and F is measured whereupon the amount of the antigen in the test solution is determined. With respect to a method for such a reaction, there are a liquid phase method in which a soluble antibody is used as the antibody and the B/F separation is conducted by polyethylene glycol, a second antibody to the above-mentioned antibody, etc.; and a solid phase method in which an immobilized antibody is used as the first antibody or a soluble antibody is used as the first antibody while an immobilized antibody is used as the second antibody.

In the immunometric method, an antigen in the test solution and an immobilized antigen are subjected to a competitive reaction with a certain amount of a labeled antibody followed by separating into solid and liquid phases or the antigen in the test solution and an excess amount of labeled antibody are allowed to react, then an immobilized antigen is added to bind an unreacted labeled antibody with the solid phase and separated into solid and liquid phases. After that, the labeled amount of any of the phases is measured to determine the antigen amount in the test solution.

In the nephrometry, the amount of insoluble sediment which is produced as a result of the antigen-antibody reaction in a gel or in a solution is measured. Even when the antigen amount in the test solution is small and only a small amount of the sediment is obtained, a laser nephrometry wherein scattering of laser is utilized can be suitably used.

In applying each of those immunological measuring methods (immunoassays) to the measuring method of the present invention, it is not necessary to set up any special condition, operation, etc. therefor. A measuring system (assay system) for the protein of the present invention may be constructed taking the technical consideration of the persons skilled in the art into consideration in the conventional conditions and operations for each of the methods. With details of those conventional technical means, a variety of reviews, reference books, etc. may be referred to.

They are, for example, Hiroshi Irie (ed): "Radioimmunoassay" (Kodansha, Japan, 1974); Hiroshi Irie (ed): "Radioimmunoassay; Second Series" (Kodansha, Japan, 1979); Eiji Ishikawa et al. (ed): "Enzyme Immunoassay" (Igaku Shoin, Japan, 1978); Eiji Ishikawa et al. (ed): "Enzyme Immunoassay" (Second Edition) (Igaku Shoin, Japan, 1982); Eiji Ishikawa et al. (ed): "Enzyme Immunoassay" (Third Edition) (Igaku Shoin, Japan, 1987); "Methods in Enzymology" Vol. 70 (Immunochemical Techniques (Part A)); ibid. Vo. 73 (Immunochemical Techniques (Part B)); ibid. Vo. 74 (Immunochemical Techniques (Part C)); ibid. Vo. 84 (Immunochemical Techniques (Part D: Selected Immunoassays)); ibid. Vol. 92 (Immunochemical Techniques (Part E: Monoclonal Antibodies and General Immunoassay Methods)); ibid. Vol. 121 (Immunochemical Techniques (Part I: Hybridoma Technology and Monoclonal Antibodies)) (Academic Press); etc.

By using the antibody of the present invention in the above manner, the protein of the present invention can be assayed with high sensitivity.

In addition, when increase in concentration of the protein of the present invention is detected by determining the concentration of the protein of the present invention by using the antibody against the protein of the present invention, it may lead, with high probability, to the diagnosis of various diseases such as wound, rheumatoid arthritis, osteoarthritis, cancer (metastasis and invasion), liver disease such as hepatolienal fibrosis and cirrhosis, peridontitis, pulmonary fibrosis, corneal ulcer, gastric ulcer, myocardiopathy, aneurysm, otosclerosis, epidermolysis bullosa, premature delivery, atherosclerosis, septemia, multiple (disseminated) sclerosis, cachexia, hypercalcemia, leukemia, lymphoma, diabetes, autoimmune diseases such as systemic lupus erythematosus, asthma, immune diseases such as allergic rhinitis and atopic dermatitis, generalized inflammatory reactions associated with trauma, burn or acute pancreatitis, ischemia-reperfusion syndrome, cardiovascular diseases such as myocardial infarction, congestive heart failure, etc., organ transplantation, graft-vs.-host disease (GVHD) and so on. When decrease in concentration of the protein of the present invention is detected, it may lead, with high probability, to the diagnosis of various diseases such as diabetic nephropathy, glomerulonephritis, hepatolienal fibrosis, hepatocirrhosis, osteopetrosis, herniated disk and so on.

Thus, the antibody of the present invention is useful as a diagnostic agent for the above-mentioned diseases.

Furthermore, the antibody of the present invention can be used for the purpose of detecting the protein of the present invention which may be present in test samples such as body fluids or tissues. The antibody can also be used for the construction of an antibody column for purification of the protein of the present invention, detection of the protein of the present invention in the fractions in the course of purification, and analysis of the behavior of the protein of the present invention in the test cell.

(4) Gene diagnostic agent

By using the DNA of the present invention as a probe, for instance, an abnormality (gene abnormality) of the DNA or mRNA coding for the protein of the present invention or its partial peptide in humans or mammals (e.g. rat, mouse, guinea pig, rabbit, sheep, swine, bovine, horse, cat, dog, monkey, chimpanzee, etc.) can be detected. Therefore, the DNA of the present invention is useful as a gene diagnostic agent for the damage to the DNA or mRNA, mutation thereof, or decreased expression thereof, or increased expression or overexpression of the DNA or mRNA.

The above-mentioned gene diagnosis using the DNA of the present invention can be carried out by, for example, the Per se known Northern hybridization assay or PCR-SSCP assay [Genomics, 5, 874–879 (1989); Proceedings of the National Academy of Sciences of the United States of America, 86, 2766–2770 (1989)].

When increase in expression of the DNA is detected by Northern hybridization assay, it may lead, with high probability, to the diagnosis of wound, rheumatoid arthritis, osteoarthritis, cancer (metastasis and invasion), liver disease such as hepatolienal fibrosis and cirrhosis, peridontitis, pulmonary fibrosis, corneal ulcer, gastric ulcer, myocardiopathy, aneurysm, otosclerosis, epidermolysis bullosa, premature delivery, atherosclerosis, septemia, multiple (disseminated) sclerosis, cachexia, hypercalcemia, leukemia, lymphoma, diabetes, autoimmune diseases such as systemic lupus erythematosus, asthma, immune diseases such as allergic rhinitis and atopic dermatitis, generalized inflammatory reactions associated with trauma, burn or acute pancreatitis, ischemia-reperfusion syndrome, cardiovascular diseases such as myocardial infarction, congestive heart failure, etc., organ transplantation, graft-vs.-host disease (GVHD) and so on. when decrease in expression of the DNA in detected, it may lead, with high probability, to the diagnosis of diabetic nephropathy, glomerulonephritis, hepatolienal fibrosis, hepatocirrhosis, osteopetrosis, herniated disk and so on. When a mutation of the DNA is detected by the PCR-SSCP assay, it may lead, with high probability to diagnosis of wound, rheumatoid arthritis, osteoarthritis, cancer (metastasis and invasion), liver disease such as hepatolienal fibrosis and cirrhosis, peridontitis, pulmonary fibrosis, corneal ulcer, gastric ulcer, myocardiopathy, aneurysm, otosclerosis, epidermolysis bullosa, premature delivery, atherosclerosis, septemia, multiple (disseminated) sclerosis, cachexia, hypercalcemia, leukemia, lymphoma, diabetes, autoimmune diseases such as systemic lupus erythematosus, asthma, immune diseases such as allergic rhinitis and atopic dermatitis, generalized inflammatory reactions associated with trauma, burn or acute pancreatitis, ischemia-reperfusion syndrome, cardiovascular diseases such as myocardial infarction, congestive heart failure, etc., organ transplantation, graft-vs.-host disease (GVHD), diabetic nephropathy, glomerulonephritis, hepatolienal fibrosis, hepatocirrhosis, osteopetrois, herniated disk and so on.

(5) Antisense DNA

An antisense DNA capable of making complementary conjugate with the DNA of the present invention to suppress expression of the DNA is capable of inhibiting the function of the protein or the DNA of the present invention in the body. Therefore, the antisense DNA can be used as a pharmaceutical composition such as a therapeutic and prophylactic composition for diseases such as wound, rheumatoid arthritis, osteoarthritis, cancer (metasrasis and invasion), liver disease such as hepatolienal fibrosis and cirrhosis, periontitis, pulmonary fibrosis, corneal ulcer, gastric ulcer, myocardiopathy, aneurysm, otosclerosis, epidermolysis bullosa, premature delivery, atherosclerosis, septemia, multiple (disseminated) sclerosis, cachexia, hypercalcemia, leulemia, lymphoma, diabetes, systemic lupus erythematosus, asthma, allergic rhinitis, atopic dermatitis, trauma, burn, acute pancreatitis, ischemia-reperfusion syndrome, myocardial infarction, congestive heart failure, organ transplantation, graft-vs.-host disease (GVHD) and so on.

The antisense DNA can be used as the above-mentioned pharmaceutical composition in the same manner as the pharmaceutical composition comprising the DNA of the present invention as mentioned above.

(6) Preparation of non-human animals harboring a foreign DNA coding for the protein of the present invention Transgenic non-human animals which express the protein of the present invention can be constructed by using the DNA of the present invention. As the species of non-human animals that can be used, a variety of mammals (e.g. rat, mouse, rabbit, sheep, swine, bovine, cat, dog, monkey, etc.), etc. (hereafterin referred to as animals) can be mentioned. Particularly preferred are mouse and rabbit.

In transferring the DNA of the present invention to a host animal, it is generally advantageous to use the DNA as a gene construct prepared by ligating the DNA downstream of a promoter capable of expressing the DNA in animal cells. For the transfer of a rabbit-derived DNA of the invention, for instance, a DNA transgenic animal for high production of the protein of the present invention can be constructed by the microinjection of, for example, the fertilized rabbit egg with a gene construct prepared by ligating the DNA of the present invention as derived from an animal having high homology therewith downstream of a promoter capable of causing the expression of the DNA of the present invention in animal cells. As for such promoters, viral promoters or ubiquitous expression promoters such as and metallothionein promoters can also be used.

The transfer of the DNA into the fertilized egg cell stage is secured in all the germ and somatic cells of the host animal. The presence of the protein of the present invention in the germ cells of the DNA-transferred animal means that all the progeny of the transgenic animal invariably harbors the protein of the present invention in their germ and somatic cells The offsprings of such an animal to which the gene has been passed on have the protein of the present invention in all of their germ and somatic cells.

The transgenic animal in which the DNA of the present invention has been expressed is confirmed to retain the gene stably by copulation and then can be bred from generation to generation as the DNA-harboring animals in the usual breeding environment. Furthermore, by mating male and female animals harboring the objective DNA, it is possible to obtain homozygotes having the introduced gene in both of the homologous chromosomes, and by mating such partners, it is possible to insure that all the progeny animals will harbor this DNA.

The animal to which the DNA of the present invention has been passed on has the protein of the present invention expressed in a high degree so that it is useful as an animal for screening for compounds and salts which would activate or inhibit the proteolytic activity of the protein of the present invention.

The animal to which the DNA of the present invention has been transferred can also be used as a source of cells for tissue culture. For example, the protein of the present invention can be studied either directly by analyzing the DNA or RNA in the tissues of a mouse to which the DNA of the present invention has been transferred or analyzing a tissue containing the protein of the present invention as expressed by the gene. It is possible to culture cells from a tissue containing the protein of the present invention by the standard tissue culture technique and, using the culture, study the functions of cells derived from even those tissues which are generally difficult to culture, such as brain or peripheral tissue cells. Furthermore, by using such cells, drugs which activate the functions of various tissues may be selected. Moreover, if a high-expression cell line is provided, it will be possible to isolate and purify the protein of the present invention from the cell line.

In the specification and drawings of the present application, the abbreviations used for bases (nucleotides), amino acids and so forth are those recommended by the IUPAC-IUB Commission on Biochemical Nomenclature or those conventionally used in the art. Examples thereof are given below. Amino acids for which optical isomerism is possible are, unless otherwise specified, in the L form.

| | |
|---|---|
| DNA | Deoxyribonucleic acid |
| cDNA | Complementary deoxyribonucleic acid |
| A | Adenine |
| T | Thymine |
| G | Guanine |
| C | Cytosine |
| RNA | Ribonucleic acid |

-continued

| | |
|---|---|
| mRNA | Messenger ribonucleic acid |
| dATP | Deoxyadenosine triphosphate |
| dTTP | Deoxythymidine triphosphate |
| dGTP | Deoxyguanosine triphosphate |
| dCTP | Deoxycytidine triphosphate |
| ATP | Adenosine triphosphate |
| EDTA | Ethylenediaminetetracetic acid |
| SDS | Sodium dodecyl sulfate |
| Gly | Glycine |
| Ala | Alanine |
| Val | Valine |
| Leu | Leucine |
| Ile | Isoleucine |
| Ser | Serine |
| Thr | Threonine |
| Cys | Cysteine |
| Met | Methionine |
| Glu | Glutamic acid |
| Asp | Aspartic acid |
| Lys | Lysine |
| Arg | Arginine |
| His | Histidine |
| Phe | Phenylalanine |
| Tyr | Tyrosine |
| Trp | Tryptophan |
| Pro | Proline |
| Asn | Asparagine |
| Gln | Glutamine |
| pGlu | Pyroglutamic acid |
| Me | Methyl |
| Et | Ethyl |
| Bu | Butyl |
| Ph | Phenyl |
| TC | Thiazolidine-4(R)-carboxamide |

Substitution groups, protecting groups and reagents used in the specification of the present application are represented by the symbols set forth below.

| | |
|---|---|
| Tos | p-toluene sulfonyl |
| CHO | Formyl |
| Bzl | Benzyl |
| Cl$_2$-Bzl: | 2,6-dichlorobenzyl |
| Bom | Benzyloxymethyl |
| Z | Benzyloxycarbonyl |
| Cl-Z | 2-chlorobenzyloxycarbonyl |
| Br-Z | 2-bromobenzyloxycarbonyl |
| Boc | Tert-butoxycarbonyl |
| DNP | Dinitrophenyl |
| Trt | Trityl |
| Bum | Tert-butoxymethyl |
| Fmoc | N-9-fluorenylmethyloxycarbonyl |
| HOBt | 1-hydroxybenzotriazole |
| HOOBt | 3,4-dihydro-3-hydroxy-4-oxo-1,2,3-benzotriazine |
| HONB | 1-hydroxy-5-norbornene-2,3-dicarboximide |
| DCC | Dicyclohexylcarbodiimide |
| Cha | Cyclohexyl alanyl |
| Abu | Aminobutyrate |
| Abz | 2-aminobenzoyl |

Each SEQ ID NO set forth in the SEQUENCE LISTING of the specification refers to the following sequence:

SEQ ID NO:1 shows an amino acid sequence of the human liver-derived metalloprotease of the present invention (FIG. 1).

SEQ ID NO:2 shows an amino acid sequence of the rat liver-derived metalloprotease of the present invention (FIG. 6).

SEQ ID NO:3 shows an amino acid sequence of the partial peptide of the human liver-derived metalloprotease of the present invention (FIG. 2), wherein 97 amino acid residues are deleted from N-terminus of the amino acid sequence represented by SEQ ID NO:1.

SEQ ID NO:4 shows an amino acid sequence of the partial peptide of the human liver-derived metalloprotease of the present invention (FIG. 3), wherein 92 amino acid residues are deleted from N-terminus of the amino acid sequence represented by SEQ ID NO:1.

SEQ ID NO:5 shows an amino acid sequence of the partial peptide of the rat liver-derived metalloprotease of the present invention, wherein 98 amino acid residues are deleted from N-terminus of the amino acid sequence represented by SEQ ID NO:2.

SEQ ID NO:6 shows an amino acid sequence of the partial peptide of the rat liver-derived metalloprotease of the present invention, wherein 93 amino acid residues are deleted from N-terminus of the amino acid sequence represented by SEQ ID NO:2.

SEQ ID NO:7 shows a nucleotide sequence of the DNA coding for the human liver-derived metalloprotease comprising an amino acid sequence represented by SEQ ID NO:1 of the present invention.

SEQ ID NO:8 shows a nucleotide sequence of the DNA coding for the rat liver-derived metalloprotease comprising an amino acid sequence represented by SEQ ID NO:2 of the present invention.

SEQ ID NO:9 shows a nucleotide sequence of the DNA coding for the partial peptide comprising an amino acid sequence represented by SEQ ID NO:3 of the human liver-derived metalloprotease of the present invention.

SEQ ID NO:10 shows a nucleotide sequence of the DNA coding for the partial peptide comprising an amino acid sequence represented by SEQ ID NO:4 of the human liver-derived metalloprotease of the present invention.

SEQ ID NO:11 shows a nucleotide sequence of the DNA coding for the partial peptide comprising an amino acid sequence represented by SEQ ID NO:5 of the human liver-derived metalloprotease of the present invention.

SEQ ID NO:12 shows a nucleotide sequence of the DNA coding for the partial peptide comprising an amino acid sequence represented by SEQ ID NO:6 of the human liver-derived metalloprotease of the present invention.

SEQ ID NO:13 shows a nucleotide sequence of the synthetic primer used for the cloning of the DNA coding for the human liver-derived protein of the present invention in Example 1.

SEQ ID NO:14 shows a nucleotide sequence of the synthetid primer used for the cloning of the DNA coding for the rat liver-derived protein of the present invention in Example 1.

SEQ ID NO:15 shows a nucleotide sequence of the synthetic primer used for the construction of *Escherichia coli* exapression vector in Example 4.

SEQ ID NO:16 shows a nucleotide sequence of the synthetic primer used for the construction of *Escherichia coli* exapression vector in Example 4.

SEQ ID NO:17 shows a nucleotide sequence of the synthetic primer used for the cloning of the DNA coding for the rat liver-derived protein of the present invention in Example 9.

SEQ ID NO:18 shows a nucleotide sequence of the synthetic primer used for the cloning of the DNA coding for the rat liver-derived protein of the present invention in Example 9.

SEQ ID NO:19 shows a nucleotide sequence of the synthetic primer used for the cloning of the DNA coding for the rat liver-derived protein of the present invention in Example 9.

The transformant strain of *Escherichia coli*, designated DH10B/PTB1921, which is obtained in the Example 1 mentioned hereinafter, is on deposit under the terms of the Budapest Treaty from Apr. 22, 1996, with the NIBH under the Accession Number of FERM BP-5516. It is also on deposit from Apr. 19, 1996 with the IFO under the Accession Number of IFO 15950.

The transformant strain of *Escherichia coli*, designated DH10B/PTB1982, which is obtained in the Example 9 mentioned hereinafter, is on deposit under the terms of the Budapest Treaty from Apr. 9, 1997, with the NIBH under the Accession Number of FERM BP-5906. It is also on deposit from Apr. 9, 1997 with the IFO under the Accession Number of IFO 16074.

BRIEF DESCRIPTION OF DRAWINGS

FIG. 1 shows an amino acid sequence of a human liver-derived metalloprotease of the present invention.

FIG. 2 shows an amino acid sequence of a partial peptide of the human liver-derived metalloprotease of the present invention, wherein 97 amino acid residues are deleted from the N-terminus of the amino acid sequence shown in FIG. 1.

FIG. 3 shows an amino acid sequence of a partial peptide of a human liver-derived metalloprotease of the present invention, wherein 92 amino acid residues are deleted from the N-terminus of the amino acid sequence shown in FIG. 1.

BEST MODE FOR CARRYING OUT THE INVENTION

EXAMPLES

Figure 4:
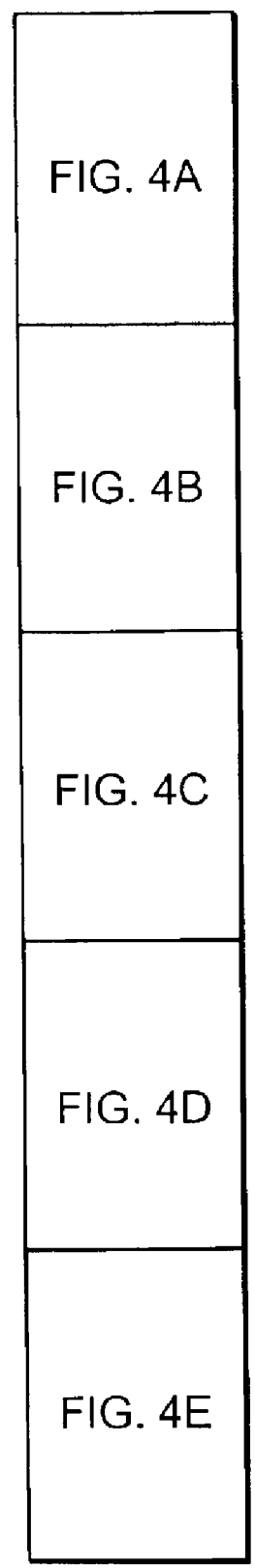
FIG. 4 shows a nucleotide sequence of a DNA encoding a human liver-derived metalloprotease of the present invention.

The following examples are intended to illustrate the present invention in further detail and should by no means be construed as defining the scope of the invention. Incidentally, the gene manipulations using *Escherichia coli* were made according to the protocol described in Molecular Cloning.

Example 1
Cloning of a Gene Coding for Human Liver-Derived Metalloprotease

The cloning of the cDNA was carried out using Gene Trapper Positive Selection System (GIBCO/BRL).

*Escherichia coli* DH12S from a human liver-derived cDNA library (GIBCO/BRL) was cultured in Terrific Broth (12 g/l bacto-tryptone (Difco), 24 g/l bacto-yeast extract (Difco), 2.3 g/l potassium dihydrogen phosphate, 12.5 g/l potassium monohydrogen phosphate) at 30° C. for 16 hours and using Qiagen Plasmid Kit (Qiagen), a plasmid cDNA library was purified and extracted. The purified plasmid cDNA library was digested with Gene II and Exo III (both from GIBCO/BRL) to construct a single-stranded cDNA library.

On the other hand, as a probe, a synthetic oligonucleotide (SEQ ID NO:13) was used for the screening of the cDNA library. The probe was labeled by biotinylating its 3'-end with TdT and biotin-14-dCTP (GIBCO/BRL). The single-stranded cDNA library was treated at 95° C. for 1 minute and, then, quenched on ice. To this was added the biotinylated probe, and hybridization was conducted at 37° C. for 1 hour and at room temperature. After hybridization, Gene Trapper Positive Selection System magnet beads (GIBCO/BRL) were added and the mixture was allowed to stand at room temperature for 30 minutes with stirring at 2-min intervals. Thereafter, the mixture was put in Gene Trapper Positive Selection System magnet track (GIBCO/BRL) and allowed to stand for 2 minutes. The supernatant was then discarded and the magnet beads were washed with Gene Trapper Positive Selection System wash buffer. This washing with the wash buffer was repeated 3 times. The beads were then placed and allowed to sit in the magnetic track and the supernatant was discarded. Then, Gene Trapper Positive Selection System elution buffer was added and the system was allowed to stand at room temperature for 5 minutes. The system was put in the magnetic track and left standing for 5 minutes, and the supernatant DNA solution was recovered.

The synthetic oligonucleotide (SEQ ID NO:13) as the primer was put in the recovered DNA solution and the system was allowed to stand at 95° C. for 1 minute. Then, Gene Trapper Positive Selection System repair enzyme was added and the mixture was allowed to stand at 70° C. for 15 minutes to synthesize a double-stranded DNA. Using an electroporation apparatus (Bio-Rad), this synthetic double-stranded DNA was introduced into *Escherichia coli* DH10B.

Using the resulting transformants and, as primers, 2 oligonucleotides (SEQ ID NO:13 and NO:14), a screening by colony PCR was carried out. A colony line of amplified fragments of 510 bp formed by PCR was selected as positive clones.

The selected *Escherichia coli* was cultured and the DNA was extracted. The reaction was carried out using ABI PRISM Dye Terminator Cycle Sequencing Ready Reaction Kit with AmpliTaq DNA polymerase FS (Perkin-Elmer) and the nucleotide sequence of the cDNA fragment was determined with 377 DNA Sequencer (Perkin-Elmer). The clone obtained was found to have the 2264 bp containing the poly(A)$^+$ chain and a sequence of 1524 bp as represented by SEQ ID NO:7. Encoded in this cDNA fragment was a novel metalloprotease consisting of 508 amino acid residues as represented by SEQ ID NO:1 and the active center histidine residue had also been conserved. The homology with the known human metalloproteases (e.g. MMP-1, MMP-2, MMP-3, MMP-7, MMP-8, MMP-9, MMP-10, MMP-11, MMP-12, MMP-13, MMP-17, MT-MMP-1, MT-MMP-2, MT-MMP-3) at the amino acid level was as low as 30 to 36%.

The plasmid pTB1921 harboring the DNA encoding the human liver-derived metalloprotease of the invention was introduced into *Escherichia coli* DH10B to obtain the transformant *Escherichia coli* DH10B/pTB1921.

Example 2
Transient Expression of the Human Liver-Derived Metalloprotease and Preparation of a Culture Supernatant The pTB1921 obtained in Example 1, which had been inserted into the expression plasmied pCMV·SPORT (GIBCO/BRL), was used for expression in animal cells. The COS-7 cell line (purchased from the Institute for Fermentation, Osaka) was cultured in serum-containing DMEM and subcultured on the day before introduction of the gene. When the culture became 50% confluent, the COS-7 cells were washed with serum-free DMEM, and 2.5 ml of serum-free medium was added. To this cell suspension was added TRANSFECTAM (Nippon Gene) containing 5 µg pTB1921, and the mixture was incubated under 5% $CO_2$ at 37° C. for 4 hours. Then, 20% bovine serum-containing DMEM (2.5 ml) was added and the mixture was further incubated for 20 hours. The medium was then replaced with serum-free DMEM and the culture supernatant was recovered 3 days later. As a control, a mock culture supernatant obtained by adding TRANSFECTAM alone in otherwise the same manner was used.

Example 3
PER Assay of the Metalloprotease Activity of the Human Liver-Derived Metalloprotease To the cell culture supernatant obtained in Example 2 was added aminophenyl-mercuric acetate (final concentration 1 mM) and the reaction was carried out at 37° C. for 30 minutes. The activity was then determined by the PER assay (F. T. Lundy et al., Electrophoresis, 16, 43, 1995). As a result, casein hydrolyzing activity which was not found in the mock culture supernatant was detected in the culture supernatant of COS-7 cells transfected with pTB1921. It was found that this activity was inhibited by o-phenanthroline.

Example 4
Construction of the *Esherichia coli* Expression Vector

To generate SphI and PstI cutting sites to cDNA encoding the human liver-derived metalloprotease of the present invention, using the pTB1921 obtained in Example 1 as the template and the following two oligonucleotides

```
                                            (SEQ ID NO:15)
5'-CCCGCATGCTACCTGTTGCTGGGCCGCTG-3'

(SEQ ID NO:16)
5'-AAGCTGCAGATCTACGGTCTTGCGCCTGCTACA-3'
``` as primers, PCR (94° C.×30 sec., 55° C.×30 sec, 72° C.×1 min., 25 cycles) was carried out in accordance with the protocol accompanying the PCR amplification kit (Takara Shuzo). After the PCR product was purified by using Spin-Bind PCR Purification System (FMC), it was subcloned into pCRII (Invitrogen). After confirmation of being free from error of the nucleotide sequence of metalloprotease cDNA, the cDNA was cut out with SphI and PstI and ligated to similarly treated pQE30 (Qiagen). Then, *Escherichia coli* JM109 (Takara Shuzo) was transfected using the ligation mixture to obtain the human liver-derived metalloprotease-expressing *Escherichia coli* JM109/pNHMB.

Example 5
Expression of the Recombinant Metalloprotease in *Escherichia coli* and its Purification Using the *Escherichia coli* JM109/pNHMB as obtained in Example 4, a recombinant metalloprotease was obtained. Its expression in *Escherichia coli* and purification were carried out in accordance with the protocol accompanying QIAexpress System (Qiagen). As a result, the objective metalloprotease of about 46 kDa was eluted with buffer E (QIAexpress System). Then, using a dialysis membrane with a cutoff molecular weight of 12000–14000 (SPECTORAPOR), the eluate was dialyzed against buffer (0.2 M Tris-HCl (pH 9.0), 3 mM 2-mercaptoethanol, 0.3 mM 2-hydroxyethyl disulfide, 2 M urea, 0.1% Triton X-100) at 4° C. for 16 hours and, then, serially against a buffer (0.05 M Tris-HCl (pH 8.0), 0.15 M NaCl, 0.1 M urea, 1 mM 2-mercaptoethanol, 0.1 mM 2-hydroxyethyl disulfide, 0.05% Triton X-100) and another buffer (0.05 M Tris-HCl (pH 8.0), 0.15 M NaCl, 0.05% Triton X-100) at 4° C. for 4 hours each. In this manner, 18.2 mg of a recombinant human liver-derived metalloprotease could be obtained from 800 ml of the *Escherichia coli* culture.

Example 6
Establishment of an Inhibitor Screening System

A 96-well plate (Fluoro B Plate, Dainippon Pharmaceutical) was filled in with 30 µL of buffer (0.25 M Tris-HCl (pH 8.0), 5 mM $CaCl_2$, 100 mM NaCl, 10 µM $ZnCl_2$) and 20 µL of the recombinant human liver-derived metalloprotease (2.4 mg/ml) obtained in Example 5. After 10 minutes of preincubation at 37° C., the enzymatic reaction was initiated by adding 100 µL of 10 µM substrate (DNP-Pro-Cha-Abu-Cys(Me)-His-Ala-Lys(N-Me-Abz)-$NH_2$; Bachem]. The reaction was conducted at 37° C. for 16 hours and, using a microplate reader (MTP-32, Corona Electronic), the intensity of fluorescence in the reaction system was measured at an exciting wavelength of 365 nm and an emission wavelength of 460 nm. Compared with the intensity of fluorescence of enzyme-free control (-20), a buffer containing the renatured recombinant metalloprotease showed a fluorescence intensity of 230. When actinonin (Peptide Institute), a metalloprotease inhibitor, was added at a varying concentration to this reaction mixture, it inhibited metalloprotease activity with a 50% inhibitory concentration of about 10 µM. It was, therefore, clear that this assay system can be used for the screening of inhibitors of the human liver-derived metalloprotease.

Example 7
Acquisition of Anti-Metalloprotease Polyclonal Antibody

The recombinant human liver-derived metalloprotease (200 µg) obtained in Example 5 was suspended in complete Freund's adjuvant and injected into a Japanese white rabbit for the first immunization dose. Then, the rabbit was boosted with a suspension of 400 µg recombinant human liver-derived metalloprotease in incomplete Freund's adjuvant 4 times at 2-week intervals. Total blood was harvested at one week after the last booster administration to obtain about 50 ml of serum.

The antibody titer was determined as follows. To a 96-well plate prepared by immobilizing 0.5 µg/well of recombinant metalloprotease and blocked with BSA, diluted rabbit serum was added and the plate was allowed to stand at room temperature for 2 hours. After washing with the PBS containing 0.1% Tween-20, anti-rabbit IgG-peroxidase (Capel) was added and the plate was allowed to stand for 2 hours. After washing, citrate-phosphate buffer containing o-phenylenediamine and hydrogen peroxide was added and a colorization reaction was carried out for 20 minutes. The reaction was stopped with 1 M sulfuric acid and using a plate reader, the colorization was read at 492 nm. As a result, an antiserum showing an antibody titer about $1\times10^4$-fold higher than that of a non-immunized rabbit was obtained.

Figure 5:
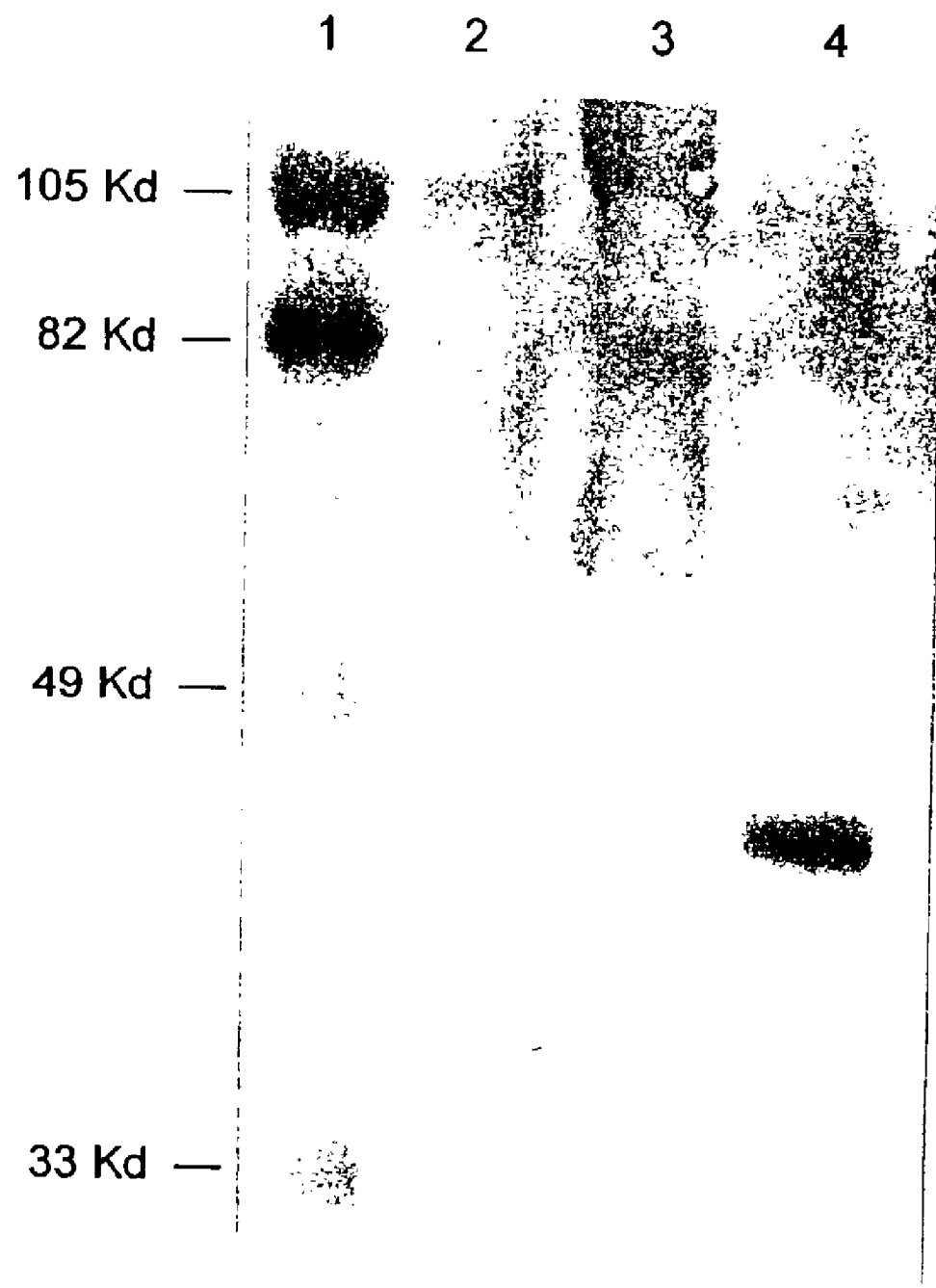
FIG. 5 shows an electrophoretogram of Western blot analysis by using a human liver-derived metalloprotease of the present invention and the antibody against the protein. The abscissa represents a number of each samples. No. 1 shows a molecular weight marker used, No. 2 shows a culture supernatant of non-infected HighFive cells, No. 3 shows a culture supernatant of HighFive cells infected with β-galactosidase-expressing recombinant virus (Invitrogen), and No. 4 shows a culture supernatant of HighFive cells infected with human liver-derived metalloprotease-expressing recombinant virus. The ordinate represents a distance of electrophoretic migration (cm).

Example 8
Expression of the Human Liver-Derived Metalloprotease in Insect Cells and Western Blotting with Anti-Metalloprotease Antibody Construction of a recombinant vaculovirus and expression in insect cells were carried out using Invitrogen's Bac-N-Blue Transfection Kit according to the accompanying protocol. The plasmid obtained by introducing metalloprotease cDNA into the SacI and PstI restriction enzyme cleavage site of the expression vector pBlueBac4 (Invitrogen) and Bac-N-Blue (Invitrogen) viral DNA were introduced into *Spodoptera frugiperda* (Sf-9) cells, in which recombination was allowed to take place. From the blue plaques, a recombinant virus containing the human liver-derived metalloprotease cDNA was picked and used to infect HighFive insect cells (Invitrogen). The culture supernatant of the above insect cells was Western-blotted with the anti-metalloprotease antibody obtained in Example 7. As the secondary antibody, anti-rabbit IgG-alkaline phosphatase conjugate was used, and as color reagents, 5-bromo-4-chloro-3-indolyl-1-phosphate and Nitro Blue Tetrazolium (both from Promega) were used. As shown in FIG. 5, a band of about 44 kb was observed only in the culture supernatant of the HighFive cells infected with metalloprotease-expressed recombinant virus. The above results indicated that the antibody prepared in Example 7 could recognize the human liver-derived metalloprotease of the present invention.

Example 9

Cloning of a Gene Coding for Rat Liver-Derived Metalloprotease

Synthetic oligonucleotide primer:

```
5'-GGCAGGGATCCAGGCTCTC-3'      (SEQ ID NO:17)

5'-TGCATCCAGGTTAGGTTC-3'       (SEQ ID NO:18)
``` prepared based on the nucleotide sequence of the cDNA coding for the human liver-derived metalloprotease obtained in Example 1 were use for PCR with rat brain and liver cDNA libraries (GIBCO/BRL) as templates. As a result, about 400 bp fragment coding for a part of the rat liver-derived metalloprotease was amplified from both rat cDNA libraries. The DNA fragment from the brain cDNA library was subcloned into pCRII (Invitrogen) and sequenced as described in Example 1. Full-length cDNA coding for the rat liver-derived metalloprotease was obtained from the rat liver cDNA library with the synthetic oligonucleotide primer: 5'-GCCGGAGCCAGAAGATGAGG-3' (SEQ ID NO:19) prepared based on the 400 bp fragment according to the method as described in the Example 1.

Figures 6, 6A, 6B, 6C, 6D, 6E:
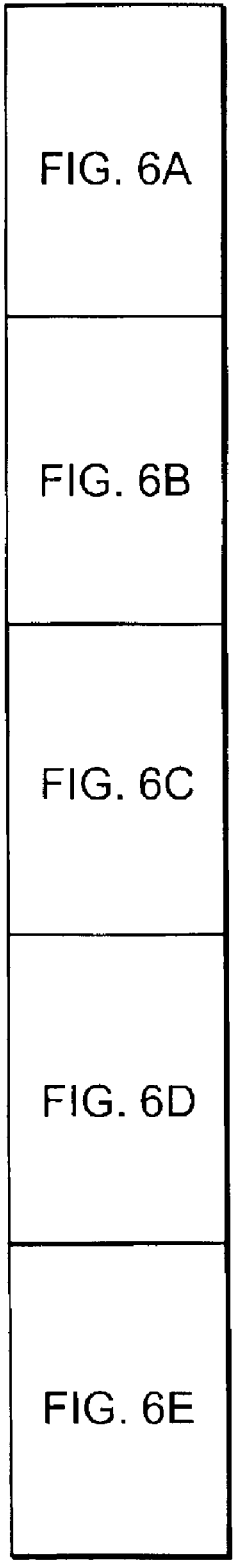
FIG. 6 shows an amino acid sequence of a rat liver-derived metalloprotease of the present invention and a nucleotide sequence of a DNA containing a DNA coding for the amino acid sequence.

The cDNA consisted of 2,049 bp and contained 1,551 bp of open reading frame coding for 517 amino acids of rat liver-derived metalloprotease and poly(A) as shown in FIG. 6. The rat liver-derived metalloprotease is 80% identical to the human liver-derived metalloprotease at the amino acid level. *Escherichia coli* DH10B was transformed with the plasmid pTB1982 comprising the cDNA coding for the rat liver-derived metalloprotease to obtain the transformant: *Escherichia coli* DH10B/pTB1982.

Industrial Applicability

The DNA coding for the protein of the present invention can be used as a therapeutic and prophylactic composition for a variety of diseases including diabetic nephropathy, glomerulonephritis, pulmonary fibrosis, hepatolienal fibrosis, hepatocirrhosis, osteopetrosis and herniated disk. The protein of the present invention is useful as a screening reagent for any compounds which activate or inhibit the function of the protein of the present invention. In addition, the antibody against the protein of the present invention specifically recognizes the protein of the present invention and can be used in the quantitative determination of the protein of the present invention in a test fluid.

What is claimed is:

1. An isolated DNA comprising a DNA selected from the group consisting of:
   (a) a DNA comprising a nucleotide sequence coding for a protein comprising the amino acid sequence set forth in SEQ ID NO: 1;
   (b) a DNA comprising the nucleotide sequence set forth in SEQ ID NO: 7; and
   (c) a DNA comprising a nucleotide sequence that hybridizes under stringent conditions comprising a salt concentration of 19 mM Na$^+$ and a temperature of 65° C. to the nucleotide sequence set forth in SEQ ID NO: 7 and that encodes a protein having a proteolytic activity that hydrolyzes casein.

2. The DNA according to claim 1 which contains a DNA comprising a nucleotide sequence coding for a protein comprising the amino acid sequence set forth in SEQ ID NO:1.

3. The DNA according to claim 1, which comprises the nucleotide sequence set forth in SEQ ID NO: 7.

4. An isolated DNA which contains a DNA comprising a nucleotide sequence coding for a metalloprotease protein having the amino acid sequence set forth in SEQ ID NO: 1, or a salt thereof.

5. The isolated DNA according to claim 4 consisting of the nucleotide sequence set forth in SEQ ID NO: 7.

6. A recombinant vector comprising the DNA according to claim 1.

7. A recombinant vector comprising the isolated DNA according to claim 4.

8. A transformed host cell comprising the recombinant vector according to claim 6.

9. A transformed host cell carrying the recombinant vector according to claim 7.

10. A process for producing a protein encoded by the DNA according to claim 1, or a salt thereof, which comprises culturing the transformed host cell according to claim 8 under conditions suitable for expression of said protein.

11. A process for producing a protein encoded by the DNA according to claim 4, or a salt thereof, comprising culturing the transformed host cell of claim 9 under conditions suitable for the expression of the protein.

* * * * *

SEQUENCE LISTING

<160> NUMBER OF SEQ ID NOS: 23

<210> SEQ ID NO 1
<211> LENGTH: 508
<212> TYPE: PRT
<213> ORGANISM: Homo sapiens

<400> SEQUENCE: 1

```
Met Asn Cys Gln Gln Leu Trp Leu Gly Phe Leu Leu Pro Met Thr Val
 1               5                  10                  15

Ser Gly Arg Val Leu Gly Leu Ala Glu Val Ala Pro Val Asp Tyr Leu
            20                  25                  30

Ser Gln Tyr Gly Tyr Leu Gln Lys Pro Leu Glu Gly Ser Asn Asn Phe
        35                  40                  45

Lys Pro Glu Asp Ile Thr Glu Ala Leu Arg Ala Phe Gln Glu Ala Ser
    50                  55                  60

Glu Leu Pro Val Ser Gly Gln Leu Asp Asp Ala Thr Arg Ala Arg Met
65                  70                  75                  80

Arg Gln Pro Arg Cys Gly Leu Glu Asp Pro Phe Asn Gln Lys Thr Leu
                85                  90                  95

Lys Tyr Leu Leu Leu Gly Arg Trp Arg Lys Lys His Leu Thr Phe Arg
            100                 105                 110

Ile Leu Asn Leu Pro Ser Thr Leu Pro Pro His Thr Ala Arg Ala Ala
        115                 120                 125
```

```
Leu Arg Gln Ala Phe Gln Asp Trp Ser Asn Val Ala Pro Leu Thr Phe
    130                 135                 140

Gln Glu Val Gln Ala Gly Ala Ala Asp Ile Arg Leu Ser Phe His Gly
145                 150                 155                 160

Arg Gln Ser Ser Tyr Cys Ser Asn Thr Phe Asp Gly Pro Gly Arg Val
                165                 170                 175

Leu Ala His Ala Asp Ile Pro Glu Leu Gly Ser Val His Phe Asp Glu
            180                 185                 190

Asp Glu Phe Trp Thr Glu Gly Thr Tyr Arg Gly Val Asn Leu Arg Ile
        195                 200                 205

Ile Ala Ala His Glu Val Gly His Ala Leu Gly Leu Gly His Ser Arg
210                 215                 220

Tyr Ser Gln Ala Leu Met Ala Pro Val Tyr Glu Gly Tyr Arg Pro His
225                 230                 235                 240

Phe Lys Leu His Pro Asp Asp Val Ala Gly Ile Gln Ala Leu Tyr Gly
                245                 250                 255

Lys Lys Ser Pro Val Ile Arg Asp Glu Glu Glu Glu Thr Glu Leu
            260                 265                 270

Pro Thr Val Pro Pro Val Pro Thr Glu Pro Ser Pro Met Pro Asp Pro
        275                 280                 285

Cys Ser Ser Glu Leu Asp Ala Met Met Leu Gly Pro Arg Gly Lys Thr
    290                 295                 300

Tyr Ala Phe Lys Gly Asp Tyr Val Trp Thr Val Ser Asp Ser Gly Pro
305                 310                 315                 320

Gly Pro Leu Phe Arg Val Ser Ala Leu Trp Glu Gly Leu Pro Gly Asn
                325                 330                 335

Leu Asp Ala Ala Val Tyr Ser Pro Arg Thr Gln Trp Ile His Phe Phe
            340                 345                 350

Lys Gly Asp Lys Val Trp Arg Tyr Ile Asn Phe Lys Met Ser Pro Gly
        355                 360                 365

Phe Pro Lys Lys Leu Asn Arg Val Glu Pro Asn Leu Asp Ala Ala Leu
    370                 375                 380

Tyr Trp Pro Leu Asn Gln Lys Val Phe Leu Phe Lys Gly Ser Gly Tyr
385                 390                 395                 400

Trp Gln Trp Asp Glu Leu Ala Arg Thr Asp Phe Ser Ser Tyr Pro Lys
                405                 410                 415

Pro Ile Lys Gly Leu Phe Thr Gly Val Pro Asn Gln Pro Ser Ala Ala
            420                 425                 430

Met Ser Trp Gln Asp Gly Arg Val Tyr Phe Phe Lys Gly Lys Val Tyr
        435                 440                 445

Trp Arg Leu Asn Gln Gln Leu Arg Val Glu Lys Gly Tyr Pro Arg Asn
    450                 455                 460

Ile Ser His Asn Trp Met His Cys Arg Pro Arg Thr Ile Asp Thr Thr
465                 470                 475                 480

Pro Ser Gly Gly Asn Thr Thr Pro Ser Gly Thr Gly Ile Thr Leu Asp
                485                 490                 495

Thr Thr Leu Ser Ala Thr Glu Thr Thr Phe Glu Tyr
            500                 505

<210> SEQ ID NO 2
<211> LENGTH: 517
<212> TYPE: PRT
<213> ORGANISM: Rattus sp.
```

```
<400> SEQUENCE: 2

Met Asp Trp Gln Gln Leu Trp Leu Ala Phe Leu Leu Pro Val Thr Val
 1               5                  10                  15

Ser Gly Arg Ala Leu Gly Pro Ala Glu Lys Glu Ala Val Val Asp Tyr
            20                  25                  30

Leu Leu Gln Tyr Gly Tyr Leu Gln Lys Pro Leu Glu Gly Ala Asp Asp
        35                  40                  45

Phe Arg Leu Glu Asp Ile Thr Glu Ala Leu Arg Thr Phe Gln Glu Ala
50                  55                  60

Ser Glu Leu Pro Val Ser Gly Gln Met Asp Asp Ala Thr Arg Ala Arg
65                  70                  75                  80

Met Lys Gln Pro Arg Cys Gly Leu Glu Asp Pro Phe Asn Gln Lys Thr
                85                  90                  95

Leu Lys Tyr Leu Leu Leu Gly His Trp Arg Lys His Leu Thr Phe
            100                 105                 110

Arg Ile Leu Asn Val Pro Ser Thr Leu Ser Pro Ser Arg Val Arg Ala
        115                 120                 125

Ala Leu His Gln Ala Phe Lys Tyr Trp Ser Asn Val Ala Pro Leu Thr
    130                 135                 140

Phe Arg Glu Val Lys Ala Gly Trp Ala Asp Ile Arg Leu Ser Phe His
145                 150                 155                 160

Gly Arg Gln Ser Pro Tyr Cys Ser Asn Ser Phe Asp Gly Pro Gly Lys
                165                 170                 175

Val Leu Ala His Ala Asp Val Pro Glu Leu Gly Ser Val His Phe Asp
            180                 185                 190

Asn Asp Glu Phe Trp Thr Glu Gly Thr Tyr Gln Gly Val Asn Leu Arg
        195                 200                 205

Ile Ile Ala Ala His Glu Val Gly His Ala Leu Gly Leu Gly His Ser
    210                 215                 220

Arg Tyr Thr Gln Ala Leu Met Ala Pro Val Tyr Ala Gly Tyr Gln Pro
225                 230                 235                 240

Tyr Phe Arg Leu His Pro Asp Asp Val Ala Gly Ile Gln Ala Leu Tyr
                245                 250                 255

Gly Lys Arg Arg Pro Glu Pro Glu Asp Glu Glu Glu Val Glu Met
            260                 265                 270

His Thr Val Ser Thr Val Thr Thr Lys Pro Ser Pro Met Pro Asn Pro
        275                 280                 285

Cys Ser Ser Glu Val Asp Ala Met Met Leu Gly Pro Arg Gly Lys Thr
    290                 295                 300

Tyr Ala Phe Lys Gly Asp Tyr Val Trp Thr Val Thr Asp Ser Gly Pro
305                 310                 315                 320

Gly Pro Leu Phe Arg Val Ser Ala Leu Trp Glu Gly Leu Pro Gly Asn
                325                 330                 335

Leu Asp Ala Ala Val Tyr Ser Pro Arg Thr Gln Arg Thr His Phe Phe
            340                 345                 350

Lys Gly Asn Lys Val Trp Arg Tyr Val Asp Phe Lys Leu Ser Pro Gly
        355                 360                 365

Phe Pro Met Lys Leu Asn Arg Val Glu Pro Asn Leu Asp Ala Ala Leu
    370                 375                 380

Tyr Trp Pro Val Asn Gln Lys Val Phe Leu Phe Lys Gly Ser Gly Tyr
385                 390                 395                 400

Trp Gln Trp Asp Glu Leu Thr Arg Thr Asp Leu Ser Arg Tyr Pro Lys
                405                 410                 415
```

```
Pro Ile Lys Glu Leu Phe Thr Gly Val Pro Asp Gln Pro Ser Ala Ala
            420                 425                 430

Met Ser Trp Gln Asp Gly Gln Val Tyr Phe Phe Lys Gly Lys Glu Tyr
            435                 440                 445

Trp Arg Leu Asn Gln Gln Leu Arg Val Ala Lys Gly Tyr Pro Arg Asn
            450                 455                 460

Thr Thr His Trp Met His Cys Ser Pro Arg Thr Pro Asp Thr Asn Ser
465                 470                 475                 480

Leu Thr Gly Asp Val Thr Thr Pro Ala Thr Val Glu Ser Val Leu Asp
                    485                 490                 495

Val Pro Ser Ala Thr Asp Ala Ala Ser Leu Ser Ser Ser Ala Asn Val
            500                 505                 510

Thr Leu Leu Gly Ala
            515

<210> SEQ ID NO 3
<211> LENGTH: 411
<212> TYPE: PRT
<213> ORGANISM: Homo sapiens

<400> SEQUENCE: 3

Tyr Leu Leu Leu Gly Arg Trp Arg Lys Lys His Leu Thr Phe Arg Ile
1               5                   10                  15

Leu Asn Leu Pro Ser Thr Leu Pro Pro His Thr Ala Arg Ala Ala Leu
            20                  25                  30

Arg Gln Ala Phe Gln Asp Trp Ser Asn Val Ala Pro Leu Thr Phe Gln
        35                  40                  45

Glu Val Gln Ala Gly Ala Ala Asp Ile Arg Leu Ser Phe His Gly Arg
    50                  55                  60

Gln Ser Ser Tyr Cys Ser Asn Thr Phe Asp Gly Pro Gly Arg Val Leu
65                  70                  75                  80

Ala His Ala Asp Ile Pro Glu Leu Gly Ser Val His Phe Asp Glu Asp
                85                  90                  95

Glu Phe Trp Thr Glu Gly Thr Tyr Arg Gly Val Asn Leu Arg Ile Ile
            100                 105                 110

Ala Ala His Glu Val Gly His Ala Leu Gly Leu Gly His Ser Arg Tyr
        115                 120                 125

Ser Gln Ala Leu Met Ala Pro Val Tyr Glu Gly Tyr Arg Pro His Phe
130                 135                 140

Lys Leu His Pro Asp Asp Val Ala Gly Ile Gln Ala Leu Tyr Gly Lys
145                 150                 155                 160

Lys Ser Pro Val Ile Arg Asp Glu Glu Glu Glu Thr Glu Leu Pro
                165                 170                 175

Thr Val Pro Pro Val Pro Thr Glu Pro Ser Pro Met Pro Asp Pro Cys
            180                 185                 190

Ser Ser Glu Leu Asp Ala Met Met Leu Gly Pro Arg Gly Lys Thr Tyr
        195                 200                 205

Ala Phe Lys Gly Asp Tyr Val Trp Thr Val Ser Asp Ser Gly Pro Gly
    210                 215                 220

Pro Leu Phe Arg Val Ser Ala Leu Trp Glu Gly Leu Pro Gly Asn Leu
225                 230                 235                 240

Asp Ala Ala Val Tyr Ser Pro Arg Thr Gln Trp Ile His Phe Phe Lys
                245                 250                 255

Gly Asp Lys Val Trp Arg Tyr Ile Asn Phe Lys Met Ser Pro Gly Phe
```

```
                 260                 265                 270
Pro Lys Lys Leu Asn Arg Val Glu Pro Asn Leu Asp Ala Ala Leu Tyr
            275                 280                 285

Trp Pro Leu Asn Gln Lys Val Phe Leu Phe Lys Gly Ser Gly Tyr Trp
        290                 295                 300

Gln Trp Asp Glu Leu Ala Arg Thr Asp Phe Ser Ser Tyr Pro Lys Pro
305                 310                 315                 320

Ile Lys Gly Leu Phe Thr Gly Val Pro Asn Gln Pro Ser Ala Ala Met
                325                 330                 335

Ser Trp Gln Asp Gly Arg Val Tyr Phe Phe Lys Gly Lys Val Tyr Trp
            340                 345                 350

Arg Leu Asn Gln Gln Leu Arg Val Glu Lys Gly Tyr Pro Arg Asn Ile
        355                 360                 365

Ser His Asn Trp Met His Cys Arg Pro Arg Thr Ile Asp Thr Thr Pro
    370                 375                 380

Ser Gly Gly Asn Thr Thr Pro Ser Gly Thr Gly Ile Thr Leu Asp Thr
385                 390                 395                 400

Thr Leu Ser Ala Thr Glu Thr Thr Phe Glu Tyr
                405                 410

<210> SEQ ID NO 4
<211> LENGTH: 416
<212> TYPE: PRT
<213> ORGANISM: Homo sapiens

<400> SEQUENCE: 4

Gln Lys Thr Leu Lys Tyr Leu Leu Gly Arg Trp Arg Lys Lys His
  1               5                  10                  15

Leu Thr Phe Arg Ile Leu Asn Leu Pro Ser Thr Leu Pro Pro His Thr
             20                  25                  30

Ala Arg Ala Ala Leu Arg Gln Ala Phe Gln Asp Trp Ser Asn Val Ala
         35                  40                  45

Pro Leu Thr Phe Gln Glu Val Gln Ala Gly Ala Ala Asp Ile Arg Leu
     50                  55                  60

Ser Phe His Gly Arg Gln Ser Ser Tyr Cys Ser Asn Thr Phe Asp Gly
 65                  70                  75                  80

Pro Gly Arg Val Leu Ala His Ala Asp Ile Pro Glu Leu Gly Ser Val
                 85                  90                  95

His Phe Asp Glu Asp Glu Phe Trp Thr Glu Gly Thr Tyr Arg Gly Val
            100                 105                 110

Asn Leu Arg Ile Ile Ala Ala His Glu Val Gly His Ala Leu Gly Leu
        115                 120                 125

Gly His Ser Arg Tyr Ser Gln Ala Leu Met Ala Pro Val Tyr Glu Gly
    130                 135                 140

Tyr Arg Pro His Phe Lys Leu His Pro Asp Asp Val Ala Gly Ile Gln
145                 150                 155                 160

Ala Leu Tyr Gly Lys Lys Ser Pro Val Ile Arg Asp Glu Glu Glu Glu
                165                 170                 175

Glu Thr Glu Leu Pro Thr Val Pro Pro Val Pro Thr Glu Pro Ser Pro
            180                 185                 190

Met Pro Asp Pro Cys Ser Ser Glu Leu Asp Ala Met Met Leu Gly Pro
        195                 200                 205

Arg Gly Lys Thr Tyr Ala Phe Lys Gly Asp Tyr Val Trp Thr Val Ser
    210                 215                 220
```

-continued

```
Asp Ser Gly Pro Gly Pro Leu Phe Arg Val Ser Ala Leu Trp Glu Gly
225                 230                 235                 240

Leu Pro Gly Asn Leu Asp Ala Ala Val Tyr Ser Pro Arg Thr Gln Trp
            245                 250                 255

Ile His Phe Lys Gly Asp Lys Val Trp Arg Tyr Ile Asn Phe Lys
        260                 265                 270

Met Ser Pro Gly Phe Pro Lys Lys Leu Asn Arg Val Glu Pro Asn Leu
    275                 280                 285

Asp Ala Ala Leu Tyr Trp Pro Leu Asn Gln Lys Val Phe Leu Phe Lys
290                 295                 300

Gly Ser Gly Tyr Trp Gln Trp Asp Glu Leu Ala Arg Thr Asp Phe Ser
305                 310                 315                 320

Ser Tyr Pro Lys Pro Ile Lys Gly Leu Phe Thr Gly Val Pro Asn Gln
            325                 330                 335

Pro Ser Ala Ala Met Ser Trp Gln Asp Gly Arg Val Tyr Phe Phe Lys
            340                 345                 350

Gly Lys Val Tyr Trp Arg Leu Asn Gln Gln Leu Arg Val Glu Lys Gly
        355                 360                 365

Tyr Pro Arg Asn Ile Ser His Asn Trp Met His Cys Arg Pro Arg Thr
370                 375                 380

Ile Asp Thr Thr Pro Ser Gly Gly Asn Thr Thr Pro Ser Gly Thr Gly
385                 390                 395                 400

Ile Thr Leu Asp Thr Thr Leu Ser Ala Thr Glu Thr Thr Phe Glu Tyr
                405                 410                 415

<210> SEQ ID NO 5
<211> LENGTH: 419
<212> TYPE: PRT
<213> ORGANISM: Rattus sp.

<400> SEQUENCE: 5

Tyr Leu Leu Leu Gly His Trp Arg Lys Lys His Leu Thr Phe Arg Ile
1               5                   10                  15

Leu Asn Val Pro Ser Thr Leu Ser Pro Ser Arg Val Arg Ala Ala Leu
            20                  25                  30

His Gln Ala Phe Lys Tyr Trp Ser Asn Val Ala Pro Leu Thr Phe Arg
        35                  40                  45

Glu Val Lys Ala Gly Trp Ala Asp Ile Arg Leu Ser Phe His Gly Arg
    50                  55                  60

Gln Ser Pro Tyr Cys Ser Asn Ser Phe Asp Gly Pro Gly Lys Val Leu
65                  70                  75                  80

Ala His Ala Asp Val Pro Glu Leu Gly Ser Val His Phe Asp Asn Asp
                85                  90                  95

Glu Phe Trp Thr Glu Gly Thr Tyr Gln Gly Val Asn Leu Arg Ile Ile
            100                 105                 110

Ala Ala His Glu Val Gly His Ala Leu Gly Leu Gly His Ser Arg Tyr
        115                 120                 125

Thr Gln Ala Leu Met Ala Pro Val Tyr Ala Gly Tyr Gln Pro Tyr Phe
    130                 135                 140

Arg Leu His Pro Asp Asp Val Ala Gly Ile Gln Ala Leu Tyr Gly Lys
145                 150                 155                 160

Arg Arg Pro Glu Pro Glu Asp Glu Glu Glu Val Glu Met His Thr
                165                 170                 175

Val Ser Thr Val Thr Thr Lys Pro Ser Pro Met Pro Asn Pro Cys Ser
            180                 185                 190
```

-continued

Ser Glu Val Asp Ala Met Met Leu Gly Pro Arg Gly Lys Thr Tyr Ala
        195                 200                 205

Phe Lys Gly Asp Tyr Val Trp Thr Val Thr Asp Ser Gly Pro Gly Pro
    210                 215                 220

Leu Phe Arg Val Ser Ala Leu Trp Glu Gly Leu Pro Gly Asn Leu Asp
225                 230                 235                 240

Ala Ala Val Tyr Ser Pro Arg Thr Gln Arg Thr His Phe Phe Lys Gly
                245                 250                 255

Asn Lys Val Trp Arg Tyr Val Asp Phe Lys Leu Ser Pro Gly Phe Pro
            260                 265                 270

Met Lys Leu Asn Arg Val Glu Pro Asn Leu Asp Ala Ala Leu Tyr Trp
        275                 280                 285

Pro Val Asn Gln Lys Val Phe Leu Phe Lys Gly Ser Gly Tyr Trp Gln
    290                 295                 300

Trp Asp Glu Leu Thr Arg Thr Asp Leu Ser Arg Tyr Pro Lys Pro Ile
305                 310                 315                 320

Lys Glu Leu Phe Thr Gly Val Pro Asp Gln Pro Ser Ala Ala Met Ser
                325                 330                 335

Trp Gln Asp Gly Gln Val Tyr Phe Phe Lys Gly Lys Glu Tyr Trp Arg
            340                 345                 350

Leu Asn Gln Gln Leu Arg Val Ala Lys Gly Tyr Pro Arg Asn Thr Thr
        355                 360                 365

His Trp Met His Cys Ser Pro Arg Thr Pro Asp Thr Asn Ser Leu Thr
    370                 375                 380

Gly Asp Val Thr Thr Pro Ala Thr Val Glu Ser Val Leu Asp Val Pro
385                 390                 395                 400

Ser Ala Thr Asp Ala Ala Ser Leu Ser Ser Ala Asn Val Thr Leu
                405                 410                 415

Leu Gly Ala

<210> SEQ ID NO 6
<211> LENGTH: 424
<212> TYPE: PRT
<213> ORGANISM: Rattus sp.

<400> SEQUENCE: 6

Gln Lys Thr Leu Lys Tyr Leu Leu Leu Gly His Trp Arg Lys Lys His
1               5                   10                  15

Leu Thr Phe Arg Ile Leu Asn Val Pro Ser Thr Leu Ser Pro Ser Arg
            20                  25                  30

Val Arg Ala Ala Leu His Gln Ala Phe Lys Tyr Trp Ser Asn Val Ala
        35                  40                  45

Pro Leu Thr Phe Arg Glu Val Lys Ala Gly Trp Ala Asp Ile Arg Leu
    50                  55                  60

Ser Phe His Gly Arg Gln Ser Pro Tyr Cys Ser Asn Ser Phe Asp Gly
65                  70                  75                  80

Pro Gly Lys Val Leu Ala His Ala Asp Val Pro Glu Leu Gly Ser Val
                85                  90                  95

His Phe Asp Asn Asp Glu Phe Trp Thr Glu Gly Thr Tyr Gln Gly Val
            100                 105                 110

Asn Leu Arg Ile Ile Ala Ala His Glu Val Gly His Ala Leu Gly Leu
        115                 120                 125

Gly His Ser Arg Tyr Thr Gln Ala Leu Met Ala Pro Val Tyr Ala Gly
    130                 135                 140

Tyr Gln Pro Tyr Phe Arg Leu His Pro Asp Asp Val Ala Gly Ile Gln
145                 150                 155                 160

Ala Leu Tyr Gly Lys Arg Pro Glu Pro Glu Asp Glu Glu Glu
            165                 170                 175

Val Glu Met His Thr Val Ser Thr Val Thr Lys Pro Ser Pro Met
                180                 185                 190

Pro Asn Pro Cys Ser Ser Glu Val Asp Ala Met Met Leu Gly Pro Arg
            195                 200                 205

Gly Lys Thr Tyr Ala Phe Lys Gly Asp Tyr Val Trp Thr Val Thr Asp
            210                 215                 220

Ser Gly Pro Gly Pro Leu Phe Arg Val Ser Ala Leu Trp Glu Gly Leu
225                 230                 235                 240

Pro Gly Asn Leu Asp Ala Ala Val Tyr Ser Pro Arg Thr Gln Arg Thr
                245                 250                 255

His Phe Phe Lys Gly Asn Lys Val Trp Arg Tyr Val Asp Phe Lys Leu
                260                 265                 270

Ser Pro Gly Phe Pro Met Lys Leu Asn Arg Val Glu Pro Asn Leu Asp
            275                 280                 285

Ala Ala Leu Tyr Trp Pro Val Asn Gln Lys Val Phe Leu Phe Lys Gly
            290                 295                 300

Ser Gly Tyr Trp Gln Trp Asp Glu Leu Thr Arg Thr Asp Leu Ser Arg
305                 310                 315                 320

Tyr Pro Lys Pro Ile Lys Glu Leu Phe Thr Gly Val Pro Asp Gln Pro
                325                 330                 335

Ser Ala Ala Met Ser Trp Gln Asp Gly Gln Val Tyr Phe Phe Lys Gly
            340                 345                 350

Lys Glu Tyr Trp Arg Leu Asn Gln Gln Leu Arg Val Ala Lys Gly Tyr
            355                 360                 365

Pro Arg Asn Thr Thr His Trp Met His Cys Ser Pro Arg Thr Pro Asp
370                 375                 380

Thr Asn Ser Leu Thr Gly Asp Val Thr Thr Pro Ala Thr Val Glu Ser
385                 390                 395                 400

Val Leu Asp Val Pro Ser Ala Thr Asp Ala Ala Ser Leu Ser Ser Ser
                405                 410                 415

Ala Asn Val Thr Leu Leu Gly Ala
            420

<210> SEQ ID NO 7
<211> LENGTH: 1524
<212> TYPE: DNA
<213> ORGANISM: Homo sapiens

<400> SEQUENCE: 7
atgaactgcc agcagctgtg gctgggcttc ctactcccca tgacagtctc aggccgggtc     60
ctggggcttg cagaggtggc gcccgtggac tacctgtcac aatatgggta cctacagaag    120
cctctagaag gatctaataa cttcaagcca gaagatatca ccgaggctct gagagctttt    180
caggaagcat ctgaacttcc agtctcaggt cagctggatg atgccacaag ggcccgcatg    240
aggcagcctc gttgtggcct agaggatccc ttcaaccaga gacccttaa atacctgttg    300 ctgggccgct ggagaaagaa gcacctgact ttccgcatct tgaacctgcc ctccaccctt    360
ccaccccaca cagcccgggc agccctgcgt caagccttcc aggactggag caatgtggct    420
cccttgacct tccaagaggt gcaggctggt gcggctgaca tccgcctctc cttccatggc    480

-continued

```
cgccaaagct cgtactgttc caatactttt gatgggcctg ggagagttct ggcccatgcc      540
gacatcccag agctgggcag tgtgcacttc gacgaagacg agttctggac tgaggggacc      600
taccgtgggg tgaacctgcg catcattgca gcccatgaag tgggccatgc tctgggctt      660 gggcactccc gatattccca ggccctcatg gccccagtct acgagggcta ccggccccac      720
tttaagctgc acccagatga tgtggcaggg atccaggctc tctatggcaa gaagagtcca      780
gtgataaggg atgaggaaga agaagagaca gagctgccca ctgtgccccc agtgcccaca      840
gaacccagtc ccatgccaga cccttgcagt agtgaactgg atgccatgat gctgggccc       900 cgtgggaaga cctatgcttt caaggggac tatgtgtgga ctgtatcaga ttcaggaccg       960
ggccccttgt tccgagtgtc tgcccttgg gagggctcc ccggaaacct ggatgctgct       1020
gtctactcgc ctcgaacaca atggattcac ttctttaagg gagacaaggt gtggcgctac      1080
attaatttca agatgtctcc tggcttcccc aagaagctga atagggtaga acctaacctg      1140
gatgcagctc tctattggcc tctcaaccaa aaggtgttcc tctttaaggg ctccgggtac      1200
tggcagtggg acgagctagc ccgaactgac ttcagcagct accccaaacc aatcaagggt      1260
ttgtttacgg gagtgccaaa ccagcccctg gctgctatga gttggcaaga tggccgagtc      1320
tacttcttca agggcaaagt ctactggcgc ctcaaccagc agcttcgagt agagaaaggc      1380
tatcccagaa atatttccca caactggatg cactgtcgtc cccggactat agacactacc      1440
ccatcaggtg ggaataccac tccctcaggt acgggcataa ccttggatac cactctctca      1500
gccacagaaa ccacgtttga atac                                            1524
```

<210> SEQ ID NO 8
<211> LENGTH: 1551
<212> TYPE: DNA
<213> ORGANISM: Rattus sp.

<400> SEQUENCE: 8

```
atggactggc agcagctgtg gctggccttc ttacttcctg tgacagtctc aggccgggct       60
ctggggcctg cagagaagga ggcggtggtg gattacctgt tgcagtatgg gtatctacag      120
aaacctctgg aaggagctga tgacttcagg ctagaagata tcacagaggc tctaagaact      180
ttccaggaag catctgaact gcctgttttcc ggtcagatgg atgatgccac aagggcccgt      240
atgaagcagc cccgttgtgg cctggaggat cctttcaacc agaagactct gaaatacctg      300
cttctgggcc actggagaaa gaagcacttg acattccgca tcttgaacgt gccctccacc      360 ctctcacccct ccagagtccg agcagccctg catcaagcct ttaagtattg gagcaatgta      420 gccccctga ccttccggga ggtgaaagct ggttgggctg atatccgcct ctcgttccat       480
ggccgccaaa gccatactg ctccaacagc tttgatgggc tgggaaggt cctggccat       540 gctgacgtcc cagagcttgg cagtgtacac ttcgataacg atgaattctg gaccgagggc      600
acctaccagg gagtgaacct acgcatcatt gcggcccatg aggtgggcca cgccctggga      660
cttgggcatt cccgatatac ccaggcactc atggcgcctg tttacgctgg ctaccagccc      720
tacttcaggc tgcatccgga tgatgtgca gggatccagg cgctctatgg caagaggagg      780
ccggagccag aagatgagga ggaagaggtg gagatgcaca ctgtgtcaac agtgaccaca      840
aaacccagtc ccatgccaaa cccctgcagc agtgaagtgg atgccatgat gctagggcct      900
cgggggaaga cctatgcttt caagggtgac tatgtgtgga ctgtaacaga ttcagggcca      960
gggcccttgt tccgagtgtc tgcccttgg gagggcttcc ctggaaacct ggatgctgct      1020
gtctactctc cccggacaca gcggactcat ttcttcaagg gaaacaaggt gtggcggtat     1080
```

-continued

```
gtggatttca agttgtctcc tggctttccc atgaaactca acagagtgga acccaaccta      1140
gatgcagctc tctattggcc tgttaatcag aaggtgttcc ttttttaaggg ctcaggatac     1200 tggcaatggg atgaactgac cagaactgac ctcagtcgct accccaaacc aatcaaggaa      1260
cttttcactg gagtgccaga ccaaccctca gcagctatga gctggcaaga tggccaagtc      1320
tacttcttca agggcaaaga gtactggcgc cttaaccagc aacttcgagt ggcaaagggc      1380
tatcccagaa atacgacaca ctggatgcac tgtagtcctc ggactccaga cactaactca      1440
ttaactgggg atgtgaccac tcctgcaacc gtggaatcag tcttggatgt tccctctgcc      1500
acagacgctg cctccctctc atcctcagct aatgtcacct tgctagggcc c               1551
```

<210> SEQ ID NO 9
<211> LENGTH: 1233
<212> TYPE: DNA
<213> ORGANISM: Homo sapiens

<400> SEQUENCE: 9

```
tacctgttgc tgggccgctg gagaaagaag cacctgactt ccgcatctt gaacctgccc       60 tccacccttc caccccacac agcccgggca gccctgcgtc aagccttcca ggactggagc      120
aatgtggctc ccttgacctt ccaagaggtg caggctggtg cggctgacat ccgcctctcc      180
ttccatggcc gccaaagctc gtactgttcc aatacttttg atgggcctgg agagttctg       240 gcccatgccg acatcccaga gctgggcagt gtgcacttcg acgaagacga gttctggact      300
gaggggacct accgtgggt gaacctgcgc atcattgcag cccatgaagt gggccatgct       360
ctggggcttg ggcactcccg atattccccag gccctcatgg ccccagtcta cgagggctac    420 cggcccccact ttaagctgca cccagatgat gtggcaggga tccaggctct ctatggcaag    480
aagagtccag tgataaggga tgaggaagaa aagagacag agctgccac tgtgccccca        540 gtgcccacag aacccagtcc catgccagac ccttgcagta gtgaactgga tgccatgatg      600
ctggggcccc gtgggaagac ctatgctttc aaggggact atgtgtggac tgtatcagat       660
tcaggaccgg gccccttgtt ccgagtgtct gccctttggg aggggctccc cggaaacctg      720
gatgctgctg tctactcgcc tcgaacacaa tggattcact tctttaaggg agacaaggtg      780
tggcgctaca ttaatttcaa gatgtctcct ggcttcccca gaagctgaa tagggtagaa       840 cctaacctgg atgcagctct ctattggcct ctcaaccaaa aggtgttcct ctttaagggc      900
tccgggtact ggcagtggga cgagctagcc gaactgact tcagcagcta ccccaaacca      960
atcaagggtt tgtttacggg agtgccaaac cagccctcgg ctgctatgag ttggcaagat     1020
ggccgagtct acttcttcaa gggcaaagtc tactggcgcc tcaaccagca gcttcgagta    1080
gagaaaggct atcccagaaa tatttcccac aactggatgc actgtcgtcc ccggactata    1140
gacactaccc catcaggtgg gaataccact ccctcaggta cgggcataac cttggatacc    1200
actctctcag ccacagaaac cacgtttgaa tac                                   1233
```

<210> SEQ ID NO 10
<211> LENGTH: 1248
<212> TYPE: DNA
<213> ORGANISM: Homo sapiens

<400> SEQUENCE: 10

```
cagaagaccc ttaaatacct gttgctgggc cgctggagaa agaagcacct gactttccgc      60
atcttgaacc tgcctccac ccttccaccc cacacagccc gggcagccct gcgtcaagcc      120
```

-continued

| | |
|---|---|
| ttccaggact ggagcaatgt ggctcccttg accttccaag aggtgcaggc tggtgcggct | 180 |
| gacatccgcc tctccttcca tggccgccaa agctcgtact gttccaatac ttttgatggg | 240 |
| cctgggagag ttctggccca tgccgacatc ccagagctgg gcagtgtgca cttcgacgaa | 300 |
| gacgagttct ggactgaggg gacctaccgt ggggtgaacc tgcgcatcat tgcagcccat | 360 |
| gaagtgggcc atgctctggg gcttgggcac tcccgatatt cccaggccct catggcccca | 420 |
| gtctacgagg gctaccggcc ccactttaag ctgcacccag atgatgtggc agggatccag | 480 |
| gctctctatg caagaagag tccagtgata agggatgagg aagaagaaga gacagagctg | 540 |
| cccactgtgc ccccagtgcc cacagaaccc agtcccatgc cagaccccttg cagtagtgaa | 600 |
| ctggatgcca tgatgctggg gccccgtggg aagacctatg ctttcaaggg ggactatgtg | 660 |
| tggactgtat cagattcagg accgggcccc ttgttccgag tgtctgccct ttgggagggg | 720 |
| ctccccggaa acctggatgc tgctgtctac tcgcctcgaa cacaatggat tcacttcttt | 780 |
| aagggagaca aggtgtggcg ctacattaat ttcaagatgt ctcctggctt ccccaagaag | 840 |
| ctgaataggg tagaacctaa cctggatgca gctctctatt ggcctctcaa ccaaaaggtg | 900 |
| ttcctctttta agggctccgg gtactggcag tgggacgagc tagcccgaac tgacttcagc | 960 |
| agctacccca aaccaatcaa gggtttgttt acgggagtgc caaaccagcc ctcggctgct | 1020 |
| atgagttggc aagatggccg agtctacttc ttcaagggca agtctactg gcgcctcaac | 1080 |
| cagcagcttc gagtagagaa aggctatccc agaaatattt cccacaactg gatgcactgt | 1140 |
| cgtcccggga ctatagacac tacccccatca ggtgggaata ccactccctc aggtacgggc | 1200 |
| ataaccttgg ataccactct ctcagccaca gaaaccacgt ttgaatac | 1248 |

<210> SEQ ID NO 11
<211> LENGTH: 1257
<212> TYPE: DNA
<213> ORGANISM: Homo sapiens

<400> SEQUENCE: 11

| | |
|---|---|
| tacctgcttc tgggccactg gagaaagaag cacttgacat tccgcatctt gaacgtgccc | 60 |
| tccaccctct caccctccag agtccgagca gccctgcatc aagcctttaa gtattggagc | 120 |
| aatgtagccc cctgaccttt ccgggaggtg aaagctggtt gggctgatat ccgcctctcg | 180 |
| ttccatggcc gccaaagccc atactgctcc aacagctttg atgggcctgg aaggtcctg | 240 |
| gcccatgctg acgtcccaga gcttggcagt gtacacttcg ataacgatga attctggacc | 300 |
| gagggcacct accaggagt gaacctacgc atcattgcgg cccatgaggt gggccacgcc | 360 |
| ctggacttg gcattcccg atatacccag gcactcatgg cgcctgttta cgctggctac | 420 |
| cagccctact tcaggctgca tccggatgat gtggcaggga tccaggcgct ctatggcaag | 480 |
| aggaggccgg agccagaaga tgaggaggaa gaggtggaga tgcacactgt gtcaacagtg | 540 |
| accacaaaac ccagtcccat gccaaacccc tgcagcagtg aagtggatgc catgatgcta | 600 |
| gggcctcggg ggaagaccta tgctttcaag ggtgactatg tgtggactgt aacagattca | 660 |
| gggccagggc ccttgttccg agtgtctgcc ctttgggagg gcttcctgg aaacctggat | 720 |
| gctgctgtct actctccccg acacagcgg actcatttct tcaagggaaa caaggtgtgg | 780 |
| cggtatgtgg atttcaagtt gtctcctggc tttcccatga actcaacag agtggaaccc | 840 |
| aacctagatg cagctctcta ttggcctgtt aatcagaagg tgttccttttt taagggctca | 900 |
| ggatactggc aatgggatga actgaccaga actgacctca gtcgctaccc caaaccaatc | 960 |
| aaggaacttt tcactggagt gccagaccaa ccctcagcag ctatgagctg gcaagatggc | 1020 |

-continued

```
caagtctact tcttcaaggg caaagagtac tggcgcctta accagcaact tcgagtggca      1080
aagggctatc ccagaaatac gacacactgg atgcactgta gtcctcggac tccagacact      1140
aactcattaa ctggggatgt gaccactcct gcaaccgtgg aatcagtctt ggatgttccc      1200
tctgccacag acgctgcctc cctctcatcc tcagctaatg tcaccttgct aggggcc        1257
```

<210> SEQ ID NO 12
<211> LENGTH: 1272
<212> TYPE: DNA
<213> ORGANISM: Homo sapiens

<400> SEQUENCE: 12

```
cagaagactc tgaaatacct gcttctgggc cactggagaa agaagcactt gacattccgc        60
atcttgaacg tgccctccac cctctcaccc tccagagtcc gagcagccct gcatcaagcc       120
tttaagtatt ggagcaatgt agcccccctg accttcgggg aggtgaaagc tggttgggct       180
gatatccgcc tctcgttcca tggccgccaa agcccatact gctccaacag ctttgatggg       240
cctgggaagg tcctggccca tgctgacgtc ccagagcttg gcagtgtaca cttcgataac       300
gatgaattct ggaccgaggg cacctaccag ggagtgaacc tacgcatcat tgcggcccat       360
gaggtgggcc acgccctggg acttgggcat tcccgatata cccaggcact catggcgcct       420
gtttacgctg gctaccagcc ctacttcagg ctgcatccgg atgatgtggc agggatccag       480
gcgctctatg caagaggag gccggagcca aagatgagg aggaagaggt ggagatgcac        540
actgtgtcaa cagtgaccac aaaacccagt cccatgccaa cccctgcag cagtgaagtg        600 gatgccatga tgctagggcc tcggggggaag acctatgctt tcaagggtga ctatgtgtgg       660
actgtaacag attcagggcc agggcccttg ttccgagtgt ctgccctttg ggaggggctt       720
cctggaaacc tggatgctgc tgtctactct ccccggacac agcggactca tttcttcaag       780
ggaaacaagg tgtggcggta tgtggatttc aagttgtctc ctggctttcc catgaaactc       840
aacagagtgg aacccaacct agatgcagct ctctattggc ctgttaatca gaaggtgttc       900 cttttttaagg gctcaggata ctggcaatgg gatgaactga ccagaactga cctcagtcgc       960
taccccaaac caatcaagga acttttcact ggagtgccag accaaccctc agcagctatg      1020
agctggcaag atggccaagt ctacttcttc aagggcaaag agtactggcg ccttaaccag      1080
caacttcgag tggcaaaggg ctatcccaga aatacgacac actggatgca ctgtagtcct      1140
cggactccag acactaactc attaactggg gatgtgacca ctcctgcaac cgtggaatca      1200
gtcttggatg ttccctctgc cacagacgct gcctccctct catcctcagc taatgtcacc      1260
ttgctagggg cc                                                           1272
```

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: synthetic primer

<400> SEQUENCE: 13

```
gctgacatcc gcctctcctt                                                    20
```

<210> SEQ ID NO 14
<211> LENGTH: 20
<212> TYPE: DNA
<213> ORGANISM: Artificial Sequence

```
<220> FEATURE:
<223> OTHER INFORMATION: Description of Artificial Sequence: synthetic
      primer

<400> SEQUENCE: 14
gggcccggtc ctgaaatctg                                                    20

<210> SEQ ID NO 15
<211> LENGTH: 29
<212> TYPE: DNA
<213> ORGANISM: Artificial Sequence
<220> FEATURE:
<223> OTHER INFORMATION: Description of Artificial Sequence: synthetic
      primer

<400> SEQUENCE: 15
cccgcatgct acctgttgct gggccgctg                                          29

<210> SEQ ID NO 16
<211> LENGTH: 33
<212> TYPE: DNA
<213> ORGANISM: Artificial Sequence
<220> FEATURE:
<223> OTHER INFORMATION: Description of Artificial Sequence: synthetic
      primer

<400> SEQUENCE: 16
aagctgcaga tctacggtct tgcgcctgct aca                                     33

<210> SEQ ID NO 17
<211> LENGTH: 19
<212> TYPE: DNA
<213> ORGANISM: Artificial Sequence
<220> FEATURE:
<223> OTHER INFORMATION: Description of Artificial Sequence: synthetic
      primer

<400> SEQUENCE: 17
ggcagggatc caggctctc                                                     19

<210> SEQ ID NO 18
<211> LENGTH: 18
<212> TYPE: DNA
<213> ORGANISM: Artificial Sequence
<220> FEATURE:
<223> OTHER INFORMATION: Description of Artificial Sequence: synthetic
      primer

<400> SEQUENCE: 18
tgcatccagg ttaggttc                                                      18

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: synthetic
      primer

<400> SEQUENCE: 19
gccggagcca gaagatgagg                                                    20

<210> SEQ ID NO 20
<211> LENGTH: 10
<212> TYPE: PRT
<213> ORGANISM: Artificial Sequence
<220> FEATURE:
```

-continued

<223> OTHER INFORMATION: Description of Artificial Sequence:
      illustrative peptide

<400> SEQUENCE: 20

Met Arg Lys Pro Arg Cys Gly Val Pro Asp
 1               5                  10

<210> SEQ ID NO 21
<211> LENGTH: 7
<212> TYPE: PRT
<213> ORGANISM: Artificial Sequence
<220> FEATURE:
<223> OTHER INFORMATION: Description of Artificial Sequence:
      illustrative substrate
<220> FEATURE:
<221> NAME/KEY: MOD_RES
<222> LOCATION: (2)
<223> OTHER INFORMATION: Cha
<220> FEATURE:
<221> NAME/KEY: MOD_RES
<222> LOCATION: (3)
<223> OTHER INFORMATION: Abu
<220> FEATURE:
<221> NAME/KEY: MOD_RES
<222> LOCATION: (4)
<223> OTHER INFORMATION: Cys(Me)
<220> FEATURE:
<221> NAME/KEY: MOD_RES
<222> LOCATION: (7)
<223> OTHER INFORMATION: Lys(N-Me-Abz)

<400> SEQUENCE: 21

Pro Xaa Xaa Cys His Ala Lys
 1               5

<210> SEQ ID NO 22
<211> LENGTH: 2264
<212> TYPE: DNA
<213> ORGANISM: Homo sapiens
<220> FEATURE:
<221> NAME/KEY: CDS
<222> LOCATION: (95)..(1618)

<400> SEQUENCE: 22
aagagcccct ctgcctagca ctgctccccc aaggctccca gaaatctcag gtcagaggca      60
cggacagcct ctggagctct cgtctggtgg gacc atg aac tgc cag cag ctg tgg    115
                                    Met Asn Cys Gln Gln Leu Trp
                                     1               5 ctg ggc ttc cta ctc ccc atg aca gtc tca ggc cgg gtc ctg ggg ctt       163
Leu Gly Phe Leu Leu Pro Met Thr Val Ser Gly Arg Val Leu Gly Leu
        10                  15                  20 gca gag gtg gcg ccc gtg gac tac ctg tca caa tat ggg tac cta cag       211
Ala Glu Val Ala Pro Val Asp Tyr Leu Ser Gln Tyr Gly Tyr Leu Gln
 25                  30                  35 aag cct cta gaa gga tct aat aac ttc aag cca gaa gat atc acc gag       259
Lys Pro Leu Glu Gly Ser Asn Asn Phe Lys Pro Glu Asp Ile Thr Glu
 40                  45                  50                  55 gct ctg aga gct ttt cag gaa gca tct gaa ctt cca gtc tca ggt cag       307
Ala Leu Arg Ala Phe Gln Glu Ala Ser Glu Leu Pro Val Ser Gly Gln
                 60                  65                  70 ctg gat gat gcc aca agg gcc cgc atg agg cag cct cgt tgt ggc cta       355
Leu Asp Asp Ala Thr Arg Ala Arg Met Arg Gln Pro Arg Cys Gly Leu
             75                  80                  85 gag gat ccc ttc aac cag aag acc ctt aaa tac ctg ttg ctg ggc cgc       403
Glu Asp Pro Phe Asn Gln Lys Thr Leu Lys Tyr Leu Leu Leu Gly Arg
         90                  95                 100

-continued

| | |
|---|---|
| tgg aga aag aag cac ctg act ttc cgc atc ttg aac ctg ccc tcc acc<br>Trp Arg Lys Lys His Leu Thr Phe Arg Ile Leu Asn Leu Pro Ser Thr<br>105                110                      115 | 451 |
| ctt cca ccc cac aca gcc cgg gca gcc ctg cgt caa gcc ttc cag gac<br>Leu Pro Pro His Thr Ala Arg Ala Ala Leu Arg Gln Ala Phe Gln Asp<br>120                125                      130                      135 | 499 |
| tgg agc aat gtg gct ccc ttg acc ttc caa gag gtg cag gct ggt gcg<br>Trp Ser Asn Val Ala Pro Leu Thr Phe Gln Glu Val Gln Ala Gly Ala<br>                140                      145                      150 | 547 |
| gct gac atc cgc ctc tcc ttc cat ggc cgc caa agc tcg tac tgt tcc<br>Ala Asp Ile Arg Leu Ser Phe His Gly Arg Gln Ser Ser Tyr Cys Ser<br>                155                      160                      165 | 595 |
| aat act ttt gat ggg cct ggg aga gtt ctg gcc cat gcc gac atc cca<br>Asn Thr Phe Asp Gly Pro Gly Arg Val Leu Ala His Ala Asp Ile Pro<br>        170                      175                      180 | 643 |
| gag ctg ggc agt gtg cac ttc gac gaa gac gag ttc tgg act gag ggg<br>Glu Leu Gly Ser Val His Phe Asp Glu Asp Glu Phe Trp Thr Glu Gly<br>185                190                      195 | 691 |
| acc tac cgt ggg gtg aac ctg cgc atc att gca gcc cat gaa gtg ggc<br>Thr Tyr Arg Gly Val Asn Leu Arg Ile Ile Ala Ala His Glu Val Gly<br>200                      205                      210                      215 | 739 |
| cat gct ctg ggg ctt ggg cac tcc cga tat tcc cag gcc ctc atg gcc<br>His Ala Leu Gly Leu Gly His Ser Arg Tyr Ser Gln Ala Leu Met Ala<br>                220                      225                      230 | 787 |
| cca gtc tac gag ggc tac cgg ccc cac ttt aag ctg cac cca gat gat<br>Pro Val Tyr Glu Gly Tyr Arg Pro His Phe Lys Leu His Pro Asp Asp<br>        235                      240                      245 | 835 |
| gtg gca ggg atc cag gct ctc tat ggc aag aag agt cca gtg ata agg<br>Val Ala Gly Ile Gln Ala Leu Tyr Gly Lys Lys Ser Pro Val Ile Arg<br>                250                      255                      260 | 883 |
| gat gag gaa gaa gaa gag aca gag ctg ccc act gtg ccc cca gtg ccc<br>Asp Glu Glu Glu Glu Glu Thr Glu Leu Pro Thr Val Pro Pro Val Pro<br>265                270                      275 | 931 |
| aca gaa ccc agt ccc atg cca gac cct tgc agt agt gaa ctg gat gcc<br>Thr Glu Pro Ser Pro Met Pro Asp Pro Cys Ser Ser Glu Leu Asp Ala<br>280                      285                      290                      295 | 979 |
| atg atg ctg ggg ccc cgt ggg aag acc tat gct ttc aag ggg gac tat<br>Met Met Leu Gly Pro Arg Gly Lys Thr Tyr Ala Phe Lys Gly Asp Tyr<br>                300                      305                      310 | 1027 |
| gtg tgg act gta tca gat tca gga ccg ggc ccc ttg ttc cga gtg tct<br>Val Trp Thr Val Ser Asp Ser Gly Pro Gly Pro Leu Phe Arg Val Ser<br>                315                      320                      325 | 1075 |
| gcc ctt tgg gag ggg ctc ccc gga aac ctg gat gct gct gtc tac tcg<br>Ala Leu Trp Glu Gly Leu Pro Gly Asn Leu Asp Ala Ala Val Tyr Ser<br>        330                      335                      340 | 1123 |
| cct cga aca caa tgg att cac ttc ttt aag gga gac aag gtg tgg cgc<br>Pro Arg Thr Gln Trp Ile His Phe Phe Lys Gly Asp Lys Val Trp Arg<br>345                350                      355 | 1171 |
| tac att aat ttc aag atg tct cct ggc ttc ccc aag aag ctg aat agg<br>Tyr Ile Asn Phe Lys Met Ser Pro Gly Phe Pro Lys Lys Leu Asn Arg<br>360                365                      370                      375 | 1219 |
| gta gaa cct aac ctg gat gca gct ctc tat tgg cct ctc aac caa aag<br>Val Glu Pro Asn Leu Asp Ala Ala Leu Tyr Trp Pro Leu Asn Gln Lys<br>                380                      385                      390 | 1267 |
| gtg ttc ctc ttt aag ggc tcc ggg tac tgg cag tgg gac gag cta gcc<br>Val Phe Leu Phe Lys Gly Ser Gly Tyr Trp Gln Trp Asp Glu Leu Ala<br>                395                      400                      405 | 1315 |
| cga act gac ttc agc agc tac ccc aaa cca atc aag ggt ttg ttt acg<br>Arg Thr Asp Phe Ser Ser Tyr Pro Lys Pro Ile Lys Gly Leu Phe Thr<br>        410                      415                      420 | 1363 |

```
gga gtg cca aac cag ccc tcg gct gct atg agt tgg caa gat ggc cga      1411
Gly Val Pro Asn Gln Pro Ser Ala Ala Met Ser Trp Gln Asp Gly Arg
        425                 430                 435 gtc tac ttc ttc aag ggc aaa gtc tac tgg cgc ctc aac cag cag ctt      1459
Val Tyr Phe Phe Lys Gly Lys Val Tyr Trp Arg Leu Asn Gln Gln Leu
440                 445                 450                 455 cga gta gag aaa ggc tat ccc aga aat att tcc cac aac tgg atg cac      1507
Arg Val Glu Lys Gly Tyr Pro Arg Asn Ile Ser His Asn Trp Met His
                460                 465                 470 tgt cgt ccc cgg act ata gac act acc cca tca ggt ggg aat acc act      1555
Cys Arg Pro Arg Thr Ile Asp Thr Thr Pro Ser Gly Gly Asn Thr Thr
            475                 480                 485 ccc tca ggt acg ggc ata acc ttg gat acc act ctc tca gcc aca gaa      1603
Pro Ser Gly Thr Gly Ile Thr Leu Asp Thr Thr Leu Ser Ala Thr Glu
        490                 495                 500 acc acg ttt gaa tac tgactgctca cccacagaca caatcttgga cattaacccc     1658
Thr Thr Phe Glu Tyr
    505 tgaggctcca ccaccaccc tttcatttcc cccccagaag cctaaggcct aatagctgaa    1718 tgaaatacct gtctgctcag tagaaccttg caggtgctgt agcaggcgca agaccgtaga   1778 tttcaggctt ttaacacttc caactccagc caccactttc ctgtgcattt tcactcctga   1838 gaagtgctcc cctaactcag atcccctaac ttagatttgg cccccaactc catttcctgt   1898 ctgtcttaga cagcccttcc aactgtgtca tctcttctct ggaggtcaat ggtggaggga   1958 gatgcctggg tcctgttctt cctacataaa atgcaagaaa acagcatggc cagtaaactg   2018 agcaagggcc ttggaatcct tgagaatcac atttatgtgc ttatgattac gggcaagcta   2078 attaaccttg ttgaatctca gattccccat ttgcaacatt aggttaagac cagtactgca   2138 ggattgttgc actaaatgaa atactgtatg tgaagtgcct ggcacagtgt ctggtacatt   2198 tgtgtttaat aaaagctaac tccatgttca taagagagga ctgaaaaaaa aaaaaaaaa   2258 aaaaaa                                                              2264

<210> SEQ ID NO 23
<211> LENGTH: 2049
<212> TYPE: DNA
<213> ORGANISM: Rattus sp.
<220> FEATURE:
<221> NAME/KEY: CDS
<222> LOCATION: (90)..(1640)

<400> SEQUENCE: 23
gtcccctgcc tagccctgtt cctccaagtt cccagaagtc tcaggtcaga gggctcaggc    60
agcttctgga actcttgtct gctgggacc atg gac tgg cag cag ctg tgg ctg    113
                                 Met Asp Trp Gln Gln Leu Trp Leu
                                  1               5 gcc ttc tta ctt cct gtg aca gtc tca ggc cgg gct ctg ggg cct gca     161
Ala Phe Leu Leu Pro Val Thr Val Ser Gly Arg Ala Leu Gly Pro Ala
        10                  15                  20 gag aag gag gcg gtg gtg gat tac ctg ttg cag tat ggg tat cta cag     209
Glu Lys Glu Ala Val Val Asp Tyr Leu Leu Gln Tyr Gly Tyr Leu Gln
25                  30                  35                  40 aaa cct ctg gaa gga gct gat gac ttc agg cta gaa gat atc aca gag     257
Lys Pro Leu Glu Gly Ala Asp Asp Phe Arg Leu Glu Asp Ile Thr Glu
                45                  50                  55 gct cta aga act ttc cag gaa gca tct gaa ctg cct gtt tcc ggt cag     305
Ala Leu Arg Thr Phe Gln Glu Ala Ser Glu Leu Pro Val Ser Gly Gln
            60                  65                  70
```

-continued

```
atg gat gat gcc aca agg gcc cgt atg aag cag ccc cgt tgt ggc ctg      353
Met Asp Asp Ala Thr Arg Ala Arg Met Lys Gln Pro Arg Cys Gly Leu
        75                  80                  85 gag gat cct ttc aac cag aag act ctg aaa tac ctg ctt ctg ggc cac      401
Glu Asp Pro Phe Asn Gln Lys Thr Leu Lys Tyr Leu Leu Leu Gly His
        90                  95                 100 tgg aga aag aag cac ttg aca ttc cgc atc ttg aac gtg ccc tcc acc      449
Trp Arg Lys Lys His Leu Thr Phe Arg Ile Leu Asn Val Pro Ser Thr
105                 110                 115                 120 ctc tca ccc tcc aga gtc cga gca gcc ctg cat caa gcc ttt aag tat      497
Leu Ser Pro Ser Arg Val Arg Ala Ala Leu His Gln Ala Phe Lys Tyr
                125                 130                 135 tgg agc aat gta gcc ccc ctg acc ttc cgg gag gtg aaa gct ggt tgg      545
Trp Ser Asn Val Ala Pro Leu Thr Phe Arg Glu Val Lys Ala Gly Trp
            140                 145                 150 gct gat atc cgc ctc tcg ttc cat ggc cgc caa agc cca tac tgc tcc      593
Ala Asp Ile Arg Leu Ser Phe His Gly Arg Gln Ser Pro Tyr Cys Ser
                155                 160                 165 aac agc ttt gat ggg cct ggg aag gtc ctg gcc cat gct gac gtc cca      641
Asn Ser Phe Asp Gly Pro Gly Lys Val Leu Ala His Ala Asp Val Pro
170                 175                 180 gag ctt ggc agt gta cac ttc gat aac gat gaa ttc tgg acc gag ggc      689
Glu Leu Gly Ser Val His Phe Asp Asn Asp Glu Phe Trp Thr Glu Gly
185                 190                 195                 200 acc tac cag gga gtg aac cta cgc atc att gcg gcc cat gag gtg ggc      737
Thr Tyr Gln Gly Val Asn Leu Arg Ile Ile Ala Ala His Glu Val Gly
                205                 210                 215 cac gcc ctg gga ctt ggg cat tcc cga tat acc cag gca ctc atg gcg      785
His Ala Leu Gly Leu Gly His Ser Arg Tyr Thr Gln Ala Leu Met Ala
                220                 225                 230 cct gtt tac gct ggc tac cag ccc tac ttc agg ctg cat ccg gat gat      833
Pro Val Tyr Ala Gly Tyr Gln Pro Tyr Phe Arg Leu His Pro Asp Asp
                235                 240                 245 gtg gca ggg atc cag gcg ctc tat ggc aag agg agg ccg gag cca gaa      881
Val Ala Gly Ile Gln Ala Leu Tyr Gly Lys Arg Arg Pro Glu Pro Glu
250                 255                 260 gat gag gag gaa gag gtg gag atg cac act gtg tca aca gtg acc aca      929
Asp Glu Glu Glu Glu Val Glu Met His Thr Val Ser Thr Val Thr Thr
265                 270                 275                 280 aaa ccc agt ccc atg cca aac ccc tgc agc agt gaa gtg gat gcc atg      977
Lys Pro Ser Pro Met Pro Asn Pro Cys Ser Ser Glu Val Asp Ala Met
                285                 290                 295 atg cta ggg cct cgg ggg aag acc tat gct ttc aag ggt gac tat gtg     1025
Met Leu Gly Pro Arg Gly Lys Thr Tyr Ala Phe Lys Gly Asp Tyr Val
            300                 305                 310 tgg act gta aca gat tca ggg cca ggg ccc ttg ttc cga gtg tct gcc     1073
Trp Thr Val Thr Asp Ser Gly Pro Gly Pro Leu Phe Arg Val Ser Ala
                315                 320                 325 ctt tgg gag ggg ctt cct gga aac ctg gat gct gct gtc tac tct ccc     1121
Leu Trp Glu Gly Leu Pro Gly Asn Leu Asp Ala Ala Val Tyr Ser Pro
330                 335                 340 cgg aca cag cgg act cat ttc ttc aag gga aac aag gtg tgg cgg tat     1169
Arg Thr Gln Arg Thr His Phe Phe Lys Gly Asn Lys Val Trp Arg Tyr
345                 350                 355                 360 gtg gat ttc aag ttg tct cct ggc ttt ccc atg aaa ctc aac aga gtg     1217
Val Asp Phe Lys Leu Ser Pro Gly Phe Pro Met Lys Leu Asn Arg Val
                365                 370                 375 gaa ccc aac cta gat gca gct ctc tat tgg cct gtt aat cag aag gtg     1265
Glu Pro Asn Leu Asp Ala Ala Leu Tyr Trp Pro Val Asn Gln Lys Val
```

-continued

```
                    380                 385                 390
ttc ctt ttt aag ggc tca gga tac tgg caa tgg gat gaa ctg acc aga    1313
Phe Leu Phe Lys Gly Ser Gly Tyr Trp Gln Trp Asp Glu Leu Thr Arg
        395                 400                 405 act gac ctc agt cgc tac ccc aaa cca atc aag gaa ctt ttc act gga    1361
Thr Asp Leu Ser Arg Tyr Pro Lys Pro Ile Lys Glu Leu Phe Thr Gly
    410                 415                 420 gtg cca gac caa ccc tca gca gct atg agc tgg caa gat ggc caa gtc    1409
Val Pro Asp Gln Pro Ser Ala Ala Met Ser Trp Gln Asp Gly Gln Val
425                 430                 435                 440 tac ttc ttc aag ggc aaa gag tac tgg cgc ctt aac cag caa ctt cga    1457
Tyr Phe Phe Lys Gly Lys Glu Tyr Trp Arg Leu Asn Gln Gln Leu Arg
                445                 450                 455 gtg gca aag ggc tat ccc aga aat acg aca cac tgg atg cac tgt agt    1505
Val Ala Lys Gly Tyr Pro Arg Asn Thr Thr His Trp Met His Cys Ser
                460                 465                 470 cct cgg act cca gac act aac tca tta act ggg gat gtg acc act cct    1553
Pro Arg Thr Pro Asp Thr Asn Ser Leu Thr Gly Asp Val Thr Thr Pro
            475                 480                 485 gca acc gtg gaa tca gtc ttg gat gtt ccc tct gcc aca gac gct gcc    1601
Ala Thr Val Glu Ser Val Leu Asp Val Pro Ser Ala Thr Asp Ala Ala
        490                 495                 500 tcc ctc tca tcc tca gct aat gtc acc ttg cta ggg gcc tgagaactag    1650
Ser Leu Ser Ser Ser Ala Asn Val Thr Leu Leu Gly Ala
505                 510                 515 tcagtgtctg ctccttaggg ttgtgcagat gggcacttga cctagtgccc ctagatactc  1710
caattctgga tgccacattc cagtgttcct agaaagtgac tgcttaattc tgagtcattc  1770
cccagtcccc atttcttctt gtcatatggc tgtttcaagt gtgacatcta ttttctggtg  1830
gagggaaatt gttgatcagg acccccccccc ccccagggt ctctctacat agcactggct  1890
atggttatcg gctatcctga aactgtgtag ttatgtagac taggctaact tgaactcaca  1950
gaaaccaacc tgcctctgcc tctgtcctga gtgctgggat taaaaacgtg tgctaccaaa  2010
aaaaaaaaaa aaaaaaaaaa aaaaaaaaaa aaaaaaaa                          2049
```